US011273001B2

(12) United States Patent
Shelton, IV et al.

(10) Patent No.: US 11,273,001 B2
(45) Date of Patent: Mar. 15, 2022

(54) SURGICAL HUB AND MODULAR DEVICE RESPONSE ADJUSTMENT BASED ON SITUATIONAL AWARENESS

(71) Applicant: Ethicon LLC, Guaynabo, PR (US)

(72) Inventors: Frederick E. Shelton, IV, Hillsboro, OH (US); Jeffrey D. Messerly, Cincinnati, OH (US); Jason L. Harris, Lebanon, OH (US)

(73) Assignee: Cilag GmbH International, Zug (CH)

(*) Notice: Subject to any disclaimer, the term of this patent is extended or adjusted under 35 U.S.C. 154(b) by 0 days.

(21) Appl. No.: 16/182,243

(22) Filed: Nov. 6, 2018

(65) Prior Publication Data

US 2019/0206542 A1 Jul. 4, 2019

Related U.S. Application Data

(60) Provisional application No. 62/729,177, filed on Sep. 10, 2018, provisional application No. 62/692,747, (Continued)

(51) Int. Cl.
*A61B 90/35* (2016.01)
*A61B 90/00* (2016.01)
(Continued)

(52) U.S. Cl.
CPC .......... *A61B 90/361* (2016.02); *A61B 17/072* (2013.01); *A61B 17/07207* (2013.01); (Continued)

(58) Field of Classification Search
CPC ......... G08B 19/00; A61B 34/35; A61B 34/37; A61B 90/361; A61B 90/98; A61B 17/072; A61B 17/07207; A61B 17/1155; A61B 18/00; A61B 18/14; A61B 18/1445; A61B 2034/301; A61B 2017/00017;
(Continued)

(56) References Cited

U.S. PATENT DOCUMENTS

| | | | |
|---|---|---|---|
| 1,853,416 | A | 4/1932 | Hall |
| 2,222,125 | A | 11/1940 | Stehlik |

(Continued)

FOREIGN PATENT DOCUMENTS

| | | | |
|---|---|---|---|
| AU | 2015201140 | A1 | 3/2015 |
| CA | 2795323 | A1 | 5/2014 |

(Continued)

OTHER PUBLICATIONS

US 10,504,709 B2, 12/2019, Karancsi et al. (withdrawn)
(Continued)

*Primary Examiner* — Amanda K Hulbert

(57) ABSTRACT

A surgical system for use in a surgical procedure is disclosed. The surgical system includes a modular device, at least one data source, and a surgical hub configured to communicably couple to the at least one data source and the modular device. The surgical hub comprises a control circuit configured to receive data from the at least one data source. The data is determinative of a progress status the surgical procedure. The control circuit is further configured to adjust a response to a sensed parameter based on the progress status.

20 Claims, 26 Drawing Sheets

102 119 112 117 106 108 107 109 111 120 114 112 124 110 118 122 116

Related U.S. Application Data filed on Jun. 30, 2018, provisional application No. 62/692,768, filed on Jun. 30, 2018, provisional application No. 62/692,748, filed on Jun. 30, 2018, provisional application No. 62/659,900, filed on Apr. 19, 2018, provisional application No. 62/650,898, filed on Mar. 30, 2018, provisional application No. 62/650,882, filed on Mar. 30, 2018, provisional application No. 62/650,887, filed on Mar. 30, 2018, provisional application No. 62/650,877, filed on Mar. 30, 2018, provisional application No. 62/640,415, filed on Mar. 8, 2018, provisional application No. 62/640,417, filed on Mar. 8, 2018, provisional application No. 62/611,340, filed on Dec. 28, 2017, provisional application No. 62/611,339, filed on Dec. 28, 2017, provisional application No. 62/611,341, filed on Dec. 28, 2017.

(51) Int. Cl.

*A61B 34/35* (2016.01)
*G16H 40/40* (2018.01)
*G16H 70/20* (2018.01)
*G16H 40/60* (2018.01)
*A61B 17/072* (2006.01)
*A61B 17/115* (2006.01)
*A61B 18/00* (2006.01)
*A61B 18/14* (2006.01)
*G06Q 10/06* (2012.01)
*G06Q 10/08* (2012.01)
*G16H 20/40* (2018.01)
*G16H 10/60* (2018.01)
*G05B 15/02* (2006.01)
*A61B 34/30* (2016.01)
*A61B 34/37* (2016.01)
*A61B 90/98* (2016.01)
*A61B 17/00* (2006.01)

(52) U.S. Cl.

CPC .......... *A61B 17/1155* (2013.01); *A61B 18/00* (2013.01); *A61B 18/14* (2013.01); *A61B 18/1445* (2013.01); *A61B 34/35* (2016.02); *G05B 15/02* (2013.01); *G06Q 10/0635* (2013.01); *G06Q 10/0833* (2013.01); *G16H 10/60* (2018.01); *G16H 20/40* (2018.01); *G16H 40/40* (2018.01); *G16H 40/60* (2018.01); *G16H 70/20* (2018.01); *A61B 34/37* (2016.02); *A61B 90/98* (2016.02); *A61B 2017/00017* (2013.01); *A61B 2017/00044* (2013.01); *A61B 2017/00057* (2013.01); *A61B 2017/00106* (2013.01); *A61B 2017/00119* (2013.01); *A61B 2017/00199* (2013.01); *A61B 2017/00221* (2013.01); *A61B 2017/00809* (2013.01); *A61B 2017/07271* (2013.01); *A61B 2017/07285* (2013.01); *A61B 2018/0063* (2013.01); *A61B 2018/00541* (2013.01); *A61B 2018/00601* (2013.01); *A61B 2018/00684* (2013.01); *A61B 2018/00839* (2013.01); *A61B 2018/00982* (2013.01); *A61B 2018/00994* (2013.01); *A61B 2034/301* (2016.02); *A61B 2218/002* (2013.01); *A61B 2218/008* (2013.01)

(58) Field of Classification Search

CPC ........... A61B 2017/00044; A61B 2017/00057; A61B 2017/00106; A61B 2017/00119; A61B 2017/00199; A61B 2017/00221; A61B 2017/00809; A61B 2017/07271; A61B 2017/07285; A61B 2018/00541; A61B 2018/00601; A61B 2018/0063; A61B 2018/00684; A61B 2018/00839; A61B 2018/00982; A61B 2018/00994; A61B 2218/002; A61B 2218/008; G16H 20/40; G16H 70/20; G05B 15/02; G06Q 10/0635; G06Q 10/0833; G06Q 50/22; H04W 76/14

See application file for complete search history.

(56) References Cited

U.S. PATENT DOCUMENTS

| | | | |
|---|---|---|---|
| 3,082,426 | A | 3/1963 | Miles |
| 3,503,396 | A | 3/1970 | Pierie et al. |
| 3,584,628 | A | 6/1971 | Green |
| 3,626,457 | A | 12/1971 | Duerr et al. |
| 3,633,584 | A | 1/1972 | Farrell |
| 3,759,017 | A | 9/1973 | Young |
| 3,863,118 | A | 1/1975 | Lander et al. |
| 3,898,545 | A | 8/1975 | Coppa et al. |
| 3,912,121 | A | 10/1975 | Steffen |
| 3,915,271 | A | 10/1975 | Harper |
| 3,932,812 | A | 1/1976 | Milligan |
| 4,041,362 | A | 8/1977 | Ichiyanagi |
| 4,052,649 | A | 10/1977 | Greenwell et al. |
| 4,087,730 | A | 5/1978 | Goles |
| 4,157,859 | A | 6/1979 | Terry |
| 4,202,722 | A | 5/1980 | Paquin |
| 4,412,539 | A | 11/1983 | Jarvik |
| 4,448,193 | A | 5/1984 | Ivanov |
| 4,523,695 | A | 6/1985 | Braun et al. |
| 4,608,160 | A | 8/1986 | Zoch |
| 4,614,366 | A | 9/1986 | North et al. |
| 4,633,874 | A | 1/1987 | Chow et al. |
| 4,701,193 | A | 10/1987 | Robertson et al. |
| 4,735,603 | A | 4/1988 | Goodson et al. |
| 4,788,977 | A | 12/1988 | Farin et al. |
| 4,892,244 | A | 1/1990 | Fox et al. |
| 5,010,341 | A | 4/1991 | Huntley et al. |
| 5,026,387 | A | 6/1991 | Thomas |
| 5,035,692 | A | 7/1991 | Lyon et al. |
| 5,042,460 | A | 8/1991 | Sakurai et al. |
| 5,084,057 | A | 1/1992 | Green et al. |
| 5,100,402 | A | 3/1992 | Fan |
| 5,129,570 | A | 7/1992 | Schulze et al. |
| 5,151,102 | A | 9/1992 | Kamiyama et al. |
| 5,156,315 | A | 10/1992 | Green et al. |
| 5,158,585 | A | 10/1992 | Saho et al. |
| 5,171,247 | A | 12/1992 | Hughett et al. |
| 5,197,962 | A | 3/1993 | Sansom et al. |
| 5,242,474 | A | 9/1993 | Herbst et al. |
| 5,253,793 | A | 10/1993 | Green et al. |
| 5,271,543 | A | 12/1993 | Grant et al. |
| RE34,519 | E | 1/1994 | Fox et al. |
| 5,275,323 | A | 1/1994 | Schulze et al. |
| 5,318,516 | A | 6/1994 | Cosmescu |
| 5,322,055 | A | 6/1994 | Davison et al. |
| 5,342,349 | A | 8/1994 | Kaufman |
| 5,383,880 | A | 1/1995 | Hooven |
| 5,396,900 | A | 3/1995 | Slater et al. |
| 5,397,046 | A | 3/1995 | Savage et al. |
| 5,403,312 | A | 4/1995 | Yates et al. |
| 5,403,327 | A | 4/1995 | Thornton et al. |
| 5,413,267 | A | 5/1995 | Solyntjes et al. |
| 5,415,335 | A | 5/1995 | Knodell, Jr. |
| 5,417,699 | A | 5/1995 | Klein et al. |
| 5,439,468 | A | 8/1995 | Schulze et al. |
| 5,445,304 | A | 8/1995 | Plyley et al. |
| 5,462,545 | A | 10/1995 | Wang et al. |
| 5,465,895 | A | 11/1995 | Knodel et al. |
| 5,467,911 | A | 11/1995 | Tsuruta et al. |
| 5,474,566 | A | 12/1995 | Alesi et al. |
| 5,485,947 | A | 1/1996 | Olson et al. |
| 5,496,315 | A | 3/1996 | Weaver et al. |
| 5,503,320 | A | 4/1996 | Webster et al. |
| 5,529,235 | A | 6/1996 | Boiarski et al. |
| 5,531,743 | A | 7/1996 | Nettekoven et al. |
| 5,545,148 | A | 8/1996 | Wurster |

(56) References Cited

U.S. PATENT DOCUMENTS

| | | | |
|---|---|---|---|
| 5,552,685 | A | 9/1996 | Young et al. |
| 5,560,372 | A | 10/1996 | Cory |
| 5,584,425 | A | 12/1996 | Savage et al. |
| 5,610,379 | A | 3/1997 | Muz et al. |
| 5,610,811 | A | 3/1997 | Honda |
| 5,613,966 | A | 3/1997 | Makower et al. |
| 5,624,452 | A | 4/1997 | Yates |
| 5,626,587 | A | 5/1997 | Bishop et al. |
| 5,643,291 | A | 7/1997 | Pier et al. |
| 5,654,750 | A | 8/1997 | Weil et al. |
| 5,673,841 | A | 10/1997 | Schulze et al. |
| 5,673,842 | A | 10/1997 | Bittner et al. |
| 5,675,227 | A | 10/1997 | Roos et al. |
| 5,693,052 | A | 12/1997 | Weaver |
| 5,695,502 | A | 12/1997 | Pier et al. |
| 5,697,926 | A | 12/1997 | Weaver |
| 5,706,998 | A | 1/1998 | Plyley et al. |
| 5,718,359 | A | 2/1998 | Palmer et al. |
| 5,725,536 | A | 3/1998 | Oberlin et al. |
| 5,725,542 | A | 3/1998 | Yoon |
| 5,735,445 | A | 4/1998 | Vidal et al. |
| 5,735,848 | A | 4/1998 | Yates et al. |
| 5,746,209 | A | 5/1998 | Yost et al. |
| 5,749,362 | A | 5/1998 | Funda et al. |
| 5,749,893 | A | 5/1998 | Vidal et al. |
| 5,752,644 | A | 5/1998 | Bolanos et al. |
| 5,762,255 | A | 6/1998 | Chrisman et al. |
| 5,766,186 | A | 6/1998 | Faraz et al. |
| 5,769,791 | A | 6/1998 | Benaron et al. |
| 5,775,331 | A | 7/1998 | Raymond et al. |
| 5,797,537 | A | 8/1998 | Oberlin et al. |
| 5,800,350 | A | 9/1998 | Coppleson et al. |
| D399,561 | S | 10/1998 | Ellingson |
| 5,817,093 | A | 10/1998 | Williamson, IV et al. |
| 5,820,009 | A | 10/1998 | Melling et al. |
| 5,833,690 | A | 11/1998 | Yates et al. |
| 5,836,849 | A | 11/1998 | Mathiak et al. |
| 5,836,909 | A | 11/1998 | Cosmescu |
| 5,843,080 | A | 12/1998 | Fleenor et al. |
| 5,846,237 | A | 12/1998 | Nettekoven |
| 5,849,022 | A | 12/1998 | Sakashita et al. |
| 5,873,873 | A | 2/1999 | Smith et al. |
| 5,878,938 | A | 3/1999 | Bittner et al. |
| 5,893,849 | A | 4/1999 | Weaver |
| 5,906,625 | A | 5/1999 | Bito et al. |
| 5,942,333 | A | 8/1999 | Arnett et al. |
| 5,947,996 | A | 9/1999 | Logeman |
| 5,968,032 | A | 10/1999 | Sleister |
| 5,980,510 | A | 11/1999 | Tsonton et al. |
| 5,987,346 | A | 11/1999 | Benaron et al. |
| 5,997,528 | A | 12/1999 | Bisch et al. |
| 6,010,054 | A | 1/2000 | Johnson et al. |
| 6,030,437 | A | 2/2000 | Gourrier et al. |
| 6,036,637 | A | 3/2000 | Kudo |
| 6,039,734 | A | 3/2000 | Goble |
| 6,039,735 | A | 3/2000 | Greep |
| 6,059,799 | A | 5/2000 | Aranyi et al. |
| 6,066,137 | A | 5/2000 | Greep |
| 6,079,606 | A | 6/2000 | Milliman et al. |
| 6,090,107 | A | 7/2000 | Borgmeier et al. |
| 6,099,537 | A | 8/2000 | Sugai et al. |
| 6,102,907 | A | 8/2000 | Smethers et al. |
| 6,109,500 | A | 8/2000 | Alli et al. |
| 6,113,598 | A | 9/2000 | Baker |
| 6,126,592 | A | 10/2000 | Proch et al. |
| 6,126,658 | A | 10/2000 | Baker |
| 6,131,789 | A | 10/2000 | Schulze et al. |
| 6,155,473 | A | 12/2000 | Tompkins et al. |
| 6,214,000 | B1 | 4/2001 | Fleenor et al. |
| 6,258,105 | B1 | 7/2001 | Hart et al. |
| 6,273,887 | B1 | 8/2001 | Yamauchi et al. |
| 6,301,495 | B1 | 10/2001 | Gueziec et al. |
| 6,302,881 | B1 | 10/2001 | Farin |
| 6,308,089 | B1 | 10/2001 | von der Ruhr et al. |
| 6,325,808 | B1 | 12/2001 | Bernard et al. |
| 6,325,811 | B1 | 12/2001 | Messerly |
| 6,341,164 | B1 | 1/2002 | Dilkie et al. |
| 6,391,102 | B1 | 5/2002 | Bodden et al. |
| 6,434,416 | B1 | 8/2002 | Mizoguchi et al. |
| 6,443,973 | B1 | 9/2002 | Whitman |
| 6,451,015 | B1 | 9/2002 | Rittman, III et al. |
| 6,454,781 | B1 | 9/2002 | Witt et al. |
| 6,457,625 | B1 | 10/2002 | Tormala et al. |
| 6,461,352 | B2 | 10/2002 | Morgan et al. |
| 6,466,817 | B1 | 10/2002 | Kaula et al. |
| 6,480,796 | B2 | 11/2002 | Wiener |
| 6,524,307 | B1 | 2/2003 | Palmerton et al. |
| 6,530,933 | B1 | 3/2003 | Yeung et al. |
| 6,551,243 | B2 | 4/2003 | Bocionek et al. |
| 6,569,109 | B2 | 5/2003 | Sakurai et al. |
| 6,582,424 | B2 | 6/2003 | Fleenor et al. |
| 6,585,791 | B1 | 7/2003 | Garito et al. |
| 6,618,626 | B2 | 9/2003 | West, Jr. et al. |
| 6,648,223 | B2 | 11/2003 | Boukhny et al. |
| 6,678,552 | B2 | 1/2004 | Pearlman |
| 6,679,899 | B2 | 1/2004 | Wiener et al. |
| 6,685,704 | B2 | 2/2004 | Greep |
| 6,699,187 | B2 | 3/2004 | Webb et al. |
| 6,742,895 | B2 | 6/2004 | Robin |
| 6,752,816 | B2 | 6/2004 | Culp et al. |
| 6,760,616 | B2 | 7/2004 | Hoey et al. |
| 6,770,072 | B1 | 8/2004 | Truckai et al. |
| 6,773,444 | B2 | 8/2004 | Messerly |
| 6,775,575 | B2 | 8/2004 | Bommannan et al. |
| 6,778,846 | B1 | 8/2004 | Martinez et al. |
| 6,781,683 | B2 | 8/2004 | Kacyra et al. |
| 6,783,524 | B2 | 8/2004 | Anderson et al. |
| 6,783,525 | B2 | 8/2004 | Greep et al. |
| 6,793,663 | B2 | 9/2004 | Kneifel et al. |
| 6,824,539 | B2 | 11/2004 | Novak |
| 6,846,308 | B2 | 1/2005 | Whitman et al. |
| 6,849,074 | B2 | 2/2005 | Chen et al. |
| 6,852,219 | B2 | 2/2005 | Hammond |
| 6,863,650 | B1 | 3/2005 | Irion |
| 6,869,430 | B2 | 3/2005 | Balbierz et al. |
| 6,869,435 | B2 | 3/2005 | Blake, III |
| 6,911,033 | B2 | 6/2005 | de Guillebon et al. |
| 6,937,892 | B2 | 8/2005 | Leyde et al. |
| 6,945,981 | B2 | 9/2005 | Donofrio et al. |
| 6,951,559 | B1 | 10/2005 | Greep |
| 6,962,587 | B2 | 11/2005 | Johnson et al. |
| 6,978,921 | B2 | 12/2005 | Shelton, IV et al. |
| 6,988,649 | B2 | 1/2006 | Shelton, IV et al. |
| 7,000,818 | B2 | 2/2006 | Shelton, IV et al. |
| 7,030,146 | B2 | 4/2006 | Baynes et al. |
| 7,032,798 | B2 | 4/2006 | Whitman et al. |
| 7,041,941 | B2 | 5/2006 | Faries, Jr. et al. |
| 7,044,352 | B2 | 5/2006 | Shelton, IV et al. |
| 7,044,911 | B2 | 5/2006 | Drinan et al. |
| 7,048,775 | B2 | 5/2006 | Jornitz et al. |
| 7,053,752 | B2 | 5/2006 | Wang et al. |
| 7,055,730 | B2 | 6/2006 | Ehrenfels et al. |
| 7,073,765 | B2 | 7/2006 | Newkirk |
| 7,077,853 | B2 | 7/2006 | Kramer et al. |
| 7,077,856 | B2 | 7/2006 | Whitman |
| 7,081,096 | B2 | 7/2006 | Brister et al. |
| 7,097,640 | B2 | 8/2006 | Wang et al. |
| 7,103,688 | B2 | 9/2006 | Strong |
| 7,104,949 | B2 | 9/2006 | Anderson et al. |
| 7,118,564 | B2 | 10/2006 | Ritchie et al. |
| 7,121,460 | B1 | 10/2006 | Parsons et al. |
| 7,137,980 | B2 | 11/2006 | Buysse et al. |
| 7,140,528 | B2 | 11/2006 | Shelton, IV |
| 7,143,923 | B2 | 12/2006 | Shelton, IV et al. |
| 7,143,925 | B2 | 12/2006 | Shelton, IV et al. |
| 7,147,139 | B2 | 12/2006 | Schwemberger et al. |
| 7,155,316 | B2 | 12/2006 | Sutherland et al. |
| 7,164,940 | B2 | 1/2007 | Hareyama et al. |
| 7,169,145 | B2 | 1/2007 | Isaacson et al. |
| 7,177,533 | B2 | 2/2007 | McFarlin et al. |
| 7,182,775 | B2 | 2/2007 | de Guillebon et al. |
| 7,208,005 | B2 | 4/2007 | Frecker et al. |
| 7,230,529 | B2 | 6/2007 | Ketcherside, Jr. et al. |
| 7,232,447 | B2 | 6/2007 | Gellman et al. |

(56) References Cited

U.S. PATENT DOCUMENTS 7,236,817 B2 6/2007 Papas et al.
7,246,734 B2 7/2007 Shelton, IV
7,278,563 B1 10/2007 Green
7,294,106 B2 11/2007 Birkenbach et al.
7,294,116 B1 11/2007 Ellman et al.
7,296,724 B2 11/2007 Green et al.
7,317,955 B2 1/2008 McGreevy
7,328,828 B2 2/2008 Ortiz et al.
7,334,717 B2 2/2008 Rethy et al.
7,343,565 B2 3/2008 Ying et al.
7,362,228 B2 4/2008 Nycz et al.
7,371,227 B2 5/2008 Zeiner
7,380,695 B2 6/2008 Doll et al.
7,383,088 B2 6/2008 Spinelli et al.
7,391,173 B2 6/2008 Schena
7,407,074 B2 8/2008 Ortiz et al.
7,422,139 B2 9/2008 Shelton, IV et al.
7,423,972 B2 9/2008 Shaham et al.
7,457,804 B2 11/2008 Uber, III et al.
7,464,847 B2 12/2008 Viola et al.
7,464,849 B2 12/2008 Shelton, IV et al.
7,515,961 B2 4/2009 Germanson et al.
7,568,604 B2 8/2009 Ehrenfels et al.
7,575,144 B2 8/2009 Ortiz et al.
7,597,731 B2 10/2009 Palmerton et al.
7,617,137 B2 11/2009 Kreiner et al.
7,621,192 B2 11/2009 Conti et al.
7,621,898 B2 11/2009 Lalomia et al.
7,631,793 B2 12/2009 Rethy et al.
7,637,410 B2 12/2009 Marczyk
7,641,092 B2 1/2010 Kruszynski et al.
7,644,848 B2 1/2010 Swayze et al.
7,667,592 B2 2/2010 Ohyama et al.
7,667,839 B2 2/2010 Bates
7,670,334 B2 3/2010 Hueil et al.
7,694,865 B2 4/2010 Scirica
7,699,860 B2 4/2010 Huitema et al.
7,720,306 B2 5/2010 Gardiner et al.
7,721,934 B2 5/2010 Shelton, IV et al.
7,721,936 B2 5/2010 Shalton, IV et al.
7,736,357 B2 6/2010 Lee, Jr. et al.
7,742,176 B2 6/2010 Braunecker et al.
7,743,960 B2 6/2010 Whitman et al.
7,753,245 B2 7/2010 Boudreaux et al.
7,766,207 B2 8/2010 Mather et al.
7,766,905 B2 8/2010 Paterson et al.
7,770,773 B2 8/2010 Whitman et al.
7,771,429 B2 8/2010 Ballard et al.
7,776,037 B2 8/2010 Odom
7,782,789 B2 8/2010 Stultz et al.
7,784,663 B2 8/2010 Shelton, IV
7,803,151 B2 9/2010 Whitman
7,810,692 B2 10/2010 Hall et al.
7,818,041 B2 10/2010 Kim et al.
7,819,298 B2 10/2010 Hall et al.
7,832,612 B2 11/2010 Baxter, III et al.
7,833,219 B2 11/2010 Tashiro et al.
7,836,085 B2 11/2010 Petakov et al.
7,837,079 B2 11/2010 Holsten et al.
7,837,680 B2 11/2010 Isaacson et al.
7,841,980 B2 11/2010 Minosawa et al.
7,845,537 B2 12/2010 Shelton, IV et al.
7,857,185 B2 12/2010 Swayze et al.
7,862,560 B2 1/2011 Marion
7,862,579 B2 1/2011 Ortiz et al.
7,865,236 B2 1/2011 Cory et al.
7,884,735 B2 2/2011 Newkirk
7,887,530 B2 2/2011 Zemlok et al.
7,892,337 B2 2/2011 Palmerton et al.
7,907,166 B2 3/2011 Lamprecht et al.
7,913,891 B2 3/2011 Doll et al.
7,918,230 B2 4/2011 Whitman et al.
7,918,377 B2 4/2011 Measamer et al.
7,920,706 B2 4/2011 Asokan et al.
7,927,014 B2 4/2011 Dehler
7,942,300 B2 5/2011 Rethy et al.
7,954,682 B2 6/2011 Giordano et al.
7,955,322 B2 6/2011 Devengenzo et al.
7,956,620 B2 6/2011 Gilbert
7,963,433 B2 6/2011 Whitman et al.
7,966,269 B2 6/2011 Bauer et al.
7,967,180 B2 6/2011 Scirica
7,976,553 B2 7/2011 Shelton, IV et al.
7,979,157 B2 7/2011 Anvari
7,980,443 B2 7/2011 Scheib et al.
7,982,776 B2 7/2011 Dunki-Jacobs et al.
7,988,028 B2 8/2011 Farascioni et al.
7,993,140 B2 8/2011 Sakezles
7,995,045 B2 8/2011 Dunki-Jacobs
8,005,947 B2 8/2011 Morris et al.
8,007,494 B1 8/2011 Taylor et al.
8,007,513 B2 8/2011 Nalagatla et al.
8,010,180 B2 8/2011 Quaid et al.
8,012,170 B2 9/2011 Whitman et al.
8,015,976 B2 9/2011 Shah
8,016,855 B2 9/2011 Whitman et al.
8,025,199 B2 9/2011 Whitman et al.
8,027,710 B1 9/2011 Dannan
8,035,685 B2 10/2011 Jensen
8,038,686 B2 10/2011 Huitema et al.
8,038,693 B2 10/2011 Allen
8,043,560 B2 10/2011 Okumoto et al.
8,054,184 B2 11/2011 Cline et al.
8,054,752 B2 11/2011 Druke et al.
8,062,306 B2 11/2011 Nobis et al.
8,062,330 B2 11/2011 Prommersberger et al.
8,066,721 B2 11/2011 Kortenbach et al.
8,074,861 B2 12/2011 Ehrenfels et al.
8,075,571 B2 12/2011 Vitali et al.
8,096,459 B2 1/2012 Ortiz et al.
8,118,206 B2 2/2012 Zand et al.
8,120,301 B2 2/2012 Goldberg et al.
8,123,764 B2 2/2012 Meade et al.
8,128,625 B2 3/2012 Odom
8,131,565 B2 3/2012 Dicks et al.
8,136,712 B2 3/2012 Zingman
8,147,486 B2 4/2012 Honour et al.
8,155,479 B2 4/2012 Hoffman et al.
8,157,145 B2 4/2012 Shelton, IV et al.
8,157,150 B2 4/2012 Viola et al.
8,157,151 B2 4/2012 Ingmanson et al.
8,160,098 B1 4/2012 Yan et al.
8,160,690 B2 4/2012 Wilfley et al.
8,161,977 B2 4/2012 Shelton, IV et al.
8,170,396 B2 5/2012 Kuspa et al.
8,172,836 B2 5/2012 Ward
8,181,839 B2 5/2012 Beetel
8,185,409 B2 5/2012 Putnam et al.
8,206,345 B2 6/2012 Abboud et al.
8,208,707 B2 6/2012 Mendonca et al.
8,210,411 B2 7/2012 Yates et al.
8,214,007 B2 7/2012 Baker et al.
8,216,849 B2 7/2012 Petty
8,220,688 B2 7/2012 Laurent et al.
8,225,643 B2 7/2012 Abboud et al.
8,225,979 B2 7/2012 Farascioni et al.
8,229,549 B2 7/2012 Whitman et al.
8,231,042 B2 7/2012 Hessler et al.
8,241,322 B2 8/2012 Whitman et al.
8,255,045 B2 8/2012 Gharib et al.
8,257,387 B2 9/2012 Cunningham
8,260,016 B2 9/2012 Maeda et al.
8,262,560 B2 9/2012 Whitman
8,292,639 B2 10/2012 Achammer et al.
8,292,888 B2 10/2012 Whitman
8,295,902 B2 10/2012 Salahieh et al.
8,308,040 B2 11/2012 Huang et al.
8,321,581 B2 11/2012 Katis et al.
8,322,590 B2 12/2012 Patel et al.
8,328,065 B2 12/2012 Shah
8,335,590 B2 12/2012 Costa et al.
8,343,065 B2 1/2013 Bartol et al.
8,346,392 B2 1/2013 Walser et al.
8,360,299 B2 1/2013 Zemlok et al.

(56) References Cited

U.S. PATENT DOCUMENTS 8,364,222 B2 1/2013 Cook et al.
8,365,975 B1 2/2013 Manoux et al.
8,388,652 B2 3/2013 Viola
8,393,514 B2 3/2013 Shelton, IV et al.
8,397,972 B2 3/2013 Kostrzewski
8,398,541 B2 3/2013 DiMaio et al.
8,403,944 B2 3/2013 Pain et al.
8,403,945 B2 3/2013 Whitfield et al.
8,403,946 B2 3/2013 Whitfield et al.
8,406,859 B2 3/2013 Zuzak et al.
8,411,034 B2 4/2013 Boillot et al.
8,413,871 B2 4/2013 Racenet et al.
8,422,035 B2 4/2013 Hinderling et al.
8,423,182 B2 4/2013 Robinson et al.
8,428,722 B2 4/2013 Verhoef et al.
8,439,910 B2 5/2013 Greep et al.
8,444,663 B2 5/2013 Houser et al.
8,452,615 B2 5/2013 Abri
8,454,506 B2 6/2013 Rothman et al.
8,461,744 B2 6/2013 Wiener et al.
8,468,030 B2 6/2013 Stroup et al.
8,469,973 B2 6/2013 Meade et al.
8,472,630 B2 6/2013 Konrad et al.
8,476,227 B2 7/2013 Kaplan et al.
8,489,235 B2 7/2013 Moll et al.
8,499,992 B2 8/2013 Whitman et al.
8,500,756 B2 8/2013 Papa et al.
8,503,759 B2 8/2013 Greer et al.
8,505,801 B2 8/2013 Ehrenfels et al.
8,506,478 B2 8/2013 Mizuyoshl
8,512,325 B2 8/2013 Mathonnet
8,512,365 B2 8/2013 Wiener et al.
8,515,520 B2 8/2013 Brunnett et al.
8,517,239 B2 8/2013 Scheib et al.
8,521,331 B2 8/2013 Itkowitz
8,523,043 B2 9/2013 Ullrich et al.
8,546,996 B2 10/2013 Messerly et al.
8,554,697 B2 10/2013 Claus et al.
8,560,047 B2 10/2013 Haider et al.
8,561,870 B2 10/2013 Baxter, III et al.
8,562,598 B2 10/2013 Falkenstein et al.
8,566,115 B2 10/2013 Moore
8,571,598 B2 10/2013 Valavi
8,573,459 B2 11/2013 Smith et al.
8,573,465 B2 11/2013 Shelton, IV
8,585,694 B2 11/2013 Amoah et al.
8,590,762 B2 11/2013 Hess et al.
8,591,536 B2 11/2013 Robertson
8,595,607 B2 11/2013 Nekoomaram et al.
8,596,513 B2 12/2013 Olson et al.
8,596,515 B2 12/2013 Okoniewski
8,604,709 B2 12/2013 Jalbout et al.
8,608,044 B2 12/2013 Hueil et al.
8,608,045 B2 12/2013 Smith et al.
8,616,431 B2 12/2013 Timm et al.
8,620,055 B2 12/2013 Barratt et al.
8,620,473 B2 12/2013 Diolaiti et al.
8,623,027 B2 1/2014 Price et al.
8,627,483 B2 1/2014 Rachlin et al.
8,627,993 B2 1/2014 Smith et al.
8,627,995 B2 1/2014 Smith et al.
8,628,518 B2 1/2014 Blumenkranz et al.
8,628,545 B2 1/2014 Cabrera et al.
8,631,987 B2 1/2014 Shelton, IV et al.
8,632,525 B2 1/2014 Kerr et al.
8,636,190 B2 1/2014 Zemlok et al.
8,636,736 B2 1/2014 Yates et al.
8,641,621 B2 2/2014 Razzaque et al.
8,652,086 B2 2/2014 Gerg et al.
8,652,121 B2 2/2014 Quick et al.
8,652,128 B2 2/2014 Ward
8,657,176 B2 2/2014 Shelton, IV et al.
8,657,177 B2 2/2014 Scirica et al.
8,663,220 B2 3/2014 Wiener et al.
8,666,544 B2 3/2014 Moll et al.
8,679,114 B2 3/2014 Chapman et al.
8,682,049 B2 3/2014 Zhao et al.
8,682,489 B2 3/2014 Itkowitz et al.
8,685,056 B2 4/2014 Evans et al.
8,688,188 B2 4/2014 Heller et al.
8,690,864 B2 4/2014 Hoarau
8,701,962 B2 4/2014 Kostrzewski
8,719,061 B2 5/2014 Birchall
8,720,766 B2 5/2014 Hess et al.
8,733,613 B2 5/2014 Huitema et al.
8,740,840 B2 6/2014 Foley et al.
8,740,866 B2 6/2014 Reasoner et al.
8,747,238 B2 6/2014 Shelton, IV et al.
8,752,749 B2 6/2014 Moore et al.
8,757,465 B2 6/2014 Woodard, Jr. et al.
8,761,717 B1 6/2014 Buchheit
8,763,879 B2 7/2014 Shelton, IV et al.
8,768,251 B2 7/2014 Claus et al.
8,771,270 B2 7/2014 Burbank
8,775,196 B2 7/2014 Simpson et al.
8,779,648 B2 7/2014 Giordano et al.
8,790,253 B2 7/2014 Sunagawa et al.
8,794,497 B2 8/2014 Zingman
8,799,008 B2 8/2014 Johnson et al.
8,799,009 B2 8/2014 Mellin et al.
8,800,838 B2 8/2014 Shelton, IV
8,801,703 B2 8/2014 Gregg et al.
8,814,996 B2 8/2014 Giurgiutiu et al.
8,818,556 B2 8/2014 Sanchez et al.
8,820,603 B2 9/2014 Shelton, IV et al.
8,820,608 B2 9/2014 Miyamoto
8,827,134 B2 9/2014 Viola et al.
8,840,003 B2 9/2014 Morgan et al.
8,851,354 B2 10/2014 Swensgard et al.
8,852,174 B2 10/2014 Burbank
8,875,973 B2 11/2014 Whitman
8,882,662 B2 11/2014 Charles
8,886,790 B2 11/2014 Harrang et al.
8,893,949 B2 11/2014 Shelton, IV et al.
8,899,479 B2 12/2014 Cappuzzo et al.
8,905,977 B2 12/2014 Shelton et al.
8,912,746 B2 12/2014 Reid et al.
8,914,098 B2 12/2014 Brennan et al.
8,918,207 B2 12/2014 Prisco
8,920,414 B2 12/2014 Stone et al.
8,920,433 B2 12/2014 Barrier et al.
8,930,203 B2 1/2015 Kiaie et al.
8,930,214 B2 1/2015 Woolford
8,931,679 B2 1/2015 Kostrzewski
8,936,614 B2 1/2015 Allen, IV
8,945,095 B2 2/2015 Blumenkranz et al.
8,945,163 B2 2/2015 Voegele et al.
8,955,732 B2 2/2015 Zemlok et al.
8,956,581 B2 2/2015 Rosenbaum et al.
8,960,519 B2 2/2015 Whitman et al.
8,960,520 B2 2/2015 McCuen
8,962,062 B2 2/2015 Podhajsky et al.
8,967,443 B2 3/2015 McCuen
8,967,455 B2 3/2015 Zhou
8,968,276 B2 3/2015 Zemlok et al.
8,968,309 B2 3/2015 Roy et al.
8,968,312 B2 3/2015 Marczyk et al.
8,968,337 B2 3/2015 Whitfield et al.
8,968,358 B2 3/2015 Reschke
8,974,429 B2 3/2015 Gordon et al.
8,979,890 B2 3/2015 Boudreaux
8,986,302 B2 3/2015 Aldridge et al.
8,989,903 B2 3/2015 Weir et al.
8,991,678 B2 3/2015 Wellman et al.
8,992,565 B2 3/2015 Brisson et al.
8,998,797 B2 4/2015 Omori
9,002,518 B2 4/2015 Manzo et al.
9,010,611 B2 4/2015 Ross et al.
9,011,366 B2 4/2015 Dean et al.
9,011,427 B2 4/2015 Price et al.
9,016,539 B2 4/2015 Kostrzewski et al.
9,017,326 B2 4/2015 DiNardo et al.
9,020,240 B2 4/2015 Pettersson et al.
9,023,032 B2 5/2015 Robinson

(56) References Cited

U.S. PATENT DOCUMENTS 9,023,071 B2 5/2015 Miller et al.
9,027,431 B2 5/2015 Tang et al.
9,028,494 B2 5/2015 Shelton, IV et al.
9,035,568 B2 5/2015 Ganton et al.
9,038,882 B2 5/2015 Racenet et al.
9,043,027 B2 5/2015 Durant et al.
9,044,227 B2 6/2015 Shelton, IV et al.
9,044,244 B2 6/2015 Ludwin et al.
9,044,261 B2 6/2015 Houser
9,050,063 B2 6/2015 Roe et al.
9,050,083 B2 6/2015 Yates et al.
9,050,120 B2 6/2015 Swarup et al.
9,052,809 B2 6/2015 Vesto
9,055,035 B2 6/2015 Porsch et al.
9,060,770 B2 6/2015 Shelton, IV et al.
9,060,775 B2 6/2015 Wiener et al.
9,066,650 B2 6/2015 Sekiguchi
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,727 B2 7/2015 Miller
9,084,606 B2 7/2015 Greep
9,089,360 B2 7/2015 Messerly et al.
9,095,362 B2 8/2015 Dachs, II et al.
9,095,367 B2 8/2015 Olson et al.
9,099,863 B2 8/2015 Smith et al.
9,101,358 B2 8/2015 Kerr et al.
9,101,359 B2 8/2015 Smith et al.
9,101,374 B1 8/2015 Hoch et al.
9,106,270 B2 8/2015 Puterbaugh et al.
9,107,573 B2 8/2015 Birnkrant
9,107,662 B2 8/2015 Kostrzewski
9,107,684 B2 8/2015 Ma
9,107,688 B2 8/2015 Kimball et al.
9,107,689 B2 8/2015 Robertson et al.
9,107,694 B2 8/2015 Hendriks et al.
9,111,548 B2 8/2015 Nandy et al.
9,113,880 B2 8/2015 Zemlok et al.
9,114,494 B1 8/2015 Mah
9,116,597 B1 8/2015 Gulasky
9,119,617 B2 9/2015 Souls et al.
9,119,655 B2 9/2015 Bowling et al.
9,119,657 B2 9/2015 Shelton, IV et al.
9,123,155 B2 9/2015 Cunningham et al.
9,125,644 B2 9/2015 Lane et al.
9,129,054 B2 9/2015 Nawana et al.
9,137,254 B2 9/2015 Bilbrey et al.
9,138,129 B2 9/2015 Diolaiti
9,138,225 B2 9/2015 Huang et al.
9,149,322 B2 10/2015 Knowlton
9,155,503 B2 10/2015 Cadwell
9,161,803 B2 10/2015 Yates et al.
9,168,054 B2 10/2015 Turner et al.
9,168,104 B2 10/2015 Dein
9,179,912 B2 11/2015 Yates et al.
9,183,723 B2 11/2015 Sherman et al.
9,186,143 B2 11/2015 Timm et al.
9,192,375 B2 11/2015 Skinlo et al.
9,192,447 B2 11/2015 Choi et al.
9,192,707 B2 11/2015 Gerber et al.
9,202,078 B2 12/2015 Abuelsaad et al.
9,204,830 B2 12/2015 Zand et al.
9,204,879 B2 12/2015 Shelton, IV
9,204,995 B2 12/2015 Scheller et al.
9,216,062 B2 12/2015 Duque et al.
9,218,053 B2 12/2015 Komuro et al.
9,220,502 B2 12/2015 Zemlok et al.
9,226,689 B2 1/2016 Jacobsen et al.
9,226,751 B2 1/2016 Shelton, IV et al.
9,226,766 B2 1/2016 Aldridge et al.
9,226,767 B2 1/2016 Stulen et al.
9,232,883 B2 1/2016 Ozawa et al.
9,237,891 B2 1/2016 Shelton, IV
9,237,921 B2 1/2016 Messerly et al.
9,241,728 B2 1/2016 Price et al.
9,241,730 B2 1/2016 Babaev
9,241,731 B2 1/2016 Boudreaux et al.
9,247,996 B1 2/2016 Merana et al.
9,250,172 B2 2/2016 Harris et al.
9,255,907 B2 2/2016 Heanue et al.
9,265,585 B2 2/2016 Wingardner et al.
9,272,406 B2 3/2016 Aronhalt et al.
9,277,956 B2 3/2016 Zhang
9,280,884 B1 3/2016 Schultz et al.
9,282,962 B2 3/2016 Schmid et al.
9,282,974 B2 3/2016 Shelton, IV
9,283,045 B2 3/2016 Rhee et al.
9,283,054 B2 3/2016 Morgan et al.
9,289,211 B2 3/2016 Williams et al.
9,289,212 B2 3/2016 Shelton, IV et al.
9,295,514 B2 3/2016 Shelton, IV et al.
9,301,691 B2 4/2016 Hufnagel et al.
9,301,753 B2 4/2016 Aldridge et al.
9,301,759 B2 4/2016 Spivey et al.
9,301,810 B2 4/2016 Amiri et al.
9,302,213 B2 4/2016 Manahan et al.
9,307,894 B2 4/2016 von Grunberg et al.
9,307,914 B2 4/2016 Fahey
9,307,986 B2 4/2016 Hall et al.
9,314,246 B2 4/2016 Shelton, IV et al.
9,314,308 B2 4/2016 Parihar et al.
9,320,563 B2 4/2016 Brustad et al.
9,325,732 B1 4/2016 Stickle et al.
9,326,767 B2 5/2016 Koch et al.
9,331,422 B2 5/2016 Nazzaro et al.
9,332,987 B2 5/2016 Leimbach et al.
9,333,042 B2 5/2016 Diolaiti et al.
9,336,385 B1 5/2016 Spencer et al.
9,341,704 B2 5/2016 Picard et al.
9,345,481 B2 5/2016 Hall et al.
9,345,490 B2 5/2016 Ippisch
9,345,546 B2 5/2016 Toth et al.
9,351,726 B2 5/2016 Leimbach et al.
9,351,727 B2 5/2016 Leimbach et al.
9,358,003 B2 6/2016 Hall et al.
9,358,685 B2 6/2016 Meier et al.
9,360,449 B2 6/2016 Duric
9,364,231 B2 6/2016 Wenchell
9,364,249 B2 6/2016 Kimball et al.
9,364,294 B2 6/2016 Razzaque et al.
9,370,400 B2 6/2016 Parihar
9,375,282 B2 6/2016 Nau, Jr. et al.
9,375,539 B2 6/2016 Stearns et al.
9,381,003 B2 7/2016 Todor et al.
9,381,058 B2 7/2016 Houser et al.
9,386,984 B2 7/2016 Aronhalt et al.
9,386,988 B2 7/2016 Baxter, III et al.
9,387,295 B1 7/2016 Mastri et al.
9,393,017 B2 7/2016 Flanagan et al.
9,393,037 B2 7/2016 Olson et al.
9,398,905 B2 7/2016 Martin
9,398,911 B2 7/2016 Auld
9,402,629 B2 8/2016 Ehrenfels et al.
9,414,776 B2 8/2016 Sillay et al.
9,414,940 B2 8/2016 Stein et al.
9,419,018 B2 8/2016 Sasagawa et al.
9,421,014 B2 8/2016 Ingmanson et al.
9,433,470 B2 9/2016 Choi
9,439,622 B2 9/2016 Case et al.
9,439,668 B2 9/2016 Timm et al.
9,439,736 B2 9/2016 Olson
9,445,764 B2 9/2016 Gross et al.
9,445,813 B2 9/2016 Shelton, IV et al.
9,450,701 B2 9/2016 Do et al.
9,451,949 B2 9/2016 Gorek et al.
9,451,958 B2 9/2016 Shelton, IV et al.
9,463,022 B2 10/2016 Swayze et al.
9,468,438 B2 10/2016 Baber et al.
9,480,492 B2 11/2016 Aranyi et al.
9,485,475 B2 11/2016 Speier et al.
9,492,146 B2 11/2016 Kostrzewski et al.
9,492,237 B2 11/2016 Kang et al.
9,493,807 B2 11/2016 Little et al.

(56) References Cited

U.S. PATENT DOCUMENTS 9,498,182 B2 11/2016 Case et al.
9,498,215 B2 11/2016 Duque et al.
9,498,231 B2 11/2016 Haider et al.
9,516,239 B2 12/2016 Blanquart et al.
9,519,753 B1 12/2016 Gerdeman et al.
9,522,003 B2 12/2016 Weir et al.
9,526,407 B2 12/2016 Hoeg et al.
9,526,499 B2 12/2016 Kostrzewski et al.
9,526,587 B2 12/2016 Zhao et al.
9,532,845 B1 1/2017 Dossett et al.
9,539,007 B2 1/2017 Dhakad et al.
9,539,020 B2 1/2017 Conlon et al.
9,542,481 B2 1/2017 Halter et al.
9,546,662 B2 1/2017 Shener-Lrmakoglu et al.
9,549,781 B2 1/2017 He et al.
9,554,692 B2 1/2017 Levy
9,554,794 B2 1/2017 Baber et al.
9,554,854 B2 1/2017 Yates et al.
9,561,038 B2 2/2017 Shelton, IV et al.
9,561,045 B2 2/2017 Hinman et al.
9,566,708 B2 2/2017 Kurnianto
9,572,592 B2 2/2017 Price et al.
9,579,503 B2 2/2017 McKinney et al.
9,585,657 B2 3/2017 Shelton, IV et al.
9,592,095 B2 3/2017 Panescu et al.
9,597,081 B2 3/2017 Swayze et al.
9,600,138 B2 3/2017 Thomas et al.
9,603,024 B2 3/2017 Wang et al.
9,610,114 B2 4/2017 Baxter, III et al.
9,622,684 B2 4/2017 Wybo
9,622,808 B2 4/2017 Beller et al.
9,628,501 B2 4/2017 Datta Ray et al.
9,629,560 B2 4/2017 Joseph
9,629,623 B2 4/2017 Lytle, IV et al.
9,629,628 B2 4/2017 Aranyi
9,629,629 B2 4/2017 Leimbach et al.
9,630,318 B2 4/2017 Ibarz Gabardos et al.
9,636,188 B2 5/2017 Gattani et al.
9,636,239 B2 5/2017 Durand et al.
9,636,825 B2 5/2017 Penn et al.
9,641,596 B2 5/2017 Unagami et al.
9,641,815 B2 5/2017 Richardson et al.
9,642,620 B2 5/2017 Baxter, III et al.
9,643,022 B2 5/2017 Mashiach et al.
9,649,110 B2 5/2017 Parihar et al.
9,649,111 B2 5/2017 Shelton, IV et al.
9,649,126 B2 5/2017 Robertson et al.
9,649,169 B2 5/2017 Cinquin et al.
9,652,655 B2 5/2017 Satish et al.
9,655,616 B2 5/2017 Aranyi
9,656,092 B2 5/2017 Golden
9,662,116 B2 5/2017 Smith et al.
9,662,177 B2 5/2017 Weir et al.
9,668,729 B2 6/2017 Williams et al.
9,668,732 B2 6/2017 Patel et al.
9,668,765 B2 6/2017 Grace et al.
9,671,860 B2 6/2017 Ogawa et al.
9,675,264 B2 6/2017 Acquista et al.
9,675,354 B2 6/2017 Weir et al.
9,681,870 B2 6/2017 Baxter, III et al.
9,686,306 B2 6/2017 Chizeck et al.
9,687,230 B2 6/2017 Leimbach et al.
9,690,362 B2 6/2017 Leimbach et al.
9,700,292 B2 7/2017 Nawana et al.
9,700,309 B2 7/2017 Jaworek et al.
9,700,312 B2 7/2017 Kostrzewski et al.
9,700,320 B2 7/2017 Dinardo et al.
9,706,993 B2 7/2017 Hessler et al.
9,710,214 B2 7/2017 Lin et al.
9,710,644 B2 7/2017 Reybok et al.
9,713,424 B2 7/2017 Spaide
9,717,141 B1 7/2017 Tegg
9,717,498 B2 8/2017 Aranyi et al.
9,717,525 B2 8/2017 Ahluwalia et al.
9,717,548 B2 8/2017 Couture
9,724,094 B2 8/2017 Baber et al.
9,724,100 B2 8/2017 Scheib et al.
9,724,118 B2 8/2017 Schulte et al.
9,733,663 B2 8/2017 Leimbach et al.
9,737,301 B2 8/2017 Baber et al.
9,737,310 B2 8/2017 Whitfield et al.
9,737,335 B2 8/2017 Butler et al.
9,737,355 B2 8/2017 Yates et al.
9,740,826 B2 8/2017 Raghavan et al.
9,743,016 B2 8/2017 Nestares et al.
9,743,929 B2 8/2017 Leimbach et al.
9,743,946 B2 8/2017 Faller et al.
9,743,947 B2 8/2017 Price et al.
9,750,499 B2 9/2017 Leimbach et al.
9,750,500 B2 9/2017 Malkowski
9,750,522 B2 9/2017 Scheib et al.
9,750,523 B2 9/2017 Tsubuku
9,753,135 B2 9/2017 Bosch
9,753,568 B2 9/2017 McMillen
9,757,126 B2 9/2017 Cappola
9,757,128 B2 9/2017 Baber et al.
9,757,142 B2 9/2017 Shimizu
9,757,152 B2 9/2017 Ogilvie et al.
9,763,741 B2 9/2017 Alvarez et al.
9,764,164 B2 9/2017 Wiener et al.
9,770,541 B2 9/2017 Carr et al.
9,775,611 B2 10/2017 Kostrzewski
9,777,913 B2 10/2017 Talbert et al.
9,782,164 B2 10/2017 Mumaw et al.
9,782,169 B2 10/2017 Kimsey et al.
9,782,212 B2 10/2017 Wham et al.
9,782,214 B2 10/2017 Houser et al.
9,788,835 B2 10/2017 Morgan et al.
9,788,836 B2 10/2017 Overmyer et al.
9,788,851 B2 10/2017 Dannaher et al.
9,788,902 B2 10/2017 Inoue et al.
9,788,907 B1 10/2017 Alvi et al.
9,795,436 B2 10/2017 Yates et al.
9,797,486 B2 10/2017 Zergiebel et al.
9,801,531 B2 10/2017 Morita et al.
9,801,626 B2 10/2017 Parihar et al.
9,801,627 B2 10/2017 Harris et al.
9,801,679 B2 10/2017 Trees et al.
9,802,033 B2 10/2017 Hibner et al.
9,804,618 B2 10/2017 Leimbach et al.
9,805,472 B2 10/2017 Chou et al.
9,808,244 B2 11/2017 Leimbach et al.
9,808,245 B2 11/2017 Richard et al.
9,808,246 B2 11/2017 Shelton, IV et al.
9,808,248 B2 11/2017 Hoffman
9,808,249 B2 11/2017 Shelton, IV
9,814,457 B2 11/2017 Martin et al.
9,814,460 B2 11/2017 Kimsey et al.
9,814,462 B2 11/2017 Woodard, Jr. et al.
9,814,463 B2 11/2017 Williams et al.
9,820,699 B2 11/2017 Bingley et al.
9,820,738 B2 11/2017 Lytle, IV et al.
9,820,741 B2 11/2017 Kostrzewski
9,826,976 B2 11/2017 Parihar et al.
9,826,977 B2 11/2017 Leimbach et al.
9,827,054 B2 11/2017 Richmond et al.
9,827,059 B2 11/2017 Robinson et al.
9,830,424 B2 11/2017 Dixon et al.
9,833,241 B2 12/2017 Huitema et al.
9,839,419 B2 12/2017 Deck et al.
9,839,424 B2 12/2017 Zergiebel et al.
9,839,428 B2 12/2017 Baxter, III et al.
9,839,470 B2 12/2017 Gilbert et al.
9,839,487 B2 12/2017 Dachs, II
9,844,368 B2 12/2017 Boudreaux et al.
9,844,369 B2 12/2017 Huitema et al.
9,844,374 B2 12/2017 Lytle, IV et al.
9,844,375 B2 12/2017 Overmyer et al.
9,844,379 B2 12/2017 Shelton, IV et al.
9,848,058 B2 12/2017 Johnson et al.
9,848,877 B2 12/2017 Shelton, IV et al.
9,861,354 B2 1/2018 Saliman et al.
9,861,363 B2 1/2018 Chen et al.
9,861,428 B2 1/2018 Trees et al.

(56) References Cited

U.S. PATENT DOCUMENTS 9,867,612 B2 1/2018 Parihar et al.
9,867,651 B2 1/2018 Wham
9,867,914 B2 1/2018 Bonano et al.
9,872,609 B2 1/2018 Levy
9,872,683 B2 1/2018 Hopkins et al.
9,877,718 B2 1/2018 Weir et al.
9,877,721 B2 1/2018 Schellin et al.
9,883,860 B2 2/2018 Leimbach
9,888,864 B2 2/2018 Rondon et al.
9,888,914 B2 2/2018 Martin et al.
9,888,919 B2 2/2018 Leimbach et al.
9,888,921 B2 2/2018 Williams et al.
9,888,975 B2 2/2018 Auld
9,895,148 B2 2/2018 Shelton, IV et al.
9,900,787 B2 2/2018 Ou
9,901,342 B2 2/2018 Shelton, IV et al.
9,901,406 B2 2/2018 State et al.
9,905,000 B2 2/2018 Chou et al.
9,907,550 B2 3/2018 Sniffin et al.
9,913,642 B2 3/2018 Leimbach et al.
9,913,645 B2 3/2018 Zerkle et al.
9,918,730 B2 3/2018 Trees et al.
9,918,778 B2 3/2018 Walberg et al.
9,918,788 B2 3/2018 Paul et al.
9,922,304 B2 3/2018 DeBusk et al.
9,924,941 B2 3/2018 Burbank
9,924,944 B2 3/2018 Shelton, IV et al.
9,924,961 B2 3/2018 Shelton, IV et al.
9,931,040 B2 4/2018 Homyk et al.
9,931,118 B2 4/2018 Shelton, IV et al.
9,931,124 B2 4/2018 Gokharu
9,936,863 B2 4/2018 Tesar
9,936,942 B2 4/2018 Chin et al.
9,936,955 B2 4/2018 Miller et al.
9,936,961 B2 4/2018 Chien et al.
9,937,012 B2 4/2018 Hares et al.
9,937,014 B2 4/2018 Bowling et al.
9,937,626 B2 4/2018 Rockrohr
9,938,972 B2 4/2018 Walley
9,943,230 B2 4/2018 Kaku et al.
9,943,309 B2 4/2018 Shelton, IV et al.
9,943,312 B2 4/2018 Posada et al.
9,943,377 B2 4/2018 Yates et al.
9,943,379 B2 4/2018 Gregg, II et al.
9,943,918 B2 4/2018 Grogan et al.
9,949,785 B2 4/2018 Price et al.
9,962,157 B2 5/2018 Sapre
9,968,355 B2 5/2018 Shelton, IV et al.
9,980,140 B1 5/2018 Spencer et al.
9,980,769 B2 5/2018 Trees et al.
9,980,778 B2 5/2018 Ohline et al.
9,987,000 B2 6/2018 Shelton, IV et al.
9,990,856 B2 6/2018 Kuchenbecker et al.
9,993,248 B2 6/2018 Shelton, IV et al.
9,993,258 B2 6/2018 Shelton, IV et al.
9,993,305 B2 6/2018 Andersson
10,004,491 B2 6/2018 Martin et al.
10,004,497 B2 6/2018 Overmyer et al.
10,004,500 B2 6/2018 Shelton, IV et al.
10,004,501 B2 6/2018 Shelton, IV et al.
10,004,527 B2 6/2018 Gee et al.
10,004,557 B2 6/2018 Gross
D822,206 S 7/2018 Shelton, IV et al.
10,010,322 B2 7/2018 Shelton, IV et al.
10,010,324 B2 7/2018 Huitema et al.
10,013,049 B2 7/2018 Leimbach et al.
10,016,199 B2 7/2018 Baber et al.
10,021,318 B2 7/2018 Hugosson et al.
10,022,090 B2 7/2018 Whitman
10,022,120 B2 7/2018 Martin et al.
10,022,391 B2 7/2018 Ruderman Chen et al.
10,022,568 B2 7/2018 Messerly et al.
10,028,744 B2 7/2018 Shelton, IV et al.
10,028,761 B2 7/2018 Leimbach et al.
10,028,788 B2 7/2018 Kang
10,034,704 B2 7/2018 Asher et al.
10,037,641 B2 7/2018 Hyde et al.
10,037,715 B2 7/2018 Toly et al.
D826,405 S 8/2018 Shelton, IV et al.
10,039,546 B2 8/2018 Williams et al.
10,039,564 B2 8/2018 Hibner et al.
10,039,565 B2 8/2018 Vezzu
10,041,822 B2 8/2018 Zemlok
10,044,791 B2 8/2018 Kamen et al.
10,045,704 B2 8/2018 Fagin et al.
10,045,776 B2 8/2018 Shelton, IV et al.
10,045,779 B2 8/2018 Savage et al.
10,045,781 B2 8/2018 Cropper et al.
10,045,813 B2 8/2018 Mueller
10,048,379 B2 8/2018 Markendorf et al.
10,052,044 B2 8/2018 Shelton, IV et al.
10,052,102 B2 8/2018 Baxter, III et al.
10,052,104 B2 8/2018 Shelton, IV et al.
10,054,441 B2 8/2018 Schorr et al.
10,058,393 B2 8/2018 Bonutti et al.
10,069,633 B2 9/2018 Gulati et al.
10,076,326 B2 9/2018 Yates et al.
10,080,618 B2 9/2018 Marshall et al.
10,084,833 B2 9/2018 McDonnell et al.
D831,209 S 10/2018 Huitema et al.
10,085,748 B2 10/2018 Morgan et al.
10,085,749 B2 10/2018 Cappola et al.
10,095,942 B2 10/2018 Mentese et al.
10,097,578 B2 10/2018 Baldonado et al.
10,098,527 B2 10/2018 Weisenburgh, II et al.
10,098,635 B2 10/2018 Burbank
10,098,642 B2 10/2018 Baxter, III et al.
10,098,705 B2 10/2018 Brisson et al.
10,105,140 B2 10/2018 Malinouskas et al.
10,105,142 B2 10/2018 Baxter, III et al.
10,111,658 B2 10/2018 Chowaniec et al.
10,111,665 B2 10/2018 Aranyi et al.
10,111,679 B2 10/2018 Baber et al.
10,117,649 B2 11/2018 Baxter et al.
10,117,651 B2 11/2018 Whitman et al.
10,117,702 B2 11/2018 Danziger et al.
10,118,119 B2 11/2018 Sappok
10,130,359 B2 11/2018 Hess et al.
10,130,360 B2 11/2018 Olson et al.
10,130,361 B2 11/2018 Yates et al.
10,130,367 B2 11/2018 Cappola et al.
10,133,248 B2 11/2018 Fitzsimmons et al.
10,135,242 B2 11/2018 Baber et al.
10,136,887 B2 11/2018 Shelton, IV et al.
10,136,891 B2 11/2018 Shelton, IV et al.
10,136,949 B2 11/2018 Felder et al.
10,143,526 B2 12/2018 Walker et al.
10,143,948 B2 12/2018 Bonitas et al.
10,149,680 B2 12/2018 Parihar et al.
10,152,789 B2 12/2018 Carnes et al.
10,154,841 B2 12/2018 Weaner et al.
10,159,044 B2 12/2018 Hrabak
10,159,481 B2 12/2018 Whitman et al.
10,159,483 B2 12/2018 Beckman et al.
10,164,466 B2 12/2018 Calderoni
10,166,025 B2 1/2019 Leimbach et al.
10,169,862 B2 1/2019 Andre et al.
10,172,687 B2 1/2019 Garbus et al.
10,175,096 B2 1/2019 Dickerson
10,175,127 B2 1/2019 Collins et al.
10,178,992 B2 1/2019 Wise et al.
10,179,413 B2 1/2019 Rockrohr
10,180,463 B2 1/2019 Beckman et al.
10,182,814 B2 1/2019 Okoniewski
10,182,816 B2 1/2019 Shelton, IV et al.
10,182,818 B2 1/2019 Hensel et al.
10,188,385 B2 1/2019 Kerr et al.
10,189,157 B2 1/2019 Schlegel et al.
10,190,888 B2 1/2019 Hryb et al.
10,194,891 B2 2/2019 Jeong et al.
10,194,907 B2 2/2019 Marczyk et al.
10,194,913 B2 2/2019 Nalagatla et al.
10,194,972 B2 2/2019 Yates et al.
10,197,803 B2 2/2019 Badiali et al.

(56) References Cited

U.S. PATENT DOCUMENTS 10,198,965 B2 2/2019 Hart
10,201,311 B2 2/2019 Chou et al.
10,201,349 B2 2/2019 Leimbach et al.
10,201,364 B2 2/2019 Leimbach et al.
10,201,365 B2 2/2019 Boudreaux et al.
10,205,708 B1 2/2019 Fletcher et al.
10,206,605 B2 2/2019 Shelton, IV et al.
10,206,752 B2 2/2019 Hares et al.
10,213,201 B2 2/2019 Shelton, IV et al.
10,213,203 B2 2/2019 Swayze et al.
10,213,266 B2 2/2019 Zemlok et al.
10,213,268 B2 2/2019 Dachs, II
10,219,491 B2 3/2019 Stiles, Jr. et al.
10,220,522 B2 3/2019 Rockrohr
10,222,750 B2 3/2019 Bang et al.
10,226,249 B2 3/2019 Jaworek et al.
10,226,250 B2 3/2019 Beckman et al.
10,226,302 B2 3/2019 Lacal et al.
10,231,634 B2 3/2019 Zand et al.
10,231,733 B2 3/2019 Ehrenfels et al.
10,231,775 B2 3/2019 Shelton, IV et al.
10,238,413 B2 3/2019 Hibner et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,033 B2 4/2019 Overmyer et al.
10,245,037 B2 4/2019 Conklin et al.
10,245,038 B2 4/2019 Hopkins et al.
10,251,661 B2 4/2019 Collings et al.
10,251,725 B2 4/2019 Valentine et al.
10,258,331 B2 4/2019 Shelton, IV et al.
10,258,359 B2 4/2019 Kapadia
10,258,362 B2 4/2019 Conlon
10,258,363 B2 4/2019 Worrell et al.
10,258,415 B2 4/2019 Harrah et al.
10,258,418 B2 4/2019 Shelton, IV et al.
10,258,425 B2 4/2019 Mustufa et al.
10,263,171 B2 4/2019 Wiener et al.
10,265,035 B2 4/2019 Fehre et al.
10,265,068 B2 4/2019 Harris et al.
10,265,072 B2 4/2019 Shelton, IV et al.
10,265,090 B2 4/2019 Ingmanson et al.
10,265,130 B2 4/2019 Hess et al.
10,271,840 B2 4/2019 Sapre
10,271,844 B2 4/2019 Valentine et al.
10,271,850 B2 4/2019 Williams
10,271,851 B2 4/2019 Shelton, IV et al.
D847,989 S 5/2019 Shelton, IV et al.
10,278,698 B2 5/2019 Racenet
10,278,778 B2 5/2019 State et al.
10,283,220 B2 5/2019 Azlzian et al.
10,285,694 B2 5/2019 Viola et al.
10,285,698 B2 5/2019 Cappola et al.
10,285,700 B2 5/2019 Scheib
10,285,705 B2 5/2019 Shelton, IV et al.
10,292,704 B2 5/2019 Harris et al.
10,292,707 B2 5/2019 Shelton, IV et al.
10,292,758 B2 5/2019 Boudreaux et al.
10,292,771 B2 5/2019 Wood et al.
10,293,129 B2 5/2019 Fox et al.
10,299,792 B2 5/2019 Huitema et al.
10,299,870 B2 5/2019 Connolly et al.
10,305,926 B2 5/2019 Mihan et al.
D850,617 S 6/2019 Shelton, IV et al.
10,307,159 B2 6/2019 Harris et al.
10,307,170 B2 6/2019 Parfett et al.
10,307,199 B2 6/2019 Farritor et al.
10,311,036 B1 6/2019 Hussam et al.
10,313,137 B2 6/2019 Aarnio et al.
10,314,577 B2 6/2019 Laurent et al.
10,314,582 B2 6/2019 Shelton, IV et al.
10,321,907 B2 6/2019 Shelton, IV et al.
10,321,964 B2 6/2019 Grover et al.
10,327,764 B2 6/2019 Harris et al.
10,335,147 B2 7/2019 Rector et al.
10,335,149 B2 7/2019 Baxter, III et al.
10,335,180 B2 7/2019 Johnson et al.
10,335,227 B2 7/2019 Heard
10,342,543 B2 7/2019 Shelton, IV et al.
10,342,602 B2 7/2019 Strobl et al.
10,342,623 B2 7/2019 Huelman et al.
10,343,102 B2 7/2019 Reasoner et al.
10,349,824 B2 7/2019 Claude et al.
10,349,941 B2 7/2019 Marczyk et al.
10,350,016 B2 7/2019 Burbank et al.
10,357,246 B2 7/2019 Shelton, IV et al.
10,357,247 B2 7/2019 Shelton, IV et al.
10,362,179 B2 7/2019 Harris
10,363,032 B2 7/2019 Scheib et al.
10,363,037 B2 7/2019 Aronhalt et al.
10,368,861 B2 8/2019 Baxter, III et al.
10,368,865 B2 8/2019 Harris et al.
10,368,867 B2 8/2019 Harris et al.
10,368,876 B2 8/2019 Bhatnagar et al.
10,368,894 B2 8/2019 Madan et al.
10,368,903 B2 8/2019 Morales et al.
10,376,263 B2 8/2019 Morgan et al.
10,376,305 B2 8/2019 Yates et al.
10,376,337 B2 8/2019 Kilroy et al.
10,376,338 B2 8/2019 Taylor et al.
10,378,893 B2 8/2019 Mankovskii
10,383,518 B2 8/2019 Abu-Tarif et al.
10,383,699 B2 8/2019 Kilroy et al.
10,384,021 B2 8/2019 Koeth et al.
10,390,718 B2 8/2019 Chen et al.
10,390,794 B2 8/2019 Kuroiwa et al.
10,390,825 B2 8/2019 Shelton, IV et al.
10,390,831 B2 8/2019 Holsten et al.
10,390,895 B2 8/2019 Henderson et al.
10,398,348 B2 9/2019 Osadchy et al.
10,398,434 B2 9/2019 Shelton, IV et al.
10,398,517 B2 9/2019 Eckert et al.
10,398,521 B2 9/2019 Itkowitz et al.
10,404,521 B2 9/2019 McChord et al.
10,404,801 B2 9/2019 Martch
10,405,857 B2 9/2019 Shelton, IV et al.
10,405,863 B2 9/2019 Wise et al.
10,413,291 B2 9/2019 Worthington et al.
10,413,293 B2 9/2019 Shelton, IV et al.
10,413,297 B2 9/2019 Harris et al.
10,417,446 B2 9/2019 Takeyama
10,420,552 B2 9/2019 Shelton, IV et al.
10,420,558 B2 9/2019 Nalagatla et al.
10,420,559 B2 9/2019 Marczyk et al.
10,420,620 B2 9/2019 Rockrohr
10,420,865 B2 9/2019 Reasoner et al.
10,422,727 B2 9/2019 Pliskin
10,426,466 B2 10/2019 Contini et al.
10,426,467 B2 10/2019 Miller et al.
10,426,468 B2 10/2019 Contini et al.
10,426,471 B2 10/2019 Shelton, IV et al.
10,426,481 B2 10/2019 Aronhalt et al.
10,433,837 B2 10/2019 Worthington et al.
10,433,844 B2 10/2019 Shelton, IV et al.
10,433,849 B2 10/2019 Shelton, IV et al.
10,433,918 B2 10/2019 Shelton, IV et al.
10,441,279 B2 10/2019 Shelton, IV et al.
10,441,345 B2 10/2019 Aldridge et al.
10,448,948 B2 10/2019 Shelton, IV et al.
10,448,950 B2 10/2019 Shelton, IV et al.
10,456,137 B2 10/2019 Vendely et al.
10,456,140 B2 10/2019 Shelton, IV et al.
10,456,193 B2 10/2019 Yates et al.
10,463,365 B2 11/2019 Williams
10,463,367 B2 11/2019 Kostrzewski et al.
10,463,371 B2 11/2019 Kostrzewski
10,463,436 B2 11/2019 Jackson et al.
10,470,762 B2 11/2019 Leimbach et al.
10,470,764 B2 11/2019 Baxter, III et al.
10,470,768 B2 11/2019 Harris et al.
10,470,791 B2 11/2019 Houser
10,471,254 B2 11/2019 Sano et al.
10,478,181 B2 11/2019 Shelton, IV et al.

(56) References Cited

U.S. PATENT DOCUMENTS 10,478,185 B2 11/2019 Nicholas
10,478,189 B2 11/2019 Bear et al.
10,478,190 B2 11/2019 Miller et al.
10,478,544 B2 11/2019 Friederichs et al.
10,485,450 B2 11/2019 Gupta et al.
10,485,542 B2 11/2019 Shelton, IV et al.
10,485,543 B2 11/2019 Shelton, IV et al.
10,492,783 B2 12/2019 Shelton, IV et al.
10,492,784 B2 12/2019 Beardsley et al.
10,492,785 B2 12/2019 Overmyer et al.
10,496,788 B2 12/2019 Amarasingham et al.
10,498,269 B2 12/2019 Zemlok et al.
10,499,891 B2 12/2019 Chaplin et al.
10,499,914 B2 12/2019 Huang et al.
10,499,915 B2 12/2019 Aranyi
10,499,994 B2 12/2019 Luks et al.
10,507,068 B2 12/2019 Kopp et al.
10,512,461 B2 12/2019 Gupta et al.
10,512,499 B2 12/2019 McHenry et al.
10,512,514 B2 12/2019 Nowlin et al.
10,517,588 B2 12/2019 Gupta et al.
10,517,595 B2 12/2019 Hunter et al.
10,517,596 B2 12/2019 Hunter et al.
10,517,686 B2 12/2019 Vokrot et al.
10,524,789 B2 1/2020 Swayze et al.
10,531,874 B2 1/2020 Morgan et al.
10,531,929 B2 1/2020 Widenhouse et al.
10,532,330 B2 1/2020 Diallo et al.
10,536,617 B2 1/2020 Liang et al.
10,537,324 B2 1/2020 Shelton, IV et al.
10,537,325 B2 1/2020 Bakos et al.
10,537,351 B2 1/2020 Shelton, IV et al.
10,542,978 B2 1/2020 Chowaniec et al.
10,542,979 B2 1/2020 Shelton, IV et al.
10,542,982 B2 1/2020 Beckman et al.
10,542,991 B2 1/2020 Shelton, IV et al.
10,548,504 B2 2/2020 Shelton, IV et al.
10,548,612 B2 2/2020 Martinez et al.
10,548,673 B2 2/2020 Harris et al.
10,552,574 B2 2/2020 Sweeney
10,555,675 B2 2/2020 Satish et al.
10,555,748 B2 2/2020 Yates et al.
10,555,750 B2 2/2020 Conlon et al.
10,555,769 B2 2/2020 Worrell et al.
10,561,422 B2 2/2020 Schellin et al.
10,561,471 B2 2/2020 Nichogi
10,568,625 B2 2/2020 Harris et al.
10,568,626 B2 2/2020 Shelton, IV et al.
10,568,632 B2 2/2020 Miller et al.
10,568,704 B2 2/2020 Savaii et al.
10,575,868 B2 3/2020 Hall et al.
10,582,928 B2 3/2020 Hunter et al.
10,582,931 B2 3/2020 Mujawar
10,582,964 B2 3/2020 Weinberg et al.
10,586,074 B2 3/2020 Rose et al.
10,588,625 B2 3/2020 Weaner et al.
10,588,629 B2 3/2020 Malinouskas et al.
10,588,630 B2 3/2020 Shelton, IV et al.
10,588,631 B2 3/2020 Shelton, IV et al.
10,588,632 B2 3/2020 Shelton, IV et al.
10,588,711 B2 3/2020 DiCarlo et al.
10,592,067 B2 3/2020 Merdan et al.
10,595,844 B2 3/2020 Nawana et al.
10,595,882 B2 3/2020 Parfett et al.
10,595,887 B2 3/2020 Shelton, IV et al.
10,595,930 B2 3/2020 Scheib et al.
10,595,952 B2 3/2020 Forrest et al.
10,602,848 B2 3/2020 Magana
10,603,036 B2 3/2020 Hunter et al.
10,603,128 B2 3/2020 Zergiebel et al.
10,610,223 B2 4/2020 Wellman et al.
10,610,224 B2 4/2020 Shelton, IV et al.
10,610,286 B2 4/2020 Wiener et al.
10,610,313 B2 4/2020 Bailey et al.
10,617,412 B2 4/2020 Shelton, IV et al.
10,617,414 B2 4/2020 Shelton, IV et al.
10,617,482 B2 4/2020 Houser et al.
10,617,484 B2 4/2020 Kilroy et al.
10,624,635 B2 4/2020 Harris et al.
10,624,691 B2 4/2020 Wiener et al.
10,631,423 B2 4/2020 Collins et al.
10,631,858 B2 4/2020 Burbank
10,631,912 B2 4/2020 McFarlin et al.
10,631,916 B2 4/2020 Horner et al.
10,631,917 B2 4/2020 Ineson
10,631,939 B2 4/2020 Dachs, II et al.
10,639,027 B2 5/2020 Shelton, IV et al.
10,639,034 B2 5/2020 Harris et al.
10,639,035 B2 5/2020 Shelton, IV et al.
10,639,036 B2 5/2020 Yates et al.
10,639,037 B2 5/2020 Shelton, IV et al.
10,639,039 B2 5/2020 Vendely et al.
10,639,098 B2 5/2020 Cosman et al.
10,639,111 B2 5/2020 Kopp
10,639,185 B2 5/2020 Agrawal et al.
10,653,413 B2 5/2020 Worthington et al.
10,653,476 B2 5/2020 Ross
10,653,489 B2 5/2020 Kopp
10,656,720 B1 5/2020 Holz
10,660,705 B2 5/2020 Piron et al.
10,667,809 B2 6/2020 Bakos et al.
10,667,810 B2 6/2020 Shelton, IV et al.
10,667,811 B2 6/2020 Harris et al.
10,667,877 B2 6/2020 Kapadia
10,674,897 B2 6/2020 Levy
10,675,021 B2 6/2020 Harris et al.
10,675,023 B2 6/2020 Cappola
10,675,024 B2 6/2020 Shelton, IV et al.
10,675,025 B2 6/2020 Swayze et al.
10,675,026 B2 6/2020 Harris et al.
10,675,035 B2 6/2020 Man
10,675,104 B2 6/2020 Kapadia
10,677,764 B2 6/2020 Ross et al.
10,679,758 B2 6/2020 Fox et al.
10,682,136 B2 6/2020 Harris et al.
10,682,138 B2 6/2020 Shelton, IV et al.
10,686,805 B2 6/2020 Reybok, Jr. et al.
10,687,806 B2 6/2020 Shelton, IV et al.
10,687,809 B2 6/2020 Shelton, IV et al.
10,687,810 B2 6/2020 Shelton, IV et al.
10,687,884 B2 6/2020 Wiener et al.
10,687,905 B2 6/2020 Kostrzewski
10,695,055 B2 6/2020 Shelton, IV et al.
10,695,081 B2 6/2020 Shelton, IV et al.
10,695,134 B2 6/2020 Barral et al.
10,702,270 B2 7/2020 Shelton, IV et al.
10,702,271 B2 7/2020 Aranyi et al.
10,709,446 B2 7/2020 Harris et al.
10,716,489 B2 7/2020 Kalvoy et al.
10,716,615 B2 7/2020 Shelton, IV et al.
10,716,639 B2 7/2020 Kapadia et al.
10,717,194 B2 7/2020 Griffiths et al.
10,722,222 B2 7/2020 Aranyi
10,722,233 B2 7/2020 Wellman
10,722,292 B2 7/2020 Arya et al.
D893,717 S 8/2020 Messerly et al.
10,729,458 B2 8/2020 Stoddard et al.
10,729,509 B2 8/2020 Shelton, IV et al.
10,733,267 B2 8/2020 Pedersen
10,736,219 B2 8/2020 Seow et al.
10,736,616 B2 8/2020 Scheib et al.
10,736,628 B2 8/2020 Yates et al.
10,736,629 B2 8/2020 Shelton, IV et al.
10,736,636 B2 8/2020 Baxter, III et al.
10,736,705 B2 8/2020 Scheib et al.
10,743,872 B2 8/2020 Leimbach et al.
10,748,115 B2 8/2020 Laster et al.
10,751,052 B2 8/2020 Stokes et al.
10,751,136 B2 8/2020 Farritor et al.
10,751,768 B2 8/2020 Hersey et al.
10,755,813 B2 8/2020 Shelton, IV et al.
D896,379 S 9/2020 Shelton, IV et al.
10,758,229 B2 9/2020 Shelton, IV et al.
10,758,230 B2 9/2020 Shelton, IV et al.

(56) References Cited

U.S. PATENT DOCUMENTS 10,758,294 B2 9/2020 Jones
10,758,310 B2 9/2020 Shelton, IV et al.
10,765,376 B2 9/2020 Brown, III et al.
10,765,424 B2 9/2020 Baxter, III et al.
10,765,427 B2 9/2020 Shelton, IV et al.
10,765,470 B2 9/2020 Yates et al.
10,772,630 B2 9/2020 Wixey
10,786,317 B2 9/2020 Zhou et al.
10,792,422 B2 10/2020 Douglas et al.
10,835,247 B2 11/2020 Shelton, IV et al.
10,842,897 B2 11/2020 Schwartz et al.
10,856,768 B2 12/2020 Osadchy et al.
10,864,037 B2 12/2020 Mun et al.
10,872,684 B2 12/2020 McNutt et al.
10,881,446 B2 1/2021 Strobl
10,902,944 B1 1/2021 Casey et al.
10,905,418 B2 2/2021 Shelton, IV et al.
10,905,420 B2 2/2021 Jasemian et al.
10,932,784 B2 3/2021 Mozdzierz et al.
11,058,501 B2 7/2021 Tokarchuk et al.
2002/0049551 A1 4/2002 Friedman et al.
2002/0072746 A1 6/2002 Lingenfelder et al.
2003/0009111 A1 1/2003 Cory et al.
2003/0093503 A1 5/2003 Yamaki et al.
2003/0114851 A1 6/2003 Truckai et al.
2003/0210812 A1 11/2003 Khamene et al.
2003/0223877 A1 12/2003 Anstine et al.
2004/0078236 A1 4/2004 Stoodley et al.
2004/0199180 A1 10/2004 Knodel et al.
2004/0199659 A1 10/2004 Ishikawa et al.
2004/0206365 A1 10/2004 Knowlton
2004/0243148 A1 12/2004 Wasielewski
2004/0243435 A1 12/2004 Williams
2005/0020909 A1 1/2005 Moctezuma de la Barrera et al.
2005/0023324 A1 2/2005 Doll et al.
2005/0063575 A1 3/2005 Ma et al.
2005/0065438 A1 3/2005 Miller
2005/0131390 A1 6/2005 Heinrich et al.
2005/0143759 A1 6/2005 Kelly
2005/0149001 A1 7/2005 Uchikubo et al.
2005/0149356 A1 7/2005 Cyr et al.
2005/0192633 A1 9/2005 Montpetit
2005/0222631 A1 10/2005 Dalal et al.
2005/0236474 A1 10/2005 Onuma et al.
2005/0277913 A1 12/2005 McCary
2006/0020272 A1 1/2006 Gildenberg
2006/0025816 A1 2/2006 Shelton
2006/0059018 A1 3/2006 Shiobara et al.
2006/0079874 A1 4/2006 Faller et al.
2006/0116908 A1 6/2006 Dew et al.
2006/0184160 A1 8/2006 Ozaki et al.
2006/0241399 A1 10/2006 Fabian
2007/0010838 A1 1/2007 Shelton et al.
2007/0016235 A1 1/2007 Tanaka et al.
2007/0027459 A1 2/2007 Horvath et al.
2007/0049947 A1 3/2007 Menn et al.
2007/0078678 A1 4/2007 DiSilvestro et al.
2007/0167702 A1 7/2007 Hasser et al.
2007/0168461 A1 7/2007 Moore
2007/0173803 A1 7/2007 Wham et al.
2007/0175955 A1 8/2007 Shelton et al.
2007/0179482 A1 8/2007 Anderson
2007/0191713 A1 8/2007 Eichmann et al.
2007/0225556 A1 9/2007 Ortiz et al.
2007/0225690 A1 9/2007 Sekiguchi et al.
2007/0244478 A1 10/2007 Bahney
2007/0249990 A1 10/2007 Cosmescu
2007/0270660 A1 11/2007 Caylor et al.
2007/0282333 A1 12/2007 Fortson et al.
2007/0293218 A1 12/2007 Meylan et al.
2008/0013460 A1 1/2008 Allen et al.
2008/0015664 A1 1/2008 Podhajsky
2008/0015912 A1 1/2008 Rosenthal et al.
2008/0033404 A1 2/2008 Romoda et al.
2008/0040151 A1 2/2008 Moore
2008/0059658 A1 3/2008 Williams
2008/0077158 A1 3/2008 Halder et al.
2008/0083414 A1 4/2008 Messerges
2008/0177258 A1 7/2008 Govari et al.
2008/0177362 A1 7/2008 Phillips et al.
2008/0200940 A1 8/2008 Eichmann et al.
2008/0255413 A1 10/2008 Zemlok et al.
2008/0262654 A1 10/2008 Omori et al.
2008/0281301 A1 11/2008 DeBoer et al.
2008/0281678 A1 11/2008 Keuls et al.
2008/0296346 A1 12/2008 Shelton, IV et al.
2008/0306759 A1 12/2008 Llkin et al.
2008/0312953 A1 12/2008 Claus
2009/0036750 A1 2/2009 Weinstein et al.
2009/0036794 A1 2/2009 Stubhaug et al.
2009/0043253 A1 2/2009 Podaima
2009/0046146 A1 2/2009 Hoyt
2009/0048589 A1 2/2009 Takashino et al.
2009/0076409 A1 3/2009 Wu et al.
2009/0090763 A1 4/2009 Zemlok et al.
2009/0099866 A1 4/2009 Newman
2009/0182577 A1 7/2009 Squilla et al.
2009/0206131 A1 8/2009 Weisenburgh, II et al.
2009/0217932 A1 9/2009 Voegele
2009/0234352 A1 9/2009 Behnke et al.
2009/0259149 A1 10/2009 Tahara et al.
2009/0259221 A1 10/2009 Tahara et al.
2009/0307681 A1 12/2009 Armado et al.
2009/0326321 A1 12/2009 Jacobsen et al.
2009/0326336 A1 12/2009 Lemke et al.
2010/0065604 A1 3/2010 Weng
2010/0069942 A1 3/2010 Shelton, IV
2010/0070417 A1 3/2010 Flynn et al.
2010/0132334 A1 6/2010 Duclos et al.
2010/0137845 A1 6/2010 Ramstein et al.
2010/0168561 A1 7/2010 Anderson
2010/0179831 A1 7/2010 Brown et al.
2010/0191100 A1 7/2010 Anderson et al.
2010/0198248 A1 8/2010 Vakharia
2010/0217991 A1 8/2010 Choi
2010/0234996 A1 9/2010 Schreiber et al.
2010/0235689 A1 9/2010 Tian et al.
2010/0250571 A1 9/2010 Pierce et al.
2010/0292535 A1 11/2010 Paskar
2010/0292684 A1 11/2010 Cybulski et al.
2011/0022032 A1 1/2011 Zemlok et al.
2011/0071530 A1 3/2011 Carson
2011/0077512 A1 3/2011 Boswell
2011/0087238 A1 4/2011 Wang et al.
2011/0105895 A1 5/2011 Kornblau et al.
2011/0118708 A1 5/2011 Burbank et al.
2011/0119075 A1 5/2011 Dhoble
2011/0125149 A1 5/2011 El-Galley et al.
2011/0152712 A1 6/2011 Cao et al.
2011/0166883 A1 7/2011 Palmer et al.
2011/0237883 A1 9/2011 Chun
2011/0264000 A1 10/2011 Paul et al.
2011/0306840 A1 12/2011 Allen et al.
2012/0022519 A1 1/2012 Huang et al.
2012/0059684 A1 3/2012 Hampapur et al.
2012/0078247 A1 3/2012 Worrell et al.
2012/0080336 A1 4/2012 Shelton, IV et al.
2012/0083786 A1 4/2012 Artale et al.
2012/0116265 A1 5/2012 Houser et al.
2012/0116381 A1 5/2012 Houser et al.
2012/0130217 A1 5/2012 Kauphusman et al.
2012/0145714 A1 6/2012 Farascioni et al.
2012/0172696 A1 7/2012 Kallback et al.
2012/0191091 A1 7/2012 Allen
2012/0191162 A1 7/2012 Villa
2012/0203785 A1 8/2012 Awada
2012/0211542 A1 8/2012 Racenet
2012/0245958 A1 9/2012 Lawrence et al.
2012/0265555 A1 10/2012 Cappuzzo et al.
2012/0292367 A1 11/2012 Morgan et al.
2012/0319859 A1 12/2012 Taub et al.
2013/0024213 A1 1/2013 Poon
2013/0046182 A1 2/2013 Hegg et al.
2013/0046279 A1 2/2013 Niklewski et al.

(56) References Cited

U.S. PATENT DOCUMENTS

2013/0066647 A1 3/2013 Andrie et al.
2013/0090526 A1 4/2013 Suzuki et al.
2013/0093829 A1 4/2013 Rosenblatt et al.
2013/0105552 A1 5/2013 Weir et al.
2013/0116218 A1 5/2013 Kaplan et al.
2013/0165776 A1 6/2013 Blomqvist
2013/0178853 A1 7/2013 Hyink et al.
2013/0206813 A1 8/2013 Nalagatla
2013/0214025 A1 8/2013 Zemlok et al.
2013/0240623 A1* 9/2013 Baym .................... G16H 10/60 235/380
2013/0253480 A1 9/2013 Kimball et al.
2013/0256373 A1 10/2013 Schmid et al.
2013/0267874 A1 10/2013 Marcotte et al.
2013/0277410 A1 10/2013 Fernandez et al.
2013/0317837 A1 11/2013 Ballantyne et al.
2013/0321425 A1 12/2013 Greene et al.
2013/0325809 A1 12/2013 Kim et al.
2013/0331873 A1 12/2013 Ross et al.
2013/0331875 A1 12/2013 Ross et al.
2014/0001231 A1 1/2014 Shelton, IV et al.
2014/0001234 A1 1/2014 Shelton, IV et al.
2014/0005640 A1 1/2014 Shelton, IV et al.
2014/0006132 A1 1/2014 Barker
2014/0006943 A1 1/2014 Robbins et al.
2014/0013565 A1 1/2014 MacDonald et al.
2014/0029411 A1 1/2014 Nayak et al.
2014/0033926 A1 2/2014 Fassel et al.
2014/0035762 A1 2/2014 Shelton, IV et al.
2014/0066700 A1 3/2014 Wilson et al.
2014/0081255 A1 3/2014 Johnson et al.
2014/0081659 A1* 3/2014 Nawana ................. A61B 34/10 705/3
2014/0084949 A1 3/2014 Smith et al.
2014/0087999 A1 3/2014 Kaplan et al.
2014/0092089 A1 4/2014 Kasuya et al.
2014/0107697 A1 4/2014 Patani et al.
2014/0108035 A1 4/2014 Akbay et al.
2014/0108983 A1 4/2014 William R et al.
2014/0148729 A1 5/2014 Schmitz et al.
2014/0166724 A1 6/2014 Schellin et al.
2014/0187856 A1 7/2014 Holoien et al.
2014/0194864 A1 7/2014 Martin et al.
2014/0204190 A1 7/2014 Rosenblatt, III et al.
2014/0243799 A1 8/2014 Parihar
2014/0243809 A1 8/2014 Gelfand et al.
2014/0246475 A1 9/2014 Hall et al.
2014/0249557 A1 9/2014 Koch et al.
2014/0252064 A1 9/2014 Mozdzierz et al.
2014/0263541 A1 9/2014 Leimbach et al.
2014/0263552 A1 9/2014 Hall et al.
2014/0303660 A1 10/2014 Boyden et al.
2015/0006201 A1 1/2015 Fait et al.
2015/0025549 A1 1/2015 Kilroy et al.
2015/0032150 A1 1/2015 Ishida et al.
2015/0051452 A1 2/2015 Ciaccio
2015/0051617 A1 2/2015 Takemura et al.
2015/0053737 A1 2/2015 Leimbach et al.
2015/0066000 A1 3/2015 An et al.
2015/0070187 A1 3/2015 Wiesner et al.
2015/0108198 A1 4/2015 Estrella
2015/0122870 A1 5/2015 Zemlok et al.
2015/0133945 A1 5/2015 Dushyant et al.
2015/0196295 A1 7/2015 Shelton, IV et al.
2015/0199109 A1 7/2015 Lee
2015/0238355 A1 8/2015 Vezzu et al.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0297200 A1 10/2015 Fitzsimmons et al.
2015/0297222 A1 10/2015 Huitema et al.
2015/0297228 A1 10/2015 Huitema et al.
2015/0297233 A1 10/2015 Huitema et al.
2015/0297311 A1 10/2015 Tesar
2015/0302157 A1 10/2015 Collar et al.
2015/0310174 A1 10/2015 Coudert et al.
2015/0313538 A1 11/2015 Bechtel et al.
2015/0317899 A1 11/2015 Dumbauld et al.
2015/0324114 A1 11/2015 Hurley et al.
2015/0332003 A1 11/2015 Stamm et al.
2015/0332196 A1 11/2015 Stiller et al.
2016/0000437 A1 1/2016 Giordano et al.
2016/0015471 A1 1/2016 Piron et al.
2016/0034648 A1 2/2016 Mohlenbrock et al.
2016/0038253 A1 2/2016 Piron et al.
2016/0066913 A1 3/2016 Swayze et al.
2016/0078190 A1 3/2016 Greene et al.
2016/0106516 A1 4/2016 Mesallum
2016/0106934 A1 4/2016 Hiraga et al.
2016/0121143 A1 5/2016 Mumaw et al.
2016/0158468 A1 6/2016 Tang et al.
2016/0180045 A1 6/2016 Syed
2016/0192960 A1 7/2016 Bueno et al.
2016/0206202 A1 7/2016 Frangioni
2016/0224760 A1 8/2016 Petak et al.
2016/0228204 A1 8/2016 Quaid et al.
2016/0235303 A1 8/2016 Fleming et al.
2016/0249910 A1 9/2016 Shelton, IV et al.
2016/0278841 A1 9/2016 Panescu et al.
2016/0287912 A1 10/2016 Warnking
2016/0296246 A1 10/2016 Schaller
2016/0302210 A1 10/2016 Thornton et al.
2016/0310055 A1 10/2016 Zand et al.
2016/0310203 A1 10/2016 Gaspredes et al.
2016/0321400 A1 11/2016 Durrant et al.
2016/0323283 A1 11/2016 Kang et al.
2016/0324537 A1 11/2016 Green et al.
2016/0342753 A1 11/2016 Feazell
2016/0342916 A1 11/2016 Arceneaux et al.
2016/0345857 A1 12/2016 Jensrud et al.
2016/0345976 A1 12/2016 Gonzalez et al.
2016/0350490 A1 12/2016 Martinez et al.
2016/0361070 A1 12/2016 Ardel et al.
2016/0367305 A1 12/2016 Hareland
2016/0374665 A1 12/2016 DiNardo et al.
2016/0374723 A1 12/2016 Frankhouser et al.
2016/0374762 A1 12/2016 Case et al.
2016/0374775 A1 12/2016 Prpa et al.
2017/0000516 A1 1/2017 Stulen et al.
2017/0000553 A1 1/2017 Wiener et al.
2017/0027603 A1 2/2017 Pandey
2017/0068792 A1 3/2017 Reiner
2017/0079730 A1 3/2017 Azizian et al.
2017/0086829 A1 3/2017 Vendely et al.
2017/0086930 A1 3/2017 Thompson et al.
2017/0105754 A1 4/2017 Boudreaux et al.
2017/0116873 A1 4/2017 Lendvay et al.
2017/0127499 A1 5/2017 Unoson et al.
2017/0132374 A1 5/2017 Lee et al.
2017/0132785 A1 5/2017 Wshah et al.
2017/0143284 A1 5/2017 Sehnert et al.
2017/0143442 A1 5/2017 Tesar et al.
2017/0151026 A1 6/2017 Panescu et al.
2017/0156076 A1 6/2017 Eom et al.
2017/0164997 A1 6/2017 Johnson et al.
2017/0165012 A1 6/2017 Chaplin et al.
2017/0172565 A1 6/2017 Heneveld
2017/0172614 A1 6/2017 Scheib et al.
2017/0177807 A1 6/2017 Fabian
2017/0181745 A1 6/2017 Penna et al.
2017/0196583 A1 7/2017 Sugiyama
2017/0196637 A1 7/2017 Shelton, IV et al.
2017/0202591 A1 7/2017 Shelton, IV et al.
2017/0202605 A1 7/2017 Shelton, IV et al.
2017/0202607 A1 7/2017 Shelton, IV et al.
2017/0224332 A1 8/2017 Hunter et al.
2017/0224334 A1 8/2017 Worthington et al.
2017/0224428 A1 8/2017 Kopp
2017/0231627 A1 8/2017 Shelton, IV et al.
2017/0231628 A1 8/2017 Shelton, IV et al.
2017/0245809 A1 8/2017 Ma et al.
2017/0249432 A1 8/2017 Grantcharov
2017/0252095 A1 9/2017 Johnson

(56) References Cited

U.S. PATENT DOCUMENTS

2017/0255751 A1 9/2017 Sanmugalingham
2017/0262604 A1 9/2017 Francois
2017/0265864 A1 9/2017 Hessler et al.
2017/0273715 A1 9/2017 Piron et al.
2017/0281171 A1 10/2017 Shelton, IV et al.
2017/0281173 A1 10/2017 Shelton, IV et al.
2017/0281186 A1 10/2017 Shelton, IV et al.
2017/0281187 A1 10/2017 Shelton, IV et al.
2017/0281189 A1 10/2017 Nalagatla et al.
2017/0290585 A1 10/2017 Shelton, IV et al.
2017/0296169 A1 10/2017 Yates et al.
2017/0296173 A1 10/2017 Shelton, IV et al.
2017/0296177 A1 10/2017 Harris et al.
2017/0296185 A1 10/2017 Swensgard et al.
2017/0296213 A1 10/2017 Swensgard et al.
2017/0303984 A1 10/2017 Malackowski
2017/0304020 A1 10/2017 Ng et al.
2017/0312456 A1 11/2017 Phillips
2017/0325876 A1 11/2017 Nakadate et al.
2017/0325878 A1 11/2017 Messerly et al.
2017/0360439 A1 12/2017 Chen et al.
2017/0360499 A1 12/2017 Greep et al.
2017/0367583 A1 12/2017 Black et al.
2017/0367695 A1 12/2017 Shelton, IV et al.
2017/0367697 A1 12/2017 Shelton, IV et al.
2017/0367754 A1 12/2017 Narisawa
2017/0367771 A1 12/2017 Tako et al.
2017/0367772 A1 12/2017 Gunn et al.
2017/0370710 A1 12/2017 Chen et al.
2018/0008359 A1 1/2018 Randle
2018/0011983 A1 1/2018 Zuhars et al.
2018/0014848 A1 1/2018 Messerly et al.
2018/0049817 A1 2/2018 Swayze et al.
2018/0050196 A1 2/2018 Pawsey et al.
2018/0055529 A1 3/2018 Messerly et al.
2018/0065248 A1 3/2018 Barral et al.
2018/0078170 A1 3/2018 Panescu et al.
2018/0092706 A1 4/2018 Anderson et al.
2018/0098816 A1 4/2018 Govari et al.
2018/0110523 A1 4/2018 Shelton, IV
2018/0116662 A1 5/2018 Shelton, IV et al.
2018/0116735 A1 5/2018 Tierney et al.
2018/0122506 A1 5/2018 Grantcharov et al.
2018/0125590 A1 5/2018 Giordano et al.
2018/0132895 A1 5/2018 Silver
2018/0144243 A1 5/2018 Hsieh et al.
2018/0153574 A1 6/2018 Faller et al.
2018/0153628 A1 6/2018 Grover et al.
2018/0153632 A1 6/2018 Tokarchuk et al.
2018/0154297 A1 6/2018 Maletich et al.
2018/0161716 A1 6/2018 Li et al.
2018/0168575 A1 6/2018 Simms et al.
2018/0168577 A1 6/2018 Aronhalt et al.
2018/0168578 A1 6/2018 Aronhalt et al.
2018/0168579 A1 6/2018 Aronhalt et al.
2018/0168584 A1 6/2018 Harris et al.
2018/0168586 A1 6/2018 Shelton, IV et al.
2018/0168589 A1 6/2018 Swayze et al.
2018/0168590 A1 6/2018 Overmyer et al.
2018/0168592 A1 6/2018 Overmyer et al.
2018/0168593 A1 6/2018 Overmyer et al.
2018/0168597 A1 6/2018 Fanelli et al.
2018/0168598 A1 6/2018 Shelton, IV et al.
2018/0168601 A1 6/2018 Bakos et al.
2018/0168603 A1 6/2018 Morgan et al.
2018/0168605 A1 6/2018 Baber et al.
2018/0168607 A1 6/2018 Shelton, IV et al.
2018/0168608 A1 6/2018 Shelton, IV et al.
2018/0168609 A1 6/2018 Fanelli et al.
2018/0168610 A1 6/2018 Shelton, IV et al.
2018/0168614 A1 6/2018 Shelton, IV et al.
2018/0168615 A1 6/2018 Shelton, IV et al.
2018/0168616 A1 6/2018 Shelton, IV et al.
2018/0168617 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168627 A1 6/2018 Weaner et al.
2018/0168628 A1 6/2018 Hunter et al.
2018/0168629 A1 6/2018 Shelton, IV et al.
2018/0168632 A1 6/2018 Harris et al.
2018/0168633 A1 6/2018 Shelton, IV et al.
2018/0168639 A1 6/2018 Shelton, IV et al.
2018/0168647 A1 6/2018 Shelton, IV et al.
2018/0168648 A1 6/2018 Shelton, IV et al.
2018/0168649 A1 6/2018 Shelton, IV et al.
2018/0168650 A1 6/2018 Shelton, IV et al.
2018/0168651 A1 6/2018 Shelton, IV et al.
2018/0177383 A1 6/2018 Noonan et al.
2018/0177557 A1 6/2018 Kapadia et al.
2018/0199995 A1 7/2018 Odermatt et al.
2018/0206884 A1 7/2018 Beaupre
2018/0206905 A1 7/2018 Batchelor et al.
2018/0214025 A1 8/2018 Homyk et al.
2018/0221598 A1 8/2018 Silver
2018/0228557 A1 8/2018 Darisse et al.
2018/0233222 A1 8/2018 Daley et al.
2018/0235719 A1 8/2018 Jarc
2018/0242967 A1 8/2018 Meade
2018/0250080 A1 9/2018 Kopp
2018/0250084 A1 9/2018 Kopp et al.
2018/0263710 A1 9/2018 Sakaguchi et al.
2018/0263717 A1 9/2018 Kopp
2018/0268320 A1 9/2018 Shekhar
2018/0271520 A1 9/2018 Shelton, IV et al.
2018/0271603 A1 9/2018 Nir et al.
2018/0296286 A1 10/2018 Peine et al.
2018/0303552 A1 10/2018 Ryan et al.
2018/0304471 A1 10/2018 Tokuchi
2018/0310935 A1 11/2018 Wixey
2018/0310986 A1 11/2018 Batchelor et al.
2018/0310997 A1 11/2018 Peine et al.
2018/0317826 A1 11/2018 Muhsin et al.
2018/0317915 A1 11/2018 McDonald, II
2018/0338806 A1 11/2018 Grubbs
2018/0351987 A1 12/2018 Patel et al.
2018/0358112 A1 12/2018 Sharifi Sedeh et al.
2018/0360449 A1 12/2018 Shelton, IV et al.
2018/0360452 A1 12/2018 Shelton, IV et al.
2018/0360454 A1 12/2018 Shelton, IV et al.
2018/0360456 A1 12/2018 Shelton, IV et al.
2018/0368930 A1 12/2018 Esterberg et al.
2018/0369511 A1 12/2018 Zergiebel et al.
2019/0000446 A1 1/2019 Shelton, IV et al.
2019/0000448 A1 1/2019 Shelton, IV et al.
2019/0000478 A1 1/2019 Messerly et al.
2019/0000530 A1 1/2019 Yates et al.
2019/0000565 A1 1/2019 Shelton, IV et al.
2019/0000569 A1 1/2019 Crawford et al.
2019/0001079 A1 1/2019 Zergiebel et al.
2019/0005641 A1 1/2019 Yamamoto
2019/0006047 A1 1/2019 Gorek et al.
2019/0008600 A1 1/2019 Pedros et al.
2019/0025040 A1 1/2019 Andreason et al.
2019/0029712 A1 1/2019 Stoddard et al.
2019/0036688 A1 1/2019 Wasily et al.
2019/0038335 A1 2/2019 Mohr et al.
2019/0038364 A1 2/2019 Enoki
2019/0053801 A1 2/2019 Wixey et al.
2019/0053866 A1 2/2019 Seow et al.
2019/0069949 A1 3/2019 Vrba et al.
2019/0069962 A1 3/2019 Tabandeh et al.
2019/0069964 A1 3/2019 Hagn
2019/0070550 A1 3/2019 Lalomia et al.
2019/0070731 A1 3/2019 Bowling et al.
2019/0087544 A1 3/2019 Peterson
2019/0090969 A1 3/2019 Jarc et al.
2019/0099227 A1 4/2019 Rockrohr
2019/0104919 A1 4/2019 Shelton, IV et al.
2019/0110828 A1 4/2019 Despatie
2019/0115108 A1 4/2019 Hegedus et al.
2019/0125320 A1 5/2019 Shelton, IV et al.
2019/0125321 A1 5/2019 Shelton, IV et al.

(56) References Cited

U.S. PATENT DOCUMENTS

2019/0125324 A1 5/2019 Scheib et al.
2019/0125335 A1 5/2019 Shelton, IV et al.
2019/0125336 A1 5/2019 Deck et al.
2019/0125337 A1 5/2019 Shelton, IV et al.
2019/0125338 A1 5/2019 Shelton, IV et al.
2019/0125339 A1 5/2019 Shelton, IV et al.
2019/0125344 A1 5/2019 DiNardo et al.
2019/0125347 A1 5/2019 Stokes et al.
2019/0125348 A1 5/2019 Shelton, IV et al.
2019/0125352 A1 5/2019 Shelton, IV et al.
2019/0125353 A1 5/2019 Shelton, IV et al.
2019/0125354 A1 5/2019 Deck et al.
2019/0125355 A1 5/2019 Shelton, IV et al.
2019/0125356 A1 5/2019 Shelton, IV et al.
2019/0125357 A1 5/2019 Shelton, IV et al.
2019/0125358 A1 5/2019 Shelton, IV et al.
2019/0125359 A1 5/2019 Shelton, IV et al.
2019/0125360 A1 5/2019 Shelton, IV et al.
2019/0125361 A1 5/2019 Shelton, IV et al.
2019/0125377 A1 5/2019 Shelton, IV
2019/0125378 A1 5/2019 Shelton, IV et al.
2019/0125379 A1 5/2019 Shelton, IV et al.
2019/0125380 A1 5/2019 Hunter et al.
2019/0125381 A1 5/2019 Scheib et al.
2019/0125383 A1 5/2019 Scheib et al.
2019/0125384 A1 5/2019 Scheib et al.
2019/0125385 A1 5/2019 Scheib et al.
2019/0125386 A1 5/2019 Shelton, IV et al.
2019/0125387 A1 5/2019 Parihar et al.
2019/0125388 A1 5/2019 Shelton, IV et al.
2019/0125389 A1 5/2019 Shelton, IV et al.
2019/0125390 A1 5/2019 Shelton, IV et al.
2019/0125430 A1 5/2019 Shelton, IV et al.
2019/0125431 A1 5/2019 Shelton, IV et al.
2019/0125432 A1 5/2019 Shelton, IV et al.
2019/0125454 A1 5/2019 Stokes et al.
2019/0125455 A1 5/2019 Shelton, IV et al.
2019/0125456 A1 5/2019 Shelton, IV et al.
2019/0125457 A1 5/2019 Parihar et al.
2019/0125458 A1 5/2019 Shelton, IV et al.
2019/0125459 A1 5/2019 Shelton, IV et al.
2019/0125476 A1 5/2019 Shelton, IV et al.
2019/0133703 A1 5/2019 Seow et al.
2019/0142449 A1 5/2019 Shelton, IV et al.
2019/0142535 A1 5/2019 Seow et al.
2019/0145942 A1 5/2019 Dutriez et al.
2019/0150975 A1 5/2019 Kawasaki et al.
2019/0159777 A1 5/2019 Ehrenfels et al.
2019/0159778 A1 5/2019 Shelton, IV et al.
2019/0162179 A1 5/2019 O'Shea et al.
2019/0164285 A1 5/2019 Nye et al.
2019/0192157 A1 6/2019 Scott et al.
2019/0192236 A1 6/2019 Shelton, IV et al.
2019/0200844 A1 7/2019 Shelton, IV et al.
2019/0200863 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200980 A1 7/2019 Shelton, IV et al.
2019/0200981 A1 7/2019 Harris et al.
2019/0200984 A1 7/2019 Shelton, IV et al.
2019/0200985 A1 7/2019 Shelton, IV et al.
2019/0200986 A1 7/2019 Shelton, IV et al.
2019/0200987 A1 7/2019 Shelton, IV et al.
2019/0200988 A1 7/2019 Shelton, IV
2019/0200996 A1 7/2019 Shelton, IV et al.
2019/0200997 A1 7/2019 Shelton, IV et al.
2019/0200998 A1 7/2019 Shelton, IV et al.
2019/0201020 A1 7/2019 Shelton, IV et al.
2019/0201021 A1 7/2019 Shelton, IV et al.
2019/0201023 A1 7/2019 Shelton, IV et al.
2019/0201024 A1 7/2019 Shelton, IV et al.
2019/0201025 A1 7/2019 Shelton, IV et al.
2019/0201026 A1 7/2019 Shelton, IV et al.
2019/0201027 A1 7/2019 Shelton, IV et al.
2019/0201028 A1 7/2019 Shelton, IV et al.
2019/0201029 A1 7/2019 Shelton, IV et al.
2019/0201030 A1 7/2019 Shelton, IV et al.
2019/0201033 A1 7/2019 Yates et al.
2019/0201034 A1 7/2019 Shelton, IV et al.
2019/0201036 A1 7/2019 Nott et al.
2019/0201037 A1 7/2019 Houser et al.
2019/0201038 A1 7/2019 Yates et al.
2019/0201039 A1 7/2019 Widenhouse et al.
2019/0201040 A1 7/2019 Messerly et al.
2019/0201041 A1 7/2019 Kimball et al.
2019/0201042 A1 7/2019 Nott et al.
2019/0201043 A1 7/2019 Shelton, IV et al.
2019/0201044 A1 7/2019 Shelton, IV et al.
2019/0201045 A1 7/2019 Yates et al.
2019/0201046 A1 7/2019 Shelton, IV et al.
2019/0201047 A1 7/2019 Yates et al.
2019/0201073 A1 7/2019 Nott et al.
2019/0201074 A1 7/2019 Yates et al.
2019/0201075 A1 7/2019 Shelton, IV et al.
2019/0201077 A1 7/2019 Yates et al.
2019/0201079 A1 7/2019 Shelton, IV et al.
2019/0201080 A1 7/2019 Messerly et al.
2019/0201081 A1 7/2019 Shelton, IV et al.
2019/0201082 A1 7/2019 Shelton, IV et al.
2019/0201083 A1 7/2019 Shelton, IV et al.
2019/0201084 A1 7/2019 Shelton, IV et al.
2019/0201085 A1 7/2019 Shelton, IV et al.
2019/0201086 A1 7/2019 Shelton, IV et al.
2019/0201087 A1 7/2019 Shelton, IV et al.
2019/0201088 A1 7/2019 Shelton, IV et al.
2019/0201090 A1 7/2019 Shelton, IV et al.
2019/0201091 A1 7/2019 Yates et al.
2019/0201092 A1 7/2019 Yates et al.
2019/0201102 A1 7/2019 Shelton, IV et al.
2019/0201104 A1 7/2019 Shelton, IV et al.
2019/0201105 A1 7/2019 Shelton, IV et al.
2019/0201111 A1 7/2019 Shelton, IV et al.
2019/0201112 A1 7/2019 Wiener et al.
2019/0201113 A1 7/2019 Shelton, IV et al.
2019/0201114 A1 7/2019 Shelton, IV et al.
2019/0201115 A1 7/2019 Shelton, IV et al.
2019/0201116 A1 7/2019 Shelton, IV et al.
2019/0201117 A1 7/2019 Yates et al.
2019/0201118 A1 7/2019 Shelton, IV et al.
2019/0201119 A1 7/2019 Harris et al.
2019/0201120 A1 7/2019 Shelton, IV et al.
2019/0201123 A1 7/2019 Shelton, IV et al.
2019/0201124 A1 7/2019 Shelton, IV et al.
2019/0201125 A1 7/2019 Shelton, IV et al.
2019/0201126 A1 7/2019 Shelton, IV et al.
2019/0201127 A1 7/2019 Shelton, IV et al.
2019/0201128 A1 7/2019 Yates et al.
2019/0201129 A1 7/2019 Shelton, IV et al.
2019/0201130 A1 7/2019 Shelton, IV et al.
2019/0201135 A1 7/2019 Shelton, IV et al.
2019/0201136 A1 7/2019 Shelton, IV et al.
2019/0201137 A1 7/2019 Shelton, IV et al.
2019/0201138 A1 7/2019 Yates et al.
2019/0201139 A1 7/2019 Shelton, IV et al.
2019/0201140 A1 7/2019 Yates et al.
2019/0201141 A1 7/2019 Shelton, IV et al.
2019/0201142 A1 7/2019 Shelton, IV et al.
2019/0201143 A1 7/2019 Shelton, IV et al.
2019/0201144 A1 7/2019 Shelton, IV et al.
2019/0201145 A1 7/2019 Shelton, IV et al.
2019/0201146 A1 7/2019 Shelton, IV et al.
2019/0201158 A1 7/2019 Shelton, IV et al.
2019/0201159 A1 7/2019 Shelton, IV et al.
2019/0201594 A1 7/2019 Shelton, IV et al.
2019/0201597 A1 7/2019 Shelton, IV et al.
2019/0204201 A1 7/2019 Shelton, IV et al.
2019/0205001 A1 7/2019 Messerly et al.
2019/0205441 A1 7/2019 Shelton, IV et al.
2019/0205566 A1 7/2019 Shelton, IV et al.
2019/0205567 A1 7/2019 Shelton, IV et al.
2019/0206003 A1 7/2019 Harris et al.
2019/0206004 A1 7/2019 Shelton, IV et al.
2019/0206050 A1 7/2019 Yates et al.

(56) References Cited

U.S. PATENT DOCUMENTS

2019/0206216 A1 7/2019 Shelton, IV et al.
2019/0206551 A1 7/2019 Yates et al.
2019/0206555 A1 7/2019 Morgan et al.
2019/0206556 A1 7/2019 Shelton, IV et al.
2019/0206561 A1 7/2019 Shelton, IV et al.
2019/0206562 A1 7/2019 Shelton, IV et al.
2019/0206563 A1 7/2019 Shelton, IV et al.
2019/0206564 A1 7/2019 Shelton, IV et al.
2019/0206565 A1 7/2019 Shelton, IV
2019/0206569 A1 7/2019 Shelton, IV et al.
2019/0206576 A1 7/2019 Shelton, IV et al.
2019/0207773 A1 7/2019 Shelton, IV et al.
2019/0207857 A1 7/2019 Shelton, IV et al.
2019/0207911 A1 7/2019 Wiener et al.
2019/0208641 A1 7/2019 Yates et al.
2019/0254759 A1 8/2019 Azizian
2019/0261984 A1 8/2019 Nelson et al.
2019/0269476 A1 9/2019 Bowling et al.
2019/0272917 A1 9/2019 Couture et al.
2019/0274662 A1 9/2019 Rockman et al.
2019/0274705 A1 9/2019 Sawhney et al.
2019/0274706 A1 9/2019 Nott et al.
2019/0274707 A1 9/2019 Sawhney et al.
2019/0274708 A1 9/2019 Boudreaux
2019/0274709 A1 9/2019 Scoggins
2019/0274710 A1 9/2019 Black
2019/0274711 A1 9/2019 Scoggins et al.
2019/0274712 A1 9/2019 Faller et al.
2019/0274713 A1 9/2019 Scoggins et al.
2019/0274714 A1 9/2019 Cut et al.
2019/0274716 A1 9/2019 Nott et al.
2019/0274717 A1 9/2019 Nott et al.
2019/0274718 A1 9/2019 Denzinger et al.
2019/0274719 A1 9/2019 Stulen
2019/0274720 A1 9/2019 Gee et al.
2019/0274749 A1 9/2019 Brady et al.
2019/0274750 A1 9/2019 Jayme et al.
2019/0274752 A1 9/2019 Denzinger et al.
2019/0290389 A1 9/2019 Kopp
2019/0298340 A1 10/2019 Shelton, IV et al.
2019/0298341 A1 10/2019 Shelton, IV et al.
2019/0298342 A1 10/2019 Shelton, IV et al.
2019/0298343 A1 10/2019 Shelton, IV et al.
2019/0298346 A1 10/2019 Shelton, IV et al.
2019/0298347 A1 10/2019 Shelton, IV et al.
2019/0298350 A1 10/2019 Shelton, IV et al.
2019/0298351 A1 10/2019 Shelton, IV et al.
2019/0298352 A1 10/2019 Shelton, IV et al.
2019/0298353 A1 10/2019 Shelton, IV et al.
2019/0298354 A1 10/2019 Shelton, IV et al.
2019/0298355 A1 10/2019 Shelton, IV et al.
2019/0298356 A1 10/2019 Shelton, IV et al.
2019/0298357 A1 10/2019 Shelton, IV et al.
2019/0298464 A1 10/2019 Abbott
2019/0298481 A1 10/2019 Rosenberg et al.
2019/0307520 A1 10/2019 Peine et al.
2019/0311802 A1 10/2019 Kokubo et al.
2019/0314015 A1 10/2019 Shelton, IV et al.
2019/0314016 A1 10/2019 Huitema et al.
2019/0321117 A1 10/2019 Itkowitz et al.
2019/0333626 A1 10/2019 Mansi et al.
2019/0343594 A1 11/2019 Garcia Kilroy et al.
2019/0374140 A1 12/2019 Tucker et al.
2020/0000470 A1 1/2020 Du et al.
2020/0046353 A1 2/2020 Deck et al.
2020/0054317 A1 2/2020 Pisarnwongs et al.
2020/0054320 A1 2/2020 Harris et al.
2020/0054321 A1 2/2020 Harris et al.
2020/0054322 A1 2/2020 Harris et al.
2020/0054323 A1 2/2020 Harris et al.
2020/0054325 A1 2/2020 Harris et al.
2020/0054326 A1 2/2020 Harris et al.
2020/0054327 A1 2/2020 Harris et al.
2020/0054328 A1 2/2020 Harris et al.
2020/0054329 A1 2/2020 Shelton, IV et al.
2020/0054330 A1 2/2020 Harris et al.
2020/0054331 A1 2/2020 Harris et al.
2020/0078096 A1 3/2020 Barbagli et al.
2020/0100830 A1 4/2020 Henderson et al.
2020/0162896 A1 5/2020 Su et al.
2020/0168323 A1 5/2020 Bullington et al.
2020/0178971 A1 6/2020 Harris et al.
2020/0261075 A1 8/2020 Boudreaux et al.
2020/0261076 A1 8/2020 Boudreaux et al.
2020/0261077 A1 8/2020 Shelton, IV et al.
2020/0261078 A1 8/2020 Bakos et al.
2020/0261080 A1 8/2020 Bakos et al.
2020/0261081 A1 8/2020 Boudreaux et al.
2020/0261082 A1 8/2020 Boudreaux et al.
2020/0261083 A1 8/2020 Bakos et al.
2020/0261084 A1 8/2020 Bakos et al.
2020/0261085 A1 8/2020 Boudreaux et al.
2020/0261086 A1 8/2020 Zeiner et al.
2020/0261087 A1 8/2020 Timm et al.
2020/0261088 A1 8/2020 Harris et al.
2020/0261089 A1 8/2020 Shelton, IV et al.
2020/0275928 A1 9/2020 Shelton, IV et al.
2020/0275930 A1 9/2020 Harris et al.
2020/0281665 A1 9/2020 Kopp
2020/0405375 A1 12/2020 Shelton, IV et al.
2021/0000555 A1 1/2021 Shelton, IV et al.
2021/0007760 A1 1/2021 Reisin
2021/0015568 A1 1/2021 Liao et al.
2021/0022731 A1 1/2021 Eisinger
2021/0022738 A1 1/2021 Weir et al.
2021/0022809 A1 1/2021 Crawford et al.
2021/0059674 A1 3/2021 Shelton, IV et al.
2021/0153889 A1 5/2021 Nott et al.
2021/0169516 A1 6/2021 Houser et al.
2021/0176179 A1 6/2021 Shelton, IV
2021/0177452 A1 6/2021 Nott et al.
2021/0177489 A1 6/2021 Yates et al.

FOREIGN PATENT DOCUMENTS

CN 101617950 A 1/2010
CN 104490448 B 3/2017
CN 206097107 U 4/2017
CN 108652695 A 10/2018
DE 2037167 A1 7/1980
DE 3016131 A1 10/1981
DE 3824913 A1 2/1990
DE 4002843 C1 4/1991
DE 102005051367 A1 4/2007
DE 102016207666 A1 11/2017
EP 0000756 B1 10/1981
EP 1214913 A2 6/2002
EP 2732772 A1 5/2014
EP 2942023 A2 11/2015
EP 3047806 A1 7/2016
EP 3056923 A1 8/2016
EP 3095399 A2 11/2016
EP 3120781 A2 1/2017
EP 3135225 A2 3/2017
EP 3141181 A1 3/2017
FR 2838234 A1 10/2003
GB 2509523 A 7/2014
JP S5373315 A 6/1978
JP 2007123394 A 5/2007
JP 2017513561 A 6/2017
KR 20140104587 A 8/2014
KR 101587721 B1 1/2016
WO WO-9734533 A1 9/1997
WO WO-0024322 A1 5/2000
WO WO-0108578 A1 2/2001
WO WO-0112089 A1 2/2001
WO WO-0120892 A2 3/2001
WO WO-03079909 A2 10/2003
WO WO-2007137304 A2 11/2007
WO WO-2008056618 A2 5/2008
WO WO-2008069816 A1 6/2008
WO WO-2008147555 A2 12/2008
WO WO-2011112931 A1 9/2011
WO WO-2013143573 A1 10/2013

(56) References Cited

FOREIGN PATENT DOCUMENTS

| | | | |
|---|---|---|---|
| WO | WO-2014134196 | A1 | 9/2014 |
| WO | WO-2015129395 | A1 | 9/2015 |
| WO | WO-2016100719 | A1 | 6/2016 |
| WO | WO-2016206015 | A1 | 12/2016 |
| WO | WO-2017011382 | A1 | 1/2017 |
| WO | WO-2017011646 | A1 | 1/2017 |
| WO | WO-2017058695 | A1 | 4/2017 |
| WO | WO-2017151996 | A1 | 9/2017 |
| WO | WO-2017189317 | A1 | 11/2017 |
| WO | WO-2017205308 | A1 | 11/2017 |
| WO | WO-2017210499 | A1 | 12/2017 |
| WO | WO-2017210501 | A1 | 12/2017 |
| WO | WO-2018152141 | A1 | 8/2018 |
| WO | WO-2018176414 | A1 | 10/2018 |

OTHER PUBLICATIONS

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in Iaparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE Ras & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

Jiang, "'Sound of Silence' : a secure indoor wireless ultrasonic communication system," Article, 2014, pp. 46-50, Snapshots of Doctoral Research at University College Cork, School of Engineering—Electrical & Electronic Engineering, UCC, Cork, Ireland.

Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.

Salamon, "AI Detects Polyps Better Than Colonoscopists" Online Article, Jun. 3, 2018, Medscape Medical News, Digestive Disease Week (DDW) 2018: Presentation 133.

Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

Dottorato, "Analysis and Design of the Rectangular Microstrip Patch Antennas for TM0n0 operating mode," Article, Oct. 8, 2010, pp. 1-9, Microwave Journal.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Hsiao-Wei Tang, "ARCM", Video, Sep. 2012, YouTube, 5 screenshots, Retrieved from internet: <https://www.youtube.com/watch?v=UIdQaxb3fRw&feature=youtu.be>.

(56) References Cited

OTHER PUBLICATIONS

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_sur- gical_devices.pdf.
Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
"Surgical instrumentation: the true cost of instrument trays and a potential strategy for optimization"; Mhlaba et al.; Sep. 23, 2015 (Year: 2015).
Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).

* cited by examiner

SURGICAL HUB AND MODULAR DEVICE RESPONSE ADJUSTMENT BASED ON SITUATIONAL AWARENESS

CROSS-REFERENCE TO RELATED APPLICATIONS

The present application claims priority under 35 U.S.C. § 119(e) to U.S. Provisional Patent Application No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION, filed on Sep. 10, 2018, the disclosure of which is herein incorporated by reference in its entirety.

The present application also claims priority under 35 U.S.C. § 119(e) to U.S. Provisional Patent Application No. 62/692,747, titled SMART ACTIVATION OF AN ENERGY DEVICE BY ANOTHER DEVICE, filed on Jun. 30, 2018, to U.S. Provisional Patent Application No. 62/692,748, titled SMART ENERGY ARCHITECTURE, filed on Jun. 30, 2018, and to U.S. Provisional Patent Application No. 62/692,768, titled SMART ENERGY DEVICES, filed on Jun. 30, 2018, the disclosure of each of which is herein incorporated by reference in its entirety.

The present application also claims priority under 35 U.S.C. § 119(e) to U.S. Provisional Patent Application No. 62/659,900, titled METHOD OF HUB COMMUNICATION, filed on Apr. 19, 2018, the disclosure of each of which is herein incorporated by reference in its entirety.

The present application also claims priority under 35 U.S.C. § 119(e) to U.S. Provisional Patent Application No. 62/650,898 filed on Mar. 30, 2018, titled CAPACITIVE COUPLED RETURN PATH PAD WITH SEPARABLE ARRAY ELEMENTS, to U.S. Provisional Patent Application Ser. No. 62/650,887, titled SURGICAL SYSTEMS WITH OPTIMIZED SENSING CAPABILITIES, filed Mar. 30, 2018, to U.S. Provisional Patent Application Ser. No. 62/650,882, titled SMOKE EVACUATION MODULE FOR INTERACTIVE SURGICAL PLATFORM, filed Mar. 30, 2018, and to U.S. Provisional Patent Application Ser. No. 62/650,877, titled SURGICAL SMOKE EVACUATION SENSING AND CONTROLS, filed Mar. 30, 2018, the disclosure of each of which is herein incorporated by reference in its entirety.

The present application also claims priority under 35 U.S.C. § 119(e) to U.S. Provisional Patent Application Ser. No. 62/640,417, titled TEMPERATURE CONTROL IN ULTRASONIC DEVICE AND CONTROL SYSTEM THEREFOR, filed Mar. 8, 2018, and to U.S. Provisional Patent Application Ser. No. 62/640,415, titled ESTIMATING STATE OF ULTRASONIC END EFFECTOR AND CONTROL SYSTEM THEREFOR, filed Mar. 8, 2018, the disclosure of each of which is herein incorporated by reference in its entirety.

The present application also claims priority under 35 U.S.C. § 119(e) to U.S. Provisional Patent Application Ser. No. 62/611,341, titled INTERACTIVE SURGICAL PLATFORM, filed Dec. 28, 2017, to U.S. Provisional Patent Application Ser. No. 62/611,340, titled CLOUD-BASED MEDICAL ANALYTICS, filed Dec. 28, 2017, and to U.S. Provisional Patent Application Ser. No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems. Surgical procedures are typically performed in surgical operating theaters or rooms in a healthcare facility such as, for example, a hospital. A sterile field is typically created around the patient. The sterile field may include the scrubbed team members, who are properly attired, and all furniture and fixtures in the area. Various surgical devices and systems are utilized in performance of a surgical procedure.

Furthermore, in the Digital and Information Age, medical systems and facilities are often slower to implement systems or procedures utilizing newer and improved technologies due to patient safety and a general desire for maintaining traditional practices. However, often times medical systems and facilities may lack communication and shared knowledge with other neighboring or similarly situated facilities as a result. To improve patient practices, it would be desirable to find ways to help interconnect medical systems and facilities better.

SUMMARY

In various embodiments, a surgical system for use in a surgical procedure is disclosed that includes a modular device, at least one data source, and a surgical hub configured to communicably couple to the at least one data source and the modular device. The surgical hub includes a control circuit configured to receive data from the at least one data source. The data is determinative of a progress status the surgical procedure. The control circuit is further configured to adjust a response to a sensed parameter based on the progress status.

In various embodiments, a surgical hub for use in a surgical procedure is disclosed, wherein the surgical hub is configured to communicably couple to at least one data source. The surgical hub includes a control circuit configured to receive data from the at least one data source. The data is determinative of a progress status the surgical procedure. The control circuit is further configured to adjust a response to a sensed parameter based on the progress status.

In various embodiments, a surgical hub for use in a surgical procedure is disclosed, wherein the surgical hub is configured to communicably couple to at least one data source. The surgical hub includes a control circuit configured to receive data from the at least one data source. The data is determinative of a situational parameter of the surgical procedure. The control circuit is further configured to adjust a response to a sensed parameter based on the determined situational parameter.

DRAWINGS

The various aspects described herein, both as to organization and methods of operation, together with further objects and advantages thereof, may best be understood by reference to the following description, taken in conjunction with the accompanying drawings as follows.

Figure 23:
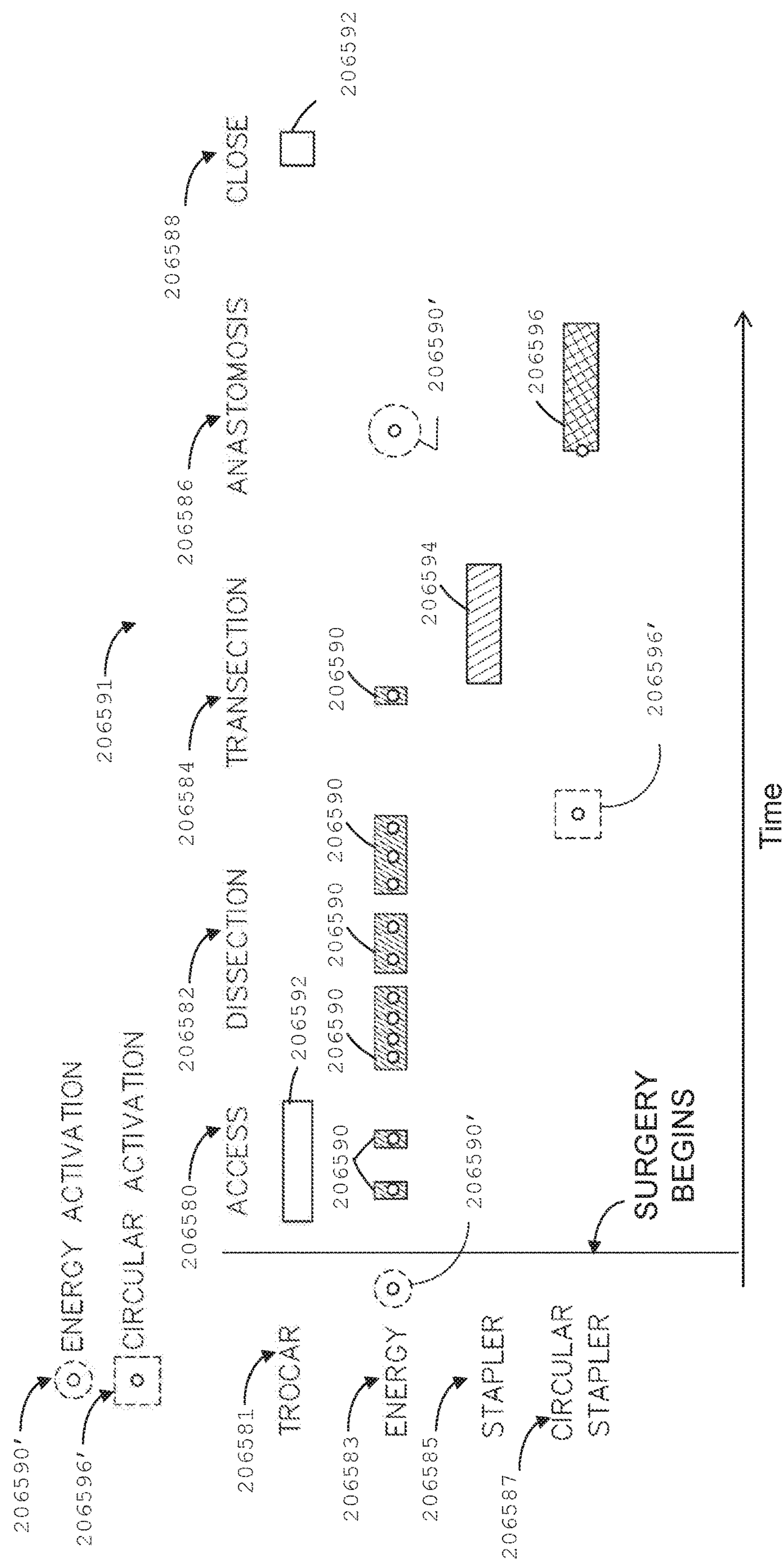

FIG. 23 also depicts various examples of responding to sensed parameters based on a determined situational parameter, in accordance with at least one aspect of the present disclosure.

Figure 24:
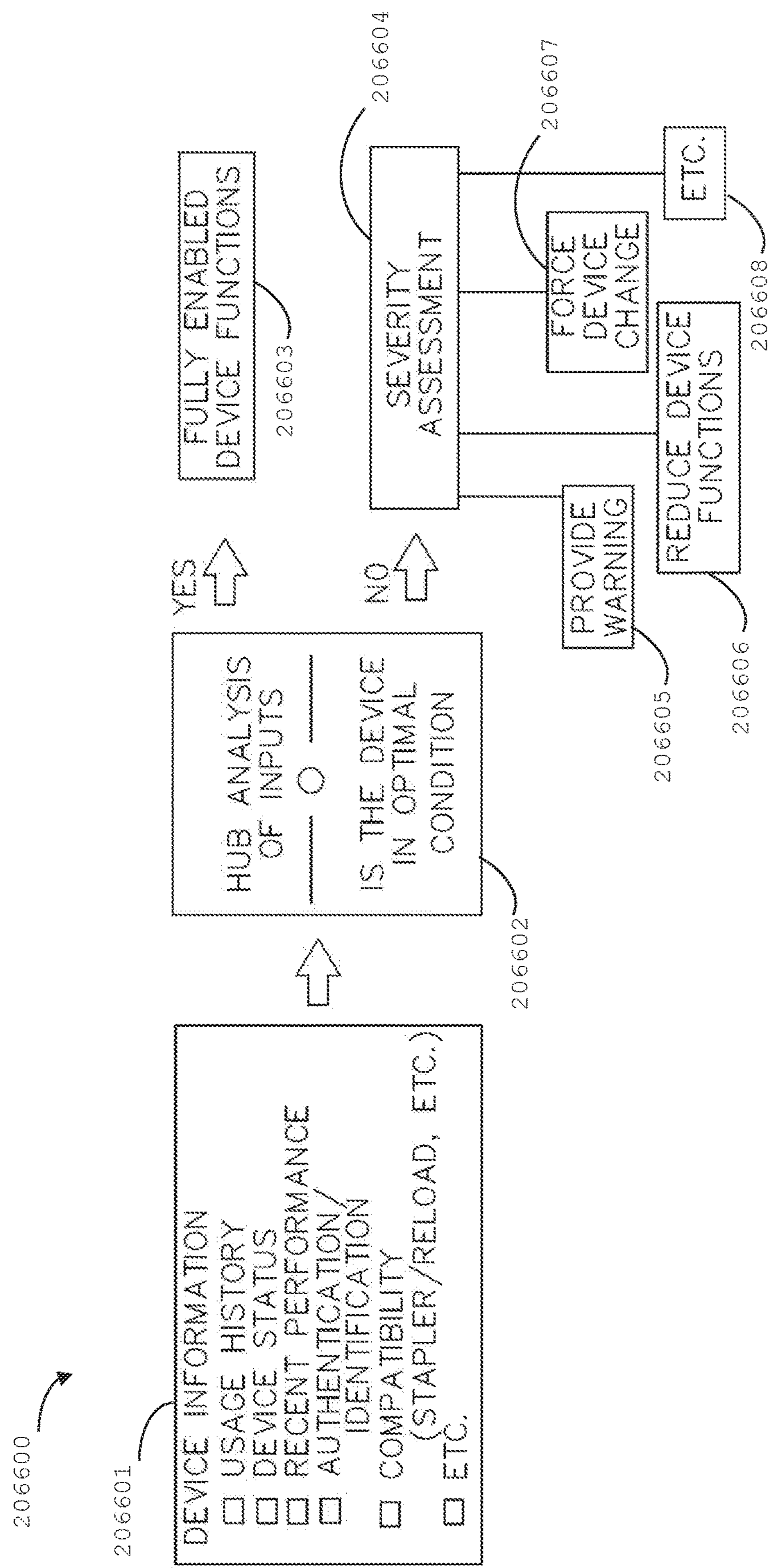

FIG. 24 is a logic flow diagram of a process depicting a control program or a logic configuration for assessing operational fitness of a modular device, in accordance with at least one aspect of the present disclosure.

Figure 25:
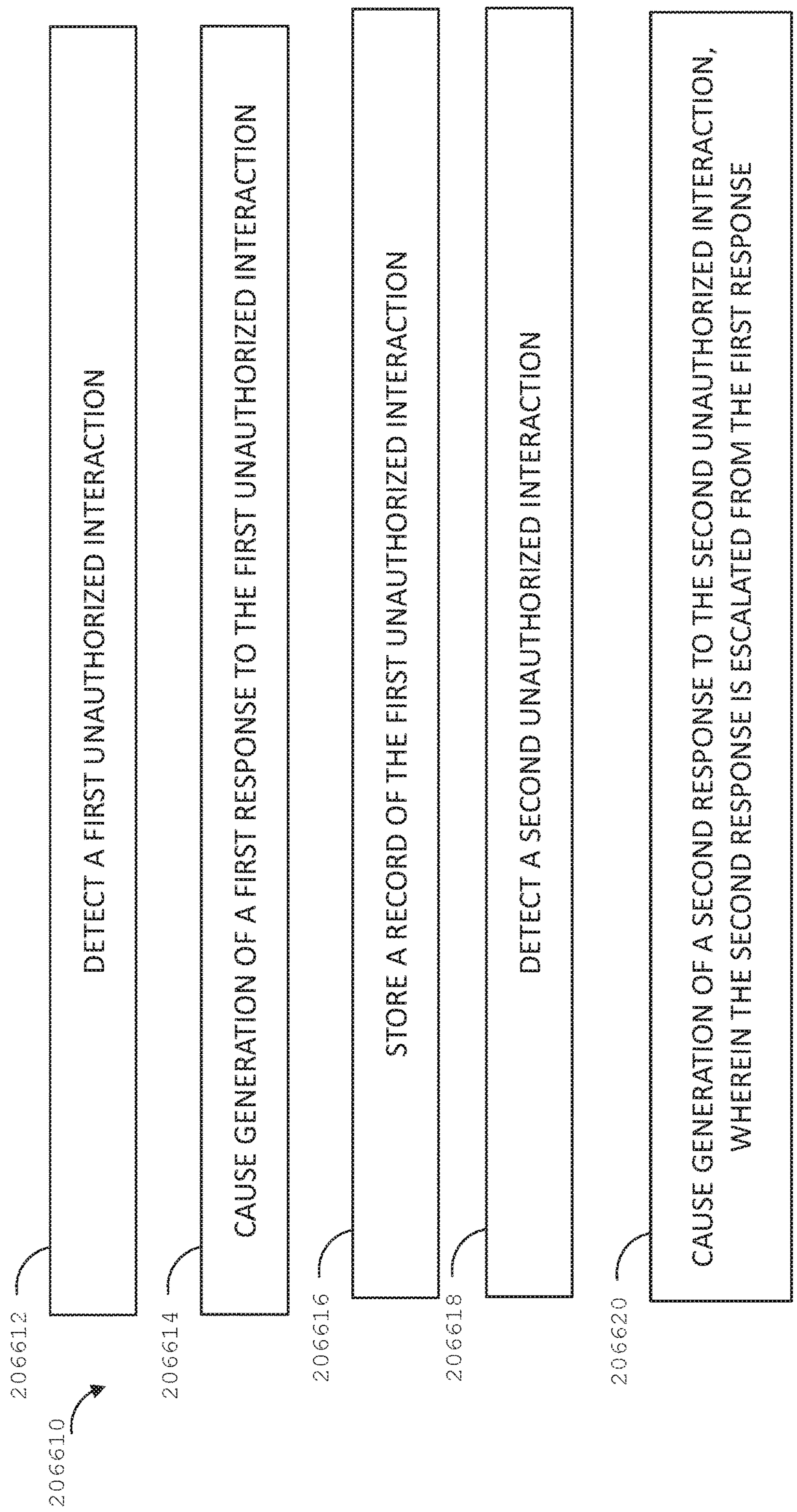

FIG. 25 is a logic flow diagram of a process depicting a control program or a logic configuration for generating suitable responses to unauthorized interactions with a modular device, in accordance with at least one aspect of the present disclosure.

Figure 26:
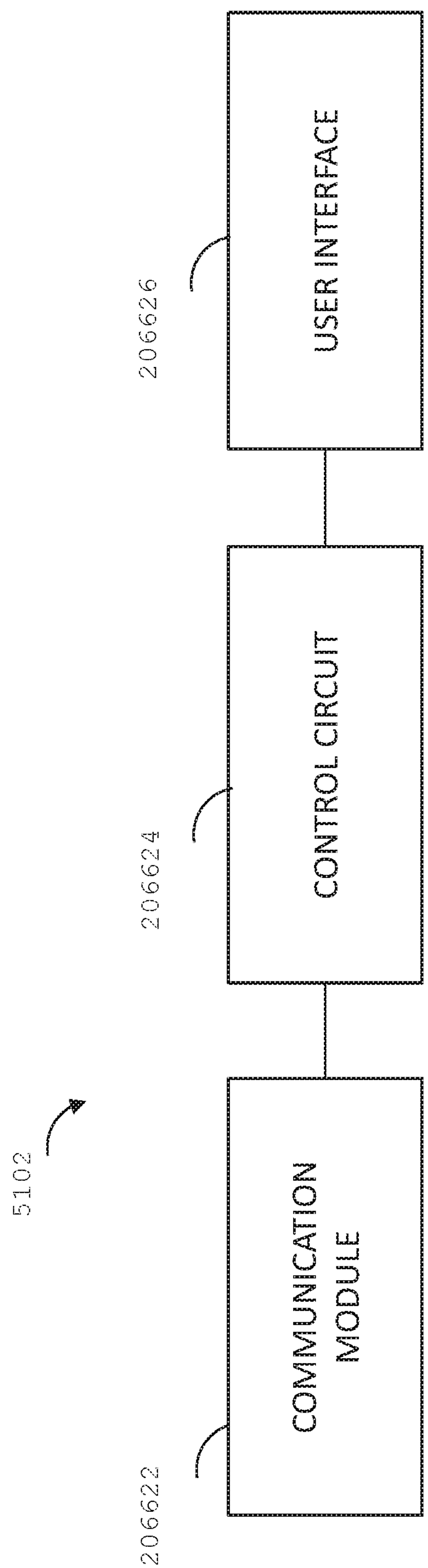

FIG. 26 is schematic diagram illustrating multiple components of a modular device, in accordance with at least one aspect of the present disclosure.

Figure 27:
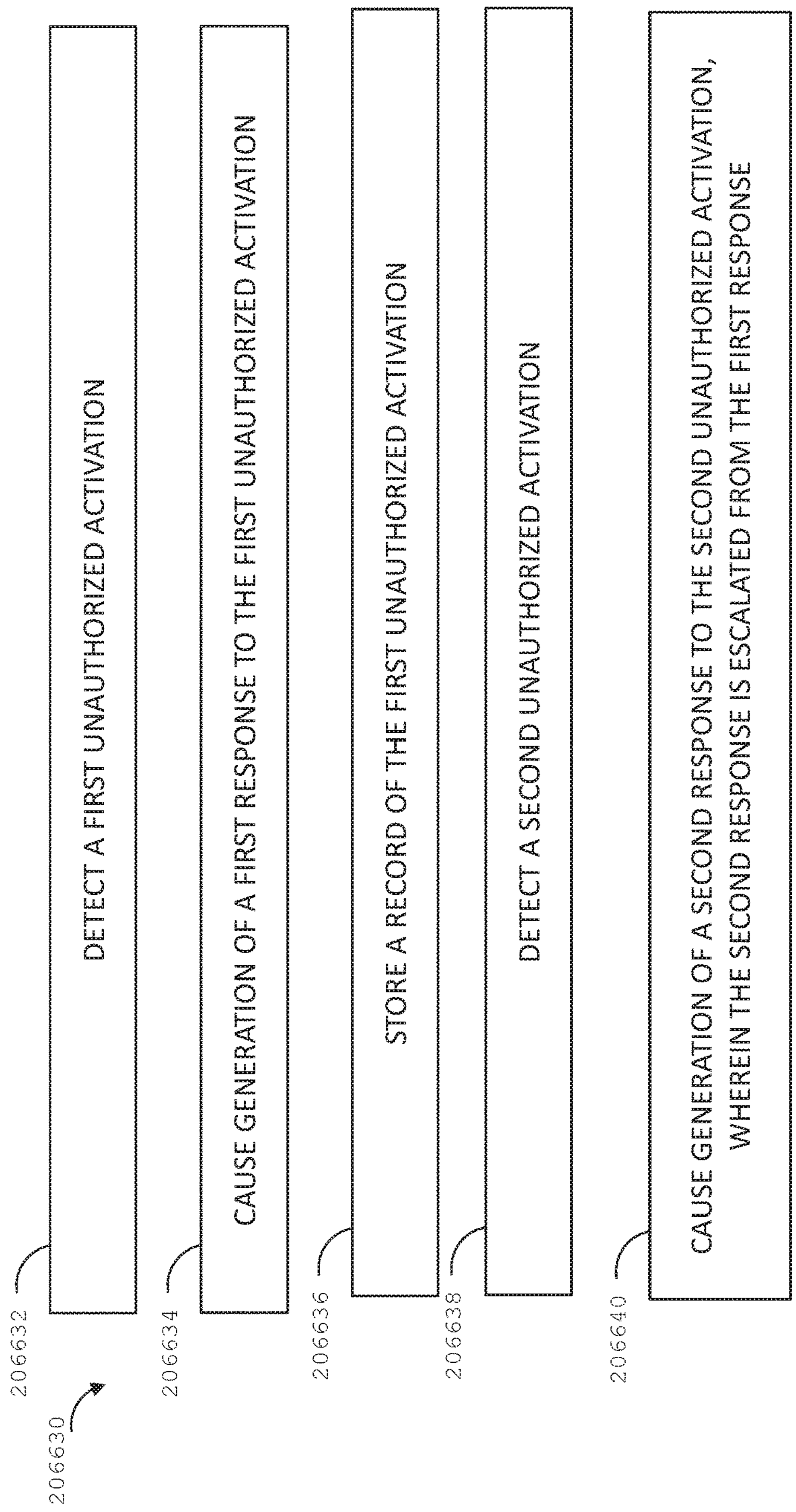

FIG. 27 is a logic flow diagram of a process depicting a control program or a logic configuration for generating suitable responses to unauthorized interactions with a modular device, in accordance with at least one aspect of the present disclosure.

DESCRIPTION

Applicant of the present application owns the following U.S. patent applications, filed on Nov. 6, 2018, the disclosure of each of which is herein incorporated by reference in its entirety:

- U.S. patent application Ser. No. 16/182,224, titled SURGICAL NETWORK, INSTRUMENT, AND CLOUD RESPONSES BASED ON VALIDATION OF RECEIVED DATASET AND AUTHENTICATION OF ITS SOURCE AND INTEGRITY, now U.S. Patent Application Publication No. 2019/0205441;
- U.S. patent application Ser. No. 16/182,230, titled SURGICAL SYSTEM FOR PRESENTING INFORMATION INTERPRETED FROM EXTERNAL DATA, now U.S. Patent Application Publication No. 2019/0200980;
- U.S. patent application Ser. No. 16/182,233, titled MODIFICATION OF SURGICAL SYSTEMS CONTROL PROGRAMS BASED ON MACHINE LEARNING, now U.S. Patent Application Publication No. 2019/0201123;
- U.S. patent application Ser. No. 16/182,239, titled ADJUSTMENT OF DEVICE CONTROL PROGRAMS BASED ON STRATIFIED CONTEXTUAL DATA IN ADDITION TO THE DATA, now U.S. Patent Application Publication No. 2019/0201124;
- U.S. patent application Ser. No. 16/182,248, titled DETECTION AND ESCALATION OF SECURITY RESPONSES OF SURGICAL INSTRUMENTS TO INCREASING SEVERITY THREATS, now U.S. Pat. No. 10,943,454;
- U.S. patent application Ser. No. 16/182,251, titled INTERACTIVE SURGICAL SYSTEM, now U.S. Patent Application Publication No. 2019/0201125;
- U.S. patent application Ser. No. 16/182,260, titled AUTOMATED DATA SCALING, ALIGNMENT, AND ORGANIZING BASED ON PREDEFINED PARAMETERS WITHIN SURGICAL NETWORKS, now U.S. Pat. No. 11,056,244;

U.S. patent application Ser. No. 16/182,267, titled SENSING THE PATIENT POSITION AND CONTACT UTILIZING THE MONO-POLAR RETURN PAD ELECTRODE TO PROVIDE SITUATIONAL AWARENESS TO A SURGICAL NETWORK, now U.S. Patent Application Publication No. 2019/0201128;

U.S. patent application Ser. No. 16/182,249, titled POWERED SURGICAL TOOL WITH PREDEFINED ADJUSTABLE CONTROL ALGORITHM FOR CONTROLLING END EFFECTOR PARAMETER, now U.S. Patent Application Publication No. 2019/0201081;

U.S. patent application Ser. No. 16/182,246, titled ADJUSTMENTS BASED ON AIRBORNE PARTICLE PROPERTIES, now U.S. Patent Application Publication No. 2019/0204201;

U.S. patent application Ser. No. 16/182,256, titled ADJUSTMENT OF A SURGICAL DEVICE FUNCTION BASED ON SITUATIONAL AWARENESS, now U.S. Patent Application Publication No. 2019/0201127;

U.S. patent application Ser. No. 16/182,242, titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES, now U.S. Patent Application Publication No. 2019/0206556;

U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES, now U.S. Patent Application Publication No. 2019/0201126;

U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE, now U.S. Patent Application Publication No. 2019/0201129;

U.S. patent application Ser. No. 16/182,278, titled COMMUNICATION OF DATA WHERE A SURGICAL NETWORK IS USING CONTEXT OF THE DATA AND REQUIREMENTS OF A RECEIVING SYSTEM/USER TO INFLUENCE INCLUSION OR LINKAGE OF DATA AND METADATA TO ESTABLISH CONTINUITY, now U.S. Patent Application Publication No. 2019/0201130;

U.S. patent application Ser. No. 16/182,290, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, now U.S. Patent Application Publication No. 2019/0201102;

U.S. patent application Ser. No. 16/182,232, titled CONTROL OF A SURGICAL SYSTEM THROUGH A SURGICAL BARRIER, now U.S. Patent Application Publication No. 2019/0201158;

U.S. patent application Ser. No. 16/182,227, titled SURGICAL NETWORK DETERMINATION OF PRIORITIZATION OF COMMUNICATION, INTERACTION, OR PROCESSING BASED ON SYSTEM OR DEVICE NEEDS, now U.S. Pat. No. 10,892,995;

U.S. patent application Ser. No. 16/182,231, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, now U.S. Pat. No. 10,758,310;

U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING, now U.S. Pat. No. 11,096,693;

U.S. patent application Ser. No. 16/182,234, titled STAPLING DEVICE WITH BOTH COMPULSORY AND DISCRETIONARY LOCKOUTS BASED ON SENSED PARAMETERS, now U.S. Patent Application Publication No. 2019/0200997;

U.S. patent application Ser. No. 16/182,240, titled POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING, now U.S. Patent Application Publication No. 2019/0201034;

U.S. patent application Ser. No. 16/182,235, titled VARIATION OF RADIO FREQUENCY AND ULTRASONIC POWER LEVEL IN COOPERATION WITH VARYING CLAMP ARM PRESSURE TO ACHIEVE PREDEFINED HEAT FLUX OR POWER APPLIED TO TISSUE, now U.S. Patent Application Publication No. 2019/0201044; and U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, now U.S. Patent Application Publication No. 2019/0201080.

Applicant of the present application owns the following U.S. patent applications, filed on Sep. 10, 2018, the disclosure of each of which is herein incorporated by reference in its entirety:

U.S. Provisional Patent Application No. 62/729,183, titled A CONTROL FOR A SURGICAL NETWORK OR SURGICAL NETWORK CONNECTED DEVICE THAT ADJUSTS ITS FUNCTION BASED ON A SENSED SITUATION OR USAGE;

U.S. Provisional Patent Application No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION;

U.S. Provisional Patent Application No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES;

U.S. Provisional Patent Application No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING;

U.S. Provisional Patent Application No. 62/729,184, titled POWERED SURGICAL TOOL WITH A PREDEFINED ADJUSTABLE CONTROL ALGORITHM FOR CONTROLLING AT LEAST ONE END EFFECTOR PARAMETER AND A MEANS FOR LIMITING THE ADJUSTMENT;

U.S. Provisional Patent Application No. 62/729,182, titled SENSING THE PATIENT POSITION AND CONTACT UTILIZING THE MONO POLAR RETURN PAD ELECTRODE TO PROVIDE SITUATIONAL AWARENESS TO THE HUB;

U.S. Provisional Patent Application No. 62/729,191, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION;

U.S. Provisional Patent Application No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION; and U.S. Provisional Patent Application No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES.

Applicant of the present application owns the following U.S. patent applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR;

U.S. patent application Ser. No. 16/115,205, titled TEMPERATURE CONTROL OF ULTRASONIC END EFFECTOR AND CONTROL SYSTEM THEREFOR;

U.S. patent application Ser. No. 16/115,233, titled RADIO FREQUENCY ENERGY DEVICE FOR DELIVERING COMBINED ELECTRICAL SIGNALS;

U.S. patent application Ser. No. 16/115,208, titled CONTROLLING AN ULTRASONIC SURGICAL INSTRUMENT ACCORDING TO TISSUE LOCATION;

U.S. patent application Ser. No. 16/115,220, titled CONTROLLING ACTIVATION OF AN ULTRASONIC SURGICAL INSTRUMENT ACCORDING TO THE PRESENCE OF TISSUE;

U.S. patent application Ser. No. 16/115,232, titled DETERMINING TISSUE COMPOSITION VIA AN ULTRASONIC SYSTEM;

U.S. patent application Ser. No. 16/115,239, titled DETERMINING THE STATE OF AN ULTRASONIC ELECTROMECHANICAL SYSTEM ACCORDING TO FREQUENCY SHIFT;

U.S. patent application Ser. No. 16/115,247, titled DETERMINING THE STATE OF AN ULTRASONIC END EFFECTOR;

U.S. patent application Ser. No. 16/115,211, titled SITUATIONAL AWARENESS OF ELECTROSURGICAL SYSTEMS;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT;

U.S. patent application Ser. No. 16/115,240, titled DETECTION OF END EFFECTOR IMMERSION IN LIQUID;

U.S. patent application Ser. No. 16/115,249, titled INTERRUPTION OF ENERGY DUE TO INADVERTENT CAPACITIVE COUPLING;

U.S. patent application Ser. No. 16/115,256, titled INCREASING RADIO FREQUENCY TO CREATE PAD-LESS MONOPOLAR LOOP;

U.S. patent application Ser. No. 16/115,223, titled BIPOLAR COMBINATION DEVICE THAT AUTOMATICALLY ADJUSTS PRESSURE BASED ON ENERGY MODALITY; and U.S. patent application Ser. No. 16/115,238, titled ACTIVATION OF ENERGY DEVICES.

Applicant of the present application owns the following U.S. patent applications, filed on Aug. 23, 2018, the disclosure of each of which is herein incorporated by reference in its entirety:

U.S. Provisional Patent Application No. 62/721,995, titled CONTROLLING AN ULTRASONIC SURGICAL INSTRUMENT ACCORDING TO TISSUE LOCATION;

U.S. Provisional Patent Application No. 62/721,998, titled SITUATIONAL AWARENESS OF ELECTROSURGICAL SYSTEMS;

U.S. Provisional Patent Application No. 62/721,999, titled INTERRUPTION OF ENERGY DUE TO INADVERTENT CAPACITIVE COUPLING;

U.S. Provisional Patent Application No. 62/721,994, titled BIPOLAR COMBINATION DEVICE THAT AUTOMATICALLY ADJUSTS PRESSURE BASED ON ENERGY MODALITY; and U.S. Provisional Patent Application No. 62/721,996, titled RADIO FREQUENCY ENERGY DEVICE FOR DELIVERING COMBINED ELECTRICAL SIGNALS.

Applicant of the present application owns the following U.S. patent applications, filed on Jun. 30, 2018, the disclosure of each of which is herein incorporated by reference in its entirety:

U.S. Provisional Patent Application No. 62/692,747, titled SMART ACTIVATION OF AN ENERGY DEVICE BY ANOTHER DEVICE;

U.S. Provisional Patent Application No. 62/692,748, titled SMART ENERGY ARCHITECTURE; and U.S. Provisional Patent Application No. 62/692,768, titled SMART ENERGY DEVICES.

Applicant of the present application owns the following U.S. patent applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS;

U.S. patent application Ser. No. 16/024,057, titled CONTROLLING A SURGICAL INSTRUMENT ACCORDING TO SENSED CLOSURE PARAMETERS;

U.S. patent application Ser. No. 16/024,067, titled SYSTEMS FOR ADJUSTING END EFFECTOR PARAMETERS BASED ON PERIOPERATIVE INFORMATION;

U.S. patent application Ser. No. 16/024,075, titled SAFETY SYSTEMS FOR SMART POWERED SURGICAL STAPLING;

U.S. patent application Ser. No. 16/024,083, titled SAFETY SYSTEMS FOR SMART POWERED SURGICAL STAPLING;

U.S. patent application Ser. No. 16/024,094, titled SURGICAL SYSTEMS FOR DETECTING END EFFECTOR TISSUE DISTRIBUTION IRREGULARITIES;

U.S. patent application Ser. No. 16/024,138, titled SYSTEMS FOR DETECTING PROXIMITY OF SURGICAL END EFFECTOR TO CANCEROUS TISSUE;

U.S. patent application Ser. No. 16/024,150, titled SURGICAL INSTRUMENT CARTRIDGE SENSOR ASSEMBLIES;

U.S. patent application Ser. No. 16/024,160, titled VARIABLE OUTPUT CARTRIDGE SENSOR ASSEMBLY;

U.S. patent application Ser. No. 16/024,124, titled SURGICAL INSTRUMENT HAVING A FLEXIBLE ELECTRODE;

U.S. patent application Ser. No. 16/024,132, titled SURGICAL INSTRUMENT HAVING A FLEXIBLE CIRCUIT;

U.S. patent application Ser. No. 16/024,141, titled SURGICAL INSTRUMENT WITH A TISSUE MARKING ASSEMBLY;

U.S. patent application Ser. No. 16/024,162, titled SURGICAL SYSTEMS WITH PRIORITIZED DATA TRANSMISSION CAPABILITIES;

U.S. patent application Ser. No. 16/024,066, titled SURGICAL EVACUATION SENSING AND MOTOR CONTROL;

U.S. patent application Ser. No. 16/024,096, titled SURGICAL EVACUATION SENSOR ARRANGEMENTS;

U.S. patent application Ser. No. 16/024,116, titled SURGICAL EVACUATION FLOW PATHS;

U.S. patent application Ser. No. 16/024,149, titled SURGICAL EVACUATION SENSING AND GENERATOR CONTROL;

U.S. patent application Ser. No. 16/024,180, titled SURGICAL EVACUATION SENSING AND DISPLAY;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and U.S. patent application Ser. No. 16/024,273, titled DUAL IN-SERIES LARGE AND SMALL DROPLET FILTERS.

Applicant of the present application owns the following U.S. Provisional Patent Applications, filed on Jun. 28, 2018, the disclosure of each of which is herein incorporated by reference in its entirety:

U.S. Provisional Patent Application Ser. No. 62/691,228, titled A METHOD OF USING REINFORCED FLEX CIRCUITS WITH MULTIPLE SENSORS WITH ELECTROSURGICAL DEVICES;

U.S. Provisional Patent Application Ser. No. 62/691,227, titled CONTROLLING A SURGICAL INSTRUMENT ACCORDING TO SENSED CLOSURE PARAMETERS;

U.S. Provisional Patent Application Ser. No. 62/691,230, titled SURGICAL INSTRUMENT HAVING A FLEXIBLE ELECTRODE;

U.S. Provisional Patent Application Ser. No. 62/691,219, titled SURGICAL EVACUATION SENSING AND MOTOR CONTROL;

U.S. Provisional Patent Application Ser. No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. Provisional Patent Application Ser. No. 62/691,262, titled SURGICAL EVACUATION SYSTEM WITH A COMMUNICATION CIRCUIT FOR COMMUNICATION BETWEEN A FILTER AND A SMOKE EVACUATION DEVICE; and U.S. Provisional Patent Application Ser. No. 62/691,251, titled DUAL IN-SERIES LARGE AND SMALL DROPLET FILTERS.

Applicant of the present application owns the following U.S. Provisional Patent Application, filed on Apr. 19, 2018, the disclosure of which is herein incorporated by reference in its entirety:

U.S. Provisional Patent Application Ser. No. 62/659,900, titled METHOD OF HUB COMMUNICATION.

Applicant of the present application owns the following U.S. Provisional Patent Applications, filed on Mar. 30, 2018, the disclosure of each of which is herein incorporated by reference in its entirety:

U.S. Provisional Patent Application No. 62/650,898 filed on Mar. 30, 2018, titled CAPACITIVE COUPLED RETURN PATH PAD WITH SEPARABLE ARRAY ELEMENTS;

U.S. Provisional Patent Application Ser. No. 62/650,887, titled SURGICAL SYSTEMS WITH OPTIMIZED SENSING CAPABILITIES;

U.S. Provisional Patent Application Ser. No. 62/650,882, titled SMOKE EVACUATION MODULE FOR INTERACTIVE SURGICAL PLATFORM; and U.S. Provisional Patent Application Ser. No. 62/650,877, titled SURGICAL SMOKE EVACUATION SENSING AND CONTROLS.

Applicant of the present application owns the following U.S. patent applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES;

U.S. patent application Ser. No. 15/940,648, titled INTERACTIVE SURGICAL SYSTEMS WITH CONDITION HANDLING OF DEVICES AND DATA CAPABILITIES;

U.S. patent application Ser. No. 15/940,656, titled SURGICAL HUB COORDINATION OF CONTROL AND COMMUNICATION OF OPERATING ROOM DEVICES;

U.S. patent application Ser. No. 15/940,666, titled SPATIAL AWARENESS OF SURGICAL HUBS IN OPERATING ROOMS;

U.S. patent application Ser. No. 15/940,670, titled COOPERATIVE UTILIZATION OF DATA DERIVED FROM SECONDARY SOURCES BY INTELLIGENT SURGICAL HUBS;

U.S. patent application Ser. No. 15/940,677, titled SURGICAL HUB CONTROL ARRANGEMENTS;

U.S. patent application Ser. No. 15/940,632, titled DATA STRIPPING METHOD TO INTERROGATE PATIENT RECORDS AND CREATE ANONYMIZED RECORD;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, titled SELF DESCRIBING DATA PACKETS GENERATED AT AN ISSUING INSTRUMENT;

U.S. patent application Ser. No. 15/940,649, titled DATA PAIRING TO INTERCONNECT A DEVICE MEASURED PARAMETER WITH AN OUTCOME;

U.S. patent application Ser. No. 15/940,654, titled SURGICAL HUB SITUATIONAL AWARENESS;

U.S. patent application Ser. No. 15/940,663, titled SURGICAL SYSTEM DISTRIBUTED PROCESSING;

U.S. patent application Ser. No. 15/940,668, titled AGGREGATION AND REPORTING OF SURGICAL HUB DATA;

U.S. patent application Ser. No. 15/940,671, titled SURGICAL HUB SPATIAL AWARENESS TO DETERMINE DEVICES IN OPERATING THEATER;

U.S. patent application Ser. No. 15/940,686, titled DISPLAY OF ALIGNMENT OF STAPLE CARTRIDGE TO PRIOR LINEAR STAPLE LINE;

U.S. patent application Ser. No. 15/940,700, titled STERILE FIELD INTERACTIVE CONTROL DISPLAYS;

U.S. patent application Ser. No. 15/940,629, titled COMPUTER IMPLEMENTED INTERACTIVE SURGICAL SYSTEMS;

U.S. patent application Ser. No. 15/940,704, titled USE OF LASER LIGHT AND RED-GREEN-BLUE COLORATION TO DETERMINE PROPERTIES OF BACK SCATTERED LIGHT;

U.S. patent application Ser. No. 15/940,722, titled CHARACTERIZATION OF TISSUE IRREGULARITIES THROUGH THE USE OF MONO-CHROMATIC LIGHT REFRACTIVITY;

U.S. patent application Ser. No. 15/940,742, titled DUAL CMOS ARRAY IMAGING.

U.S. patent application Ser. No. 15/940,636, titled ADAPTIVE CONTROL PROGRAM UPDATES FOR SURGICAL DEVICES;

U.S. patent application Ser. No. 15/940,653, titled ADAPTIVE CONTROL PROGRAM UPDATES FOR SURGICAL HUBS;

U.S. patent application Ser. No. 15/940,660, titled CLOUD-BASED MEDICAL ANALYTICS FOR CUSTOMIZATION AND RECOMMENDATIONS TO A USER;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, titled CLOUD-BASED MEDICAL ANALYTICS FOR SECURITY AND AUTHENTICATION TRENDS AND REACTIVE MEASURES;

U.S. patent application Ser. No. 15/940,706, titled DATA HANDLING AND PRIORITIZATION IN A CLOUD ANALYTICS NETWORK;

U.S. patent application Ser. No. 15/940,675, titled CLOUD INTERFACE FOR COUPLED SURGICAL DEVICES;

U.S. patent application Ser. No. 15/940,627, titled DRIVE ARRANGEMENTS FOR ROBOT-ASSISTED SURGICAL PLATFORMS;

U.S. patent application Ser. No. 15/940,637, titled COMMUNICATION ARRANGEMENTS FOR ROBOT-ASSISTED SURGICAL PLATFORMS;

U.S. patent application Ser. No. 15/940,642, titled CONTROLS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,680, titled CONTROLLERS FOR ROBOT-ASSISTED SURGICAL PLATFORMS;

U.S. patent application Ser. No. 15/940,683, titled COOPERATIVE SURGICAL ACTIONS FOR ROBOT-ASSISTED SURGICAL PLATFORMS;

U.S. patent application Ser. No. 15/940,690, titled DISPLAY ARRANGEMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Applicant of the present application owns the following U.S. Provisional Patent Applications, filed on Mar. 28, 2018, the disclosure of each of which is herein incorporated by reference in its entirety:

U.S. Provisional Patent Application Ser. No. 62/649,302, titled INTERACTIVE SURGICAL SYSTEMS WITH ENCRYPTED COMMUNICATION CAPABILITIES;

U.S. Provisional Patent Application Ser. No. 62/649,294, titled DATA STRIPPING METHOD TO INTERROGATE PATIENT RECORDS AND CREATE ANONYMIZED RECORD;

U.S. Provisional Patent Application Ser. No. 62/649,300, titled SURGICAL HUB SITUATIONAL AWARENESS;

U.S. Provisional Patent Application Ser. No. 62/649,309, titled SURGICAL HUB SPATIAL AWARENESS TO DETERMINE DEVICES IN OPERATING THEATER;

U.S. Provisional Patent Application Ser. No. 62/649,310, titled COMPUTER IMPLEMENTED INTERACTIVE SURGICAL SYSTEMS;

U.S. Provisional Patent Application Ser. No. 62/649,291, titled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, titled ADAPTIVE CONTROL PROGRAM UPDATES FOR SURGICAL DEVICES;

U.S. Provisional Patent Application Ser. No. 62/649,333, titled CLOUD-BASED MEDICAL ANALYTICS FOR CUSTOMIZATION AND RECOMMENDATIONS TO A USER;

U.S. Provisional Patent Application Ser. No. 62/649,327, titled CLOUD-BASED MEDICAL ANALYTICS FOR SECURITY AND AUTHENTICATION TRENDS AND REACTIVE MEASURES;

U.S. Provisional Patent Application Ser. No. 62/649,315, titled DATA HANDLING AND PRIORITIZATION IN A CLOUD ANALYTICS NETWORK;

U.S. Provisional Patent Application Ser. No. 62/649,313, titled CLOUD INTERFACE FOR COUPLED SURGICAL DEVICES;

U.S. Provisional Patent Application Ser. No. 62/649,320, titled DRIVE ARRANGEMENTS FOR ROBOT-ASSISTED SURGICAL PLATFORMS;

U.S. Provisional Patent Application Ser. No. 62/649,307, titled AUTOMATIC TOOL ADJUSTMENTS FOR ROBOT-ASSISTED SURGICAL PLATFORMS; and U.S. Provisional Patent Application Ser. No. 62/649,323, titled SENSING ARRANGEMENTS FOR ROBOT-ASSISTED SURGICAL PLATFORMS.

Applicant of the present application owns the following U.S. Provisional Patent Applications, filed on Mar. 8, 2018, the disclosure of each of which is herein incorporated by reference in its entirety:

U.S. Provisional Patent Application Ser. No. 62/640,417, titled TEMPERATURE CONTROL IN ULTRASONIC DEVICE AND CONTROL SYSTEM THEREFOR; and U.S. Provisional Patent Application Ser. No. 62/640,415, titled ESTIMATING STATE OF ULTRASONIC END EFFECTOR AND CONTROL SYSTEM THEREFOR.

Applicant of the present application owns the following U.S. Provisional Patent Applications, filed on Dec. 28, 2017, the disclosure of each of which is herein incorporated by reference in its entirety:

U.S. Provisional Patent Application Serial No. U.S. Provisional Patent Application Ser. No. 62/611,341, titled INTERACTIVE SURGICAL PLATFORM;

U.S. Provisional Patent Application Ser. No. 62/611,340, titled CLOUD-BASED MEDICAL ANALYTICS; and U.S. Provisional Patent Application Ser. No. 62/611,339, titled ROBOT ASSISTED SURGICAL PLATFORM.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Surgical Hubs

Figure 1:
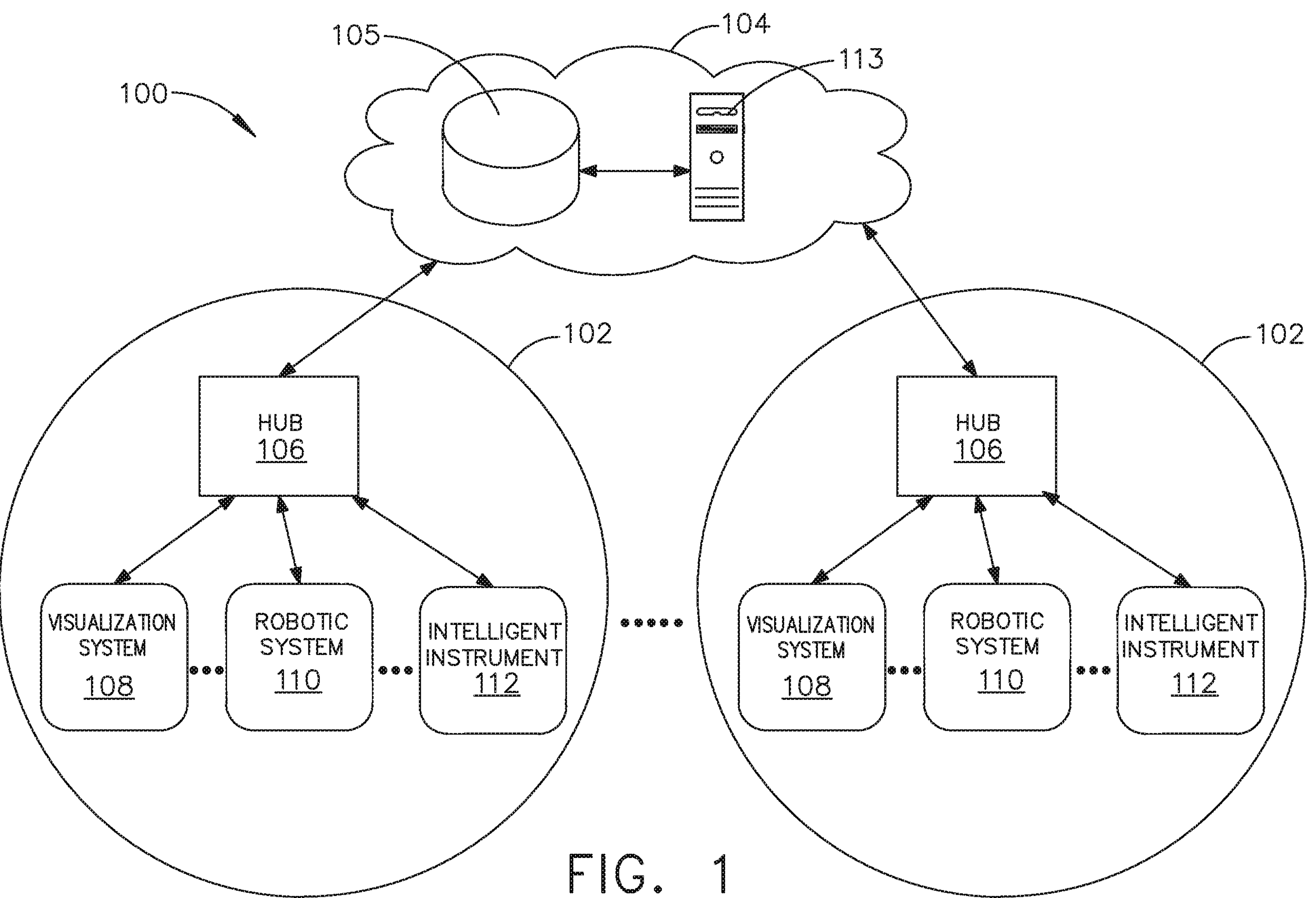
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
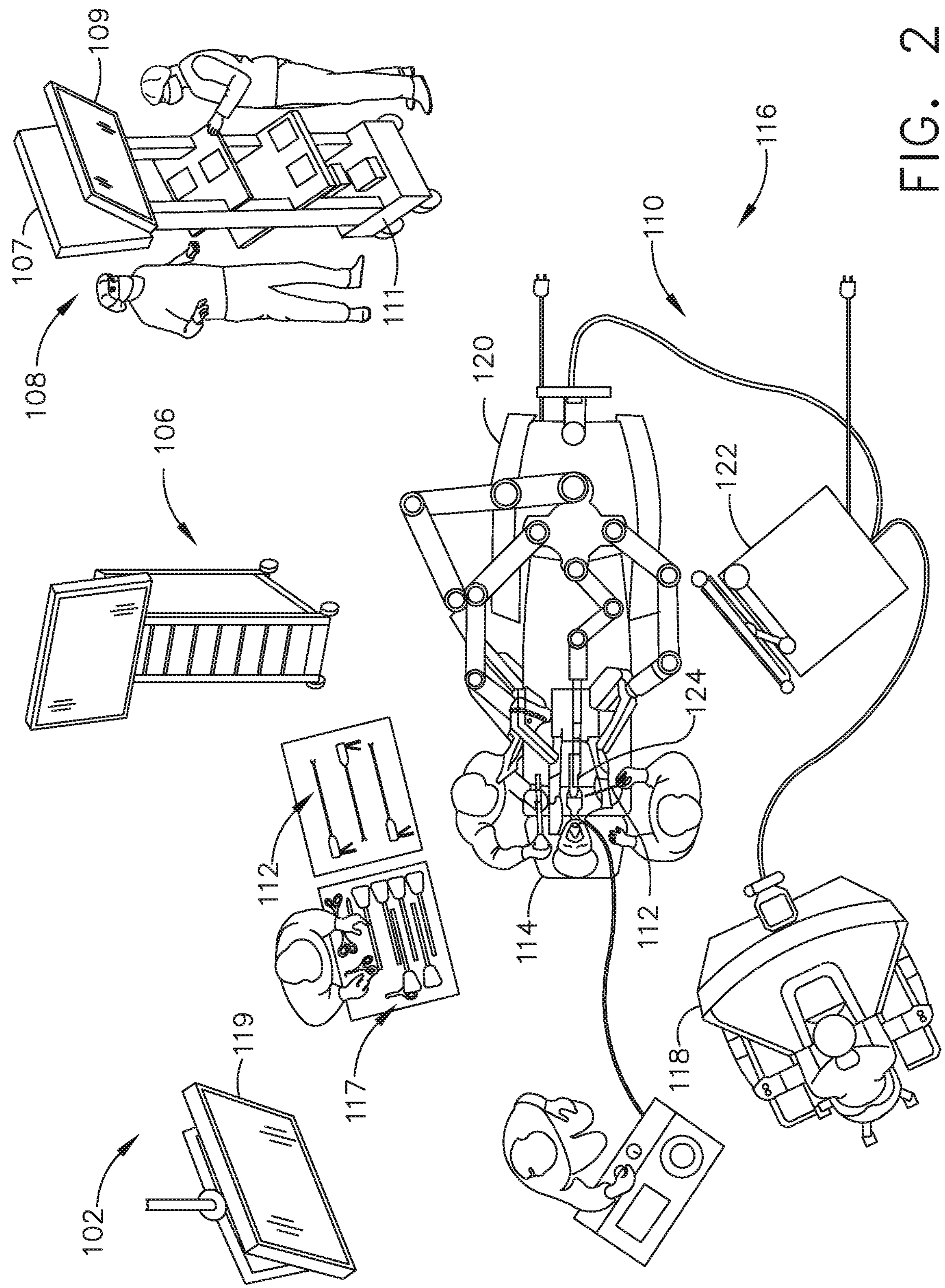
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, coordinate information flow is further described in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
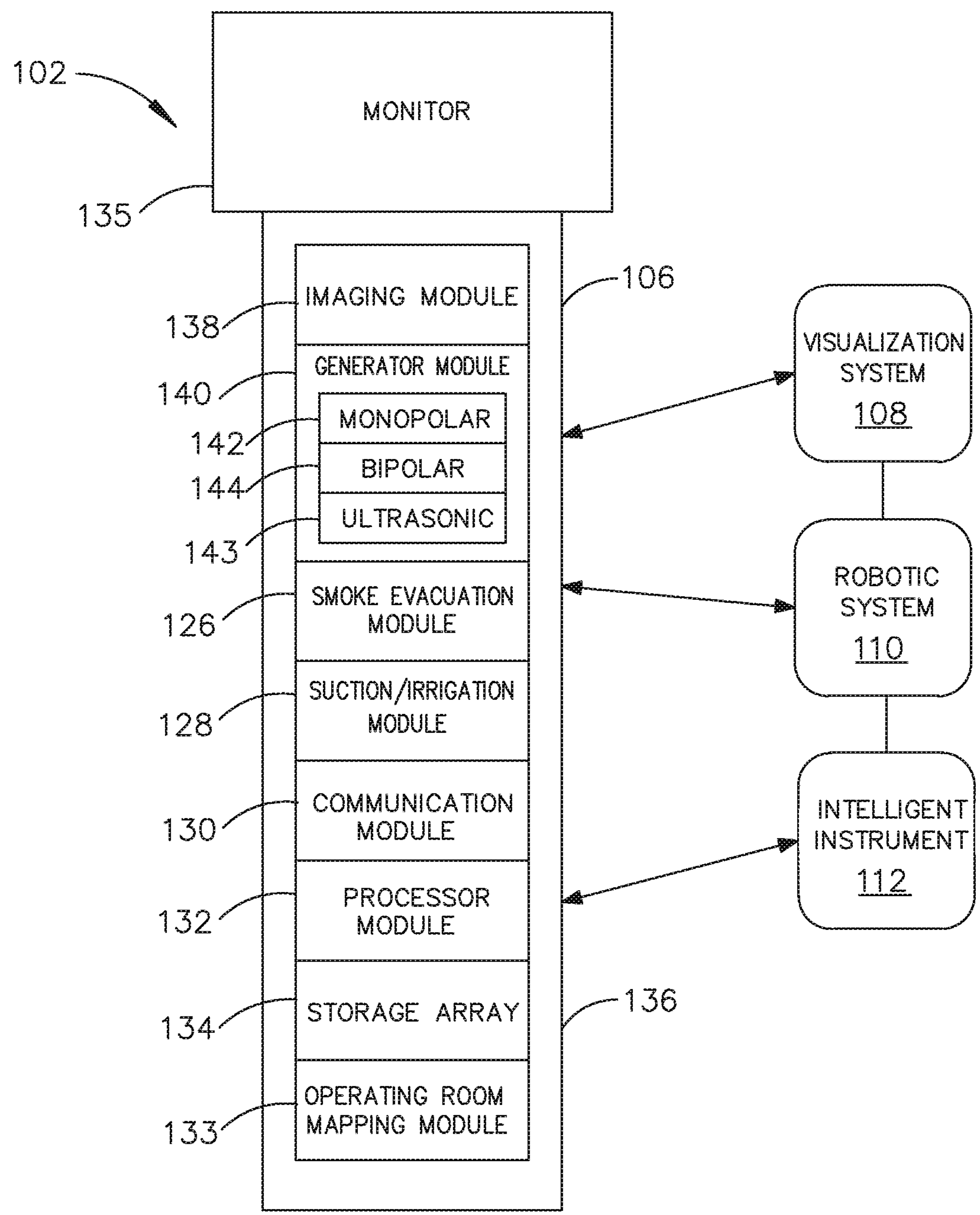
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140 (which can include a monopolar generator 142, a bipolar generator 144, and/or an ultrasonic generator 143), a communication module 130, a processor module 132, and a storage array 134. In certain aspects, as illustrated in FIG. 3, the hub 106 further includes a smoke evacuation module 126, a suction/irrigation module 128, and/or an OR mapping module 133.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
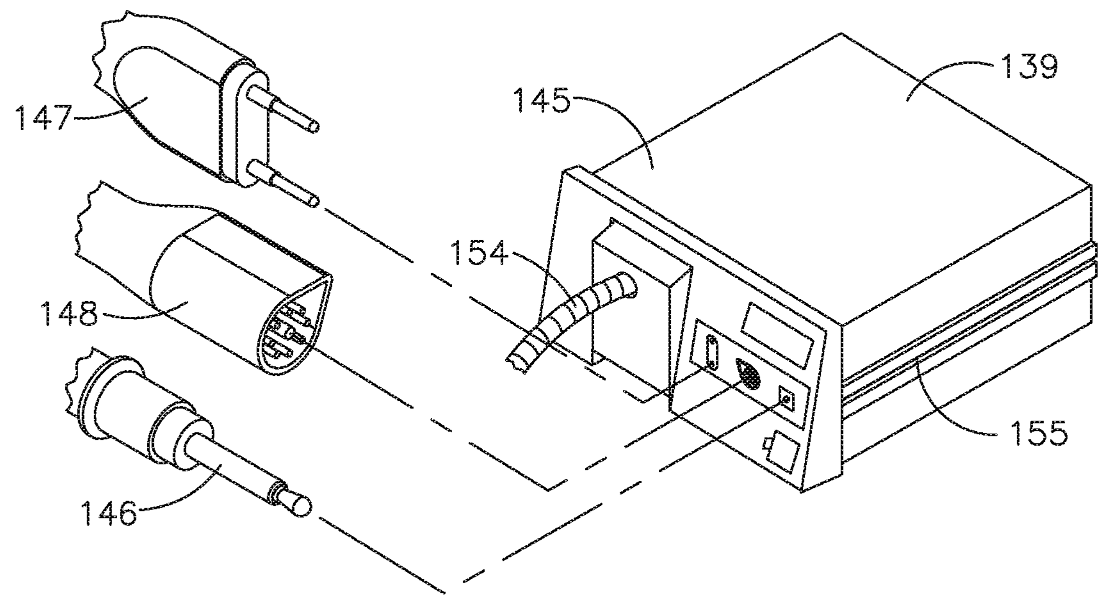
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
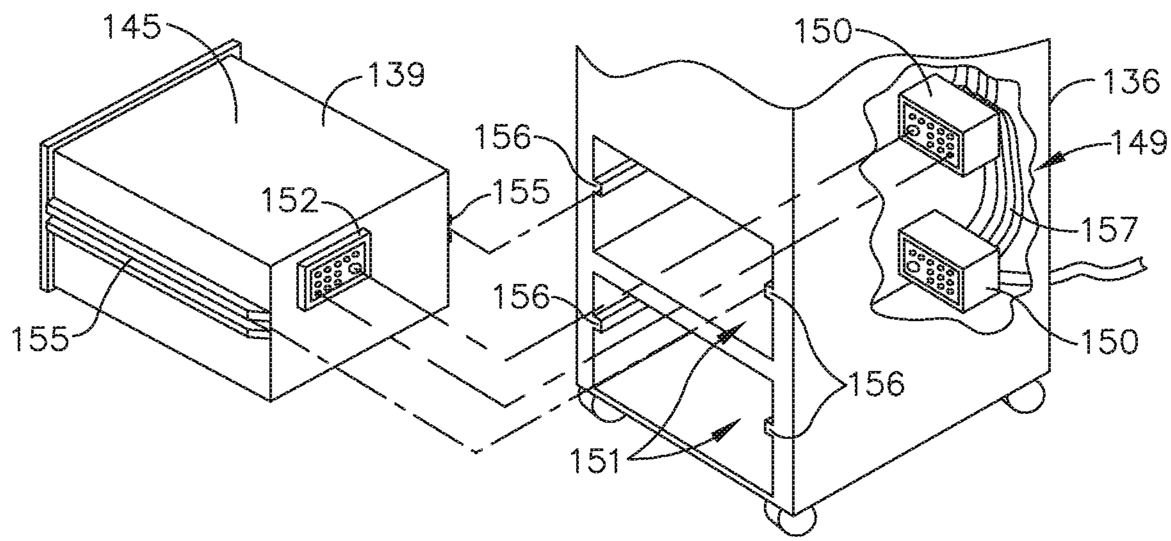
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
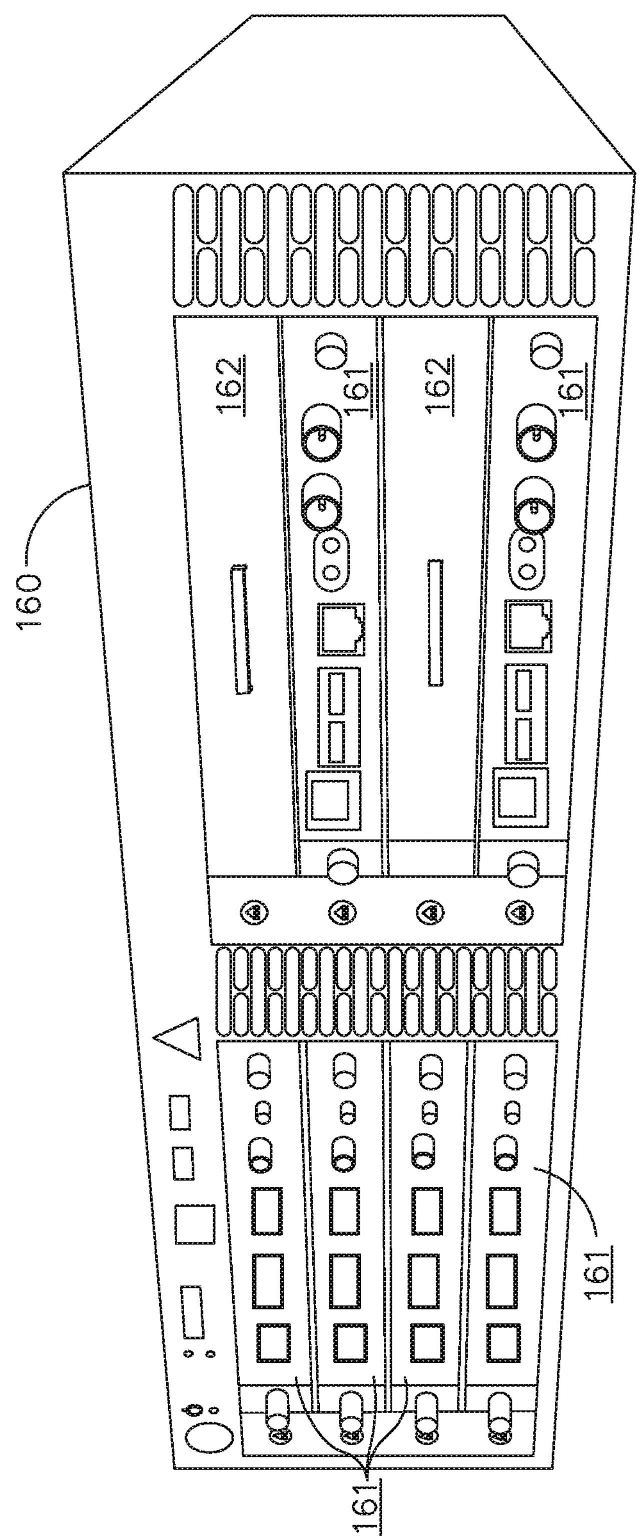
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
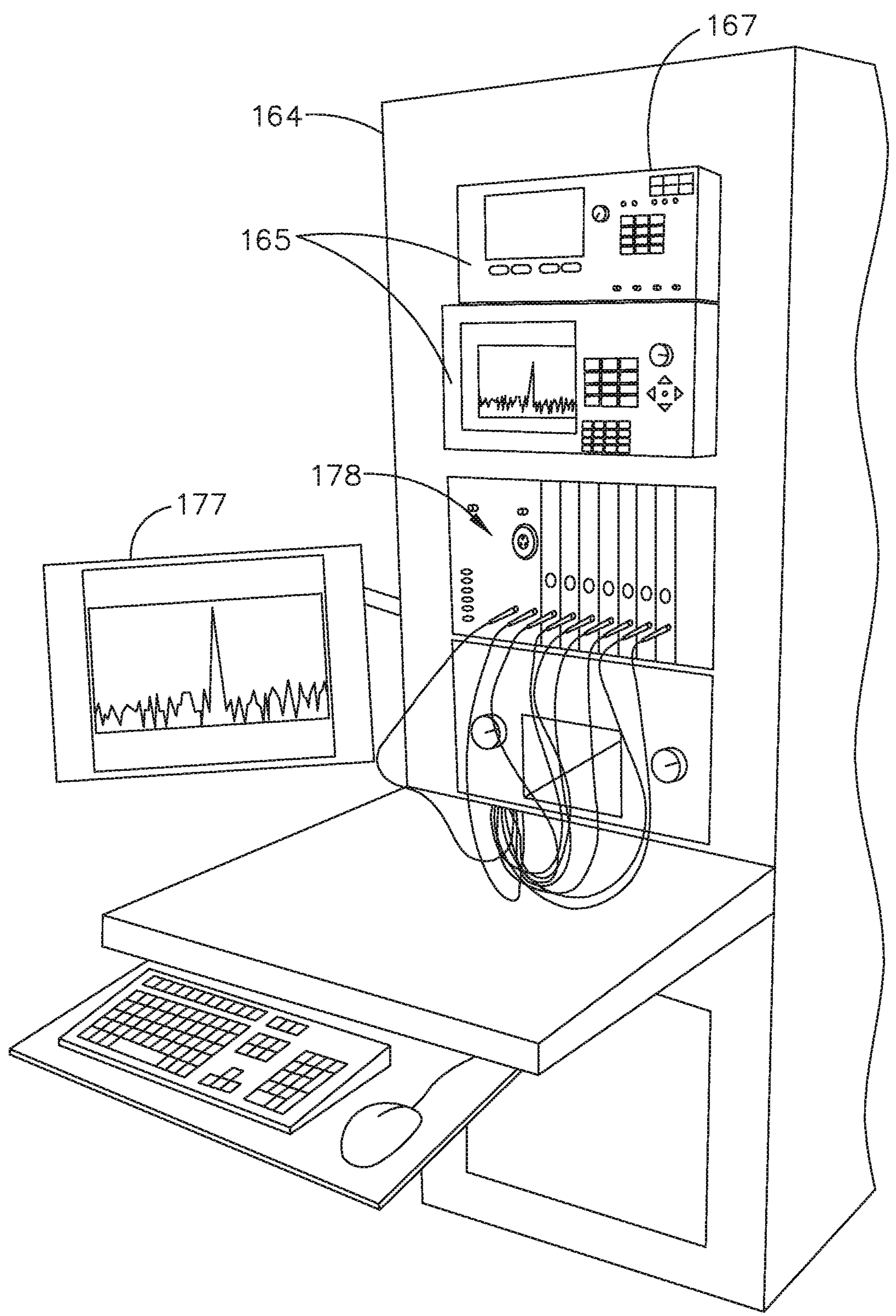
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
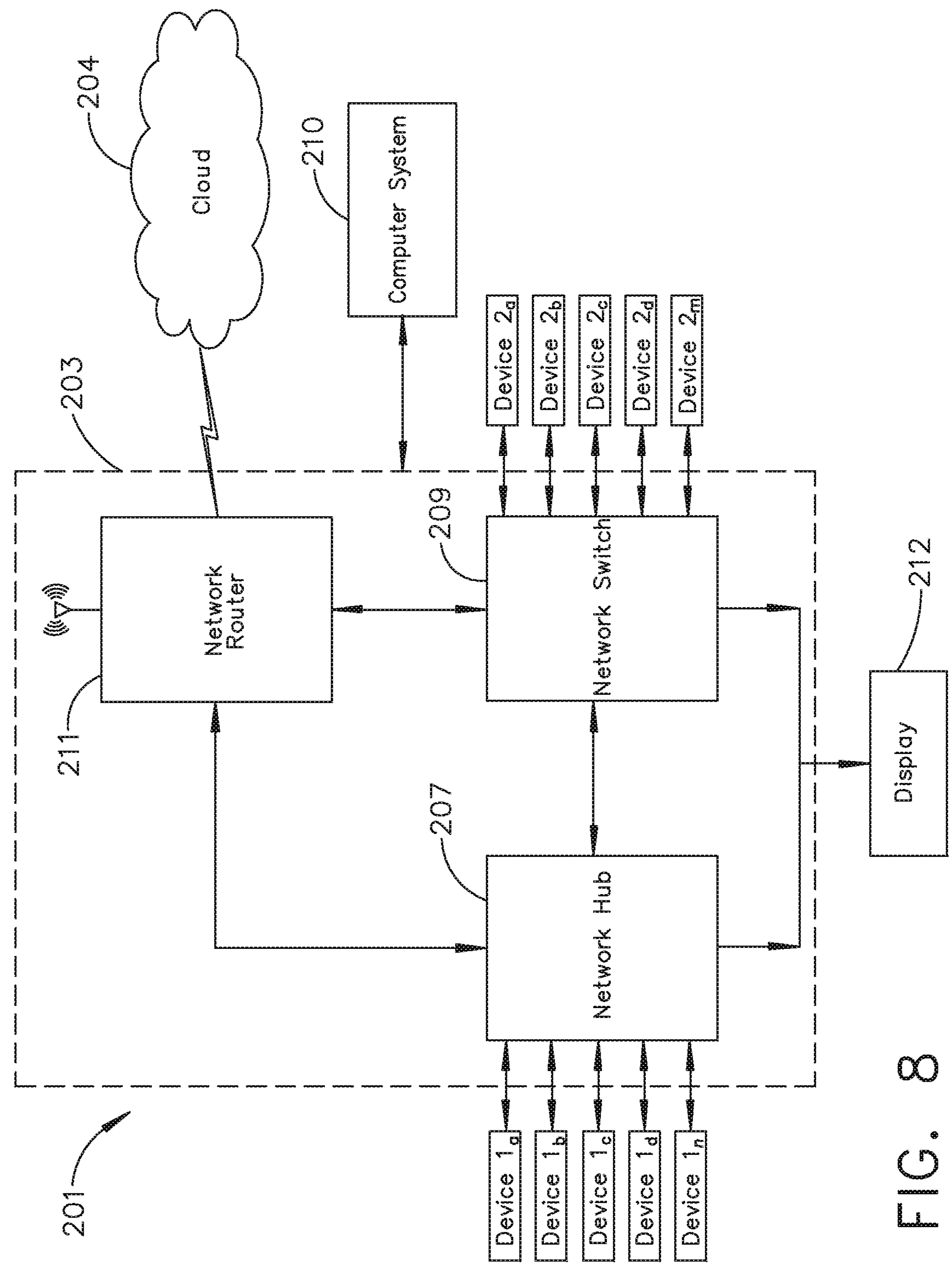
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1*a*-1*n* located in the operating theater may be coupled to the modular communication hub 203. The network hub 207 and/or the network switch 209 may be coupled to a network router 211 to connect the devices 1*a*-1*n* to the cloud 204 or the local computer system 210. Data associated with the devices 1*a*-1*n* may be transferred to cloud-based computers via the router for remote data processing and manipulation. Data associated with the devices 1*a*-1*n* may also be transferred to the local computer system 210 for local data processing and manipulation. Modular devices 2*a*-2*m* located in the same operating theater also may be coupled to a network switch 209. The network switch 209 may be coupled to the network hub 207 and/or the network router 211 to connect to the devices 2*a*-2*m* to the cloud 204. Data associated with the devices 2*a*-2*n* may be transferred to the cloud 204 via the network router 211 for data processing and manipulation. Data associated with the devices 2*a*-2*m* may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1*a*-1*n*/2*a*-2*m*. The local computer system 210 also may be contained in a modular control tower. The modular communication hub 203 is connected to a display 212 to display images obtained by some of the devices 1*a*-1*n*/2*a*-2*m*, for example during surgical procedures. In various aspects, the devices 1*a*-1*n*/2*a*-2*m* may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1*a*-1*n*/2*a*-2*m* to the cloud. Any one of or all of the devices 1*a*-1*n*/2*a*-2*m* coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1*a*-1*n*/2*a*-2*m* located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1*a*-1*n*/2*a*-2*m*, the surgical data network provides improved surgical outcomes, reduced costs, and improved patient satisfaction. At least some of the devices 1*a*-1*n*/2*a*-2*m* may be employed to view tissue states to assess leaks or perfusion of sealed tissue after a tissue sealing and cutting procedure. At least some of the devices 1*a*-1*n*/2*a*-2*m* may be employed to identify pathology, such as the effects of diseases, using the cloud-based computing to examine data including images of samples of body tissue for diagnostic purposes. This includes localization and margin confirmation of tissue and phenotypes. At least some of the devices 1*a*-1*n*/2*a*-2*m* may be employed to identify anatomical structures of the body using a variety of sensors integrated with imaging devices and techniques such as overlaying images captured by multiple imaging devices. The data gathered by the devices 1*a*-1*n*/2*a*-2*m*, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1*a*-1*n* may be connected to the modular communication hub 203 over a wired channel or a wireless channel depending on the configuration of the devices 1*a*-1*n* to a network hub. The network hub 207 may be implemented, in one aspect, as a local network broadcast device that works on the physical layer of the Open System Interconnection (OSI) model. The network hub provides connectivity to the devices 1*a*-1*n* located in the same operating theater network. The network hub 207 collects data in the form of packets and sends them to the router in half duplex mode. The network hub 207 does not store any media access control/Internet Protocol (MAC/IP) to transfer the device data. Only one of the devices 1*a*-1*n* can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2*a*-2*m* may be connected to a network switch 209 over a wired channel or a wireless channel. The network switch 209 works in the data link layer of the OSI model. The network switch 209 is a multicast device for connecting the devices 2*a*-2*m* located in the same operating theater to the network. The network switch 209 sends data in the form of frames to the network router 211 and works in full duplex mode. Multiple devices 2*a*-2*m* can send data at the same time through the network switch 209. The network switch 209 stores and uses MAC addresses of the devices 2*a*-2*m* to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1*a*-1*n*/2*a*-2*m*. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1*a*-1*n* and devices 2*a*-2*m* located in the operating theater.

In other examples, the operating theater devices 1*a*-1*n*/2*a*-2*m* may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1*a*-1*n*/2*a*-2*m* may communicate to the modular communication hub 203 via a number of wireless or wired communication standards or protocols, including but not limited to W-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as W-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1*a*-1*n*/2*a*-2*m* and handles a data type known as frames. Frames carry the data generated by the devices 1*a*-1*n*/2*a*-2*m*. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1*a*-1*n*/2*a*-2*m*.

Figure 9:
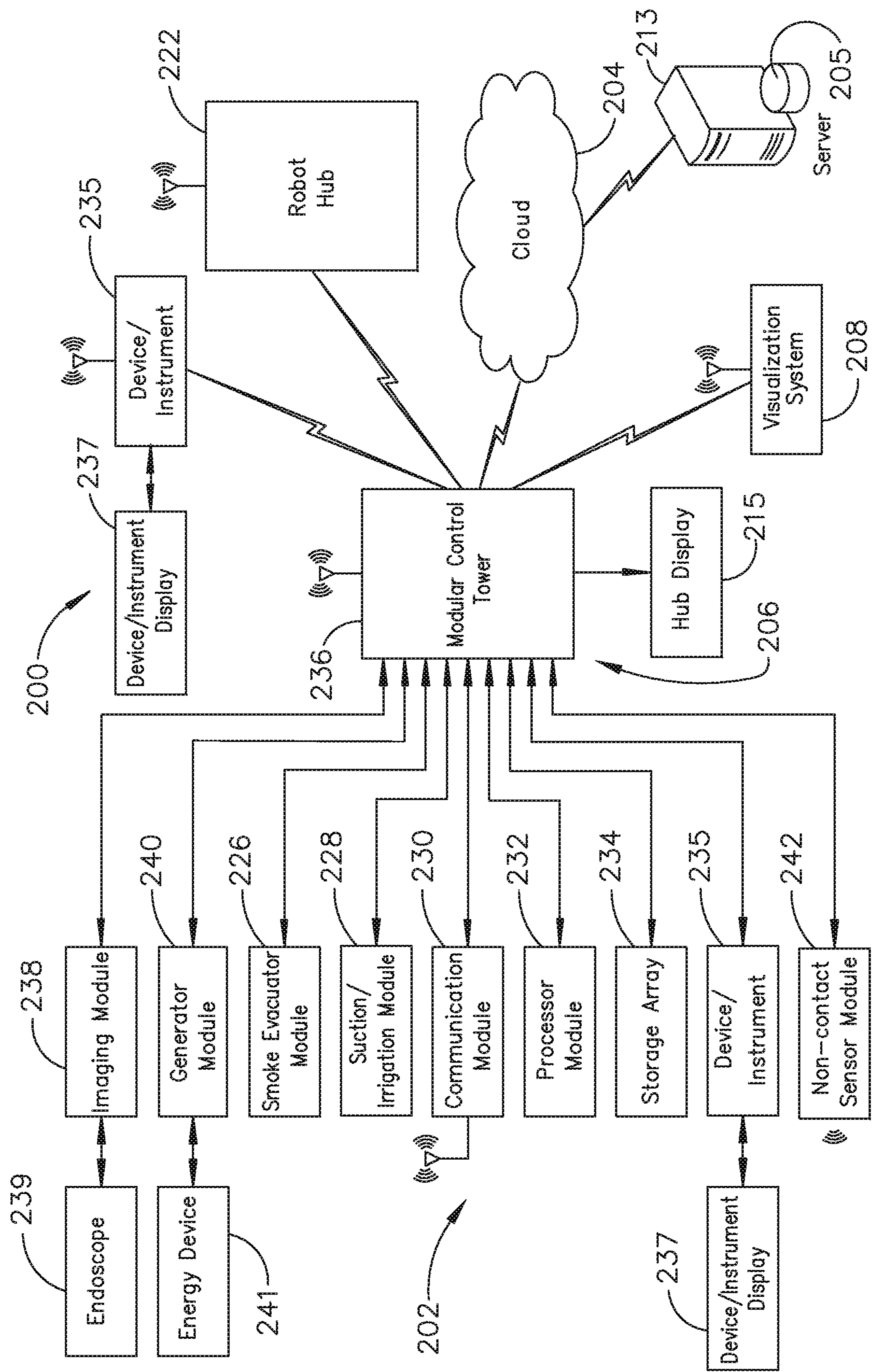
FIG. 9 illustrates a computer-implemented interactive surgical system, in accordance with at least one aspect of the present disclosure.
Figure 10:
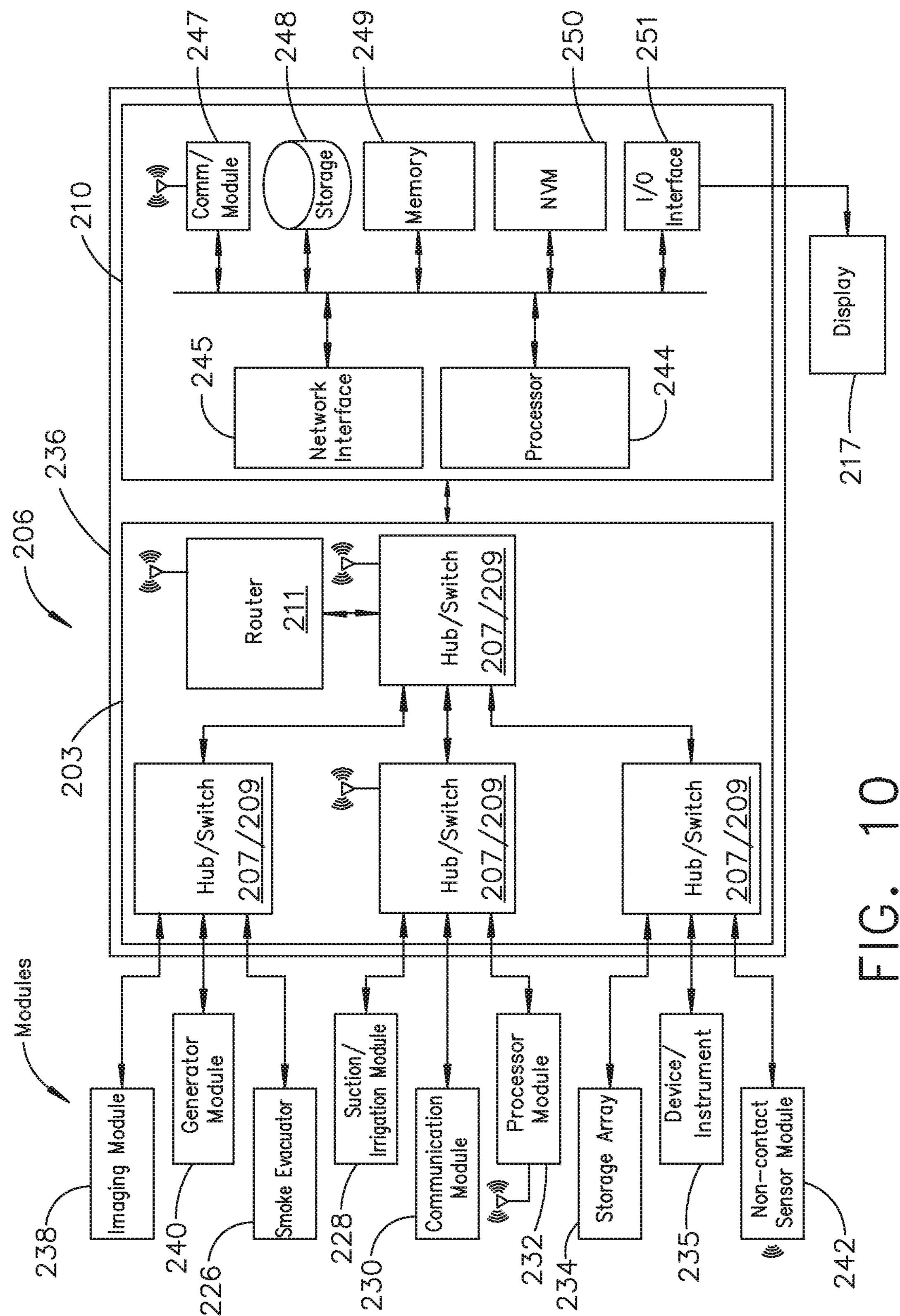
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus.

It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
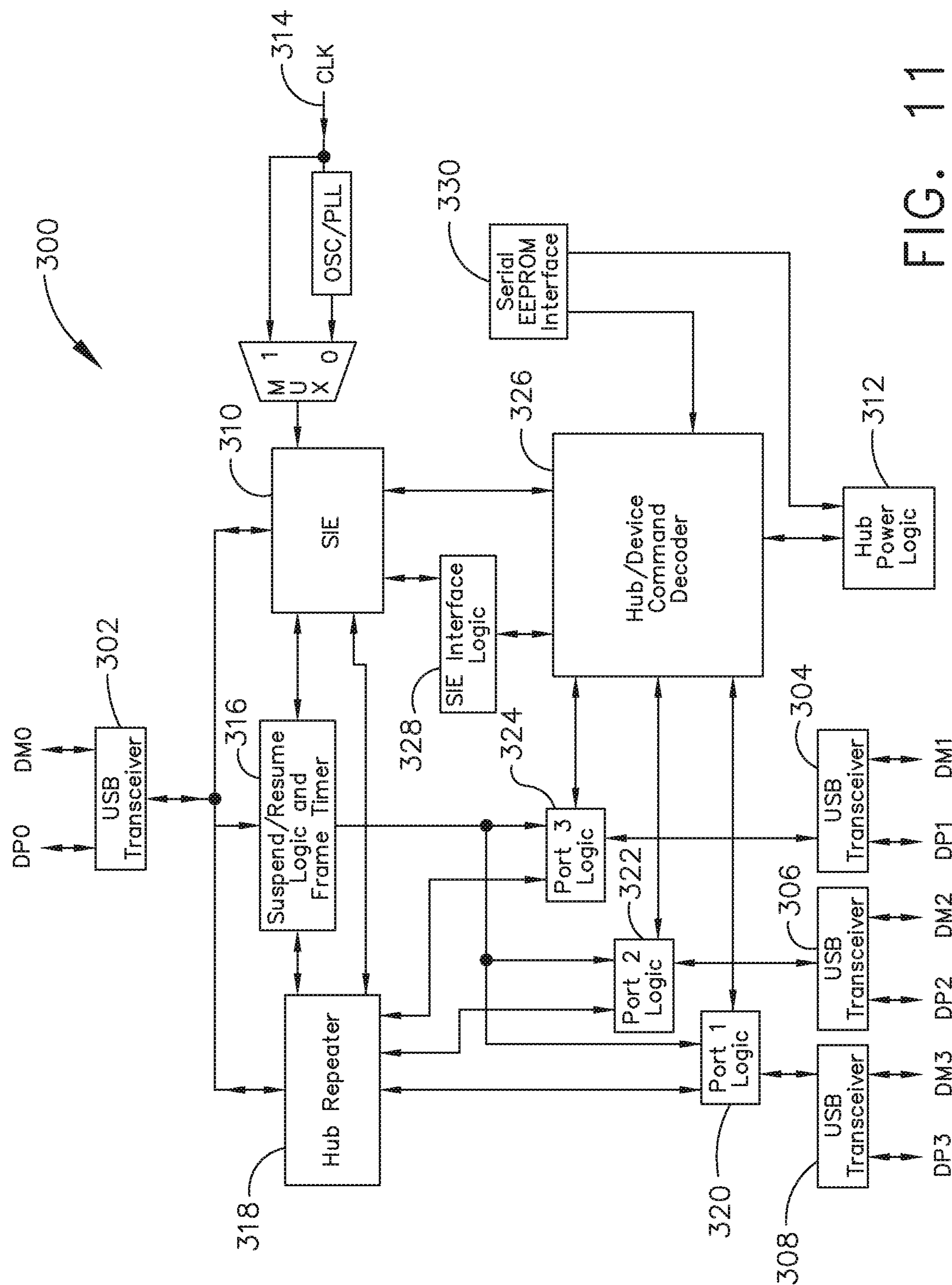
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic 328 to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Additional details regarding the structure and function of the surgical hub and/or surgical hub networks can be found in U.S. Provisional Patent Application No. 62/659,900, titled METHOD OF HUB COMMUNICATION, filed Apr. 19, 2018, which is hereby incorporated by reference herein in its entirety.

Cloud System Hardware and Functional Modules

Figure 12:
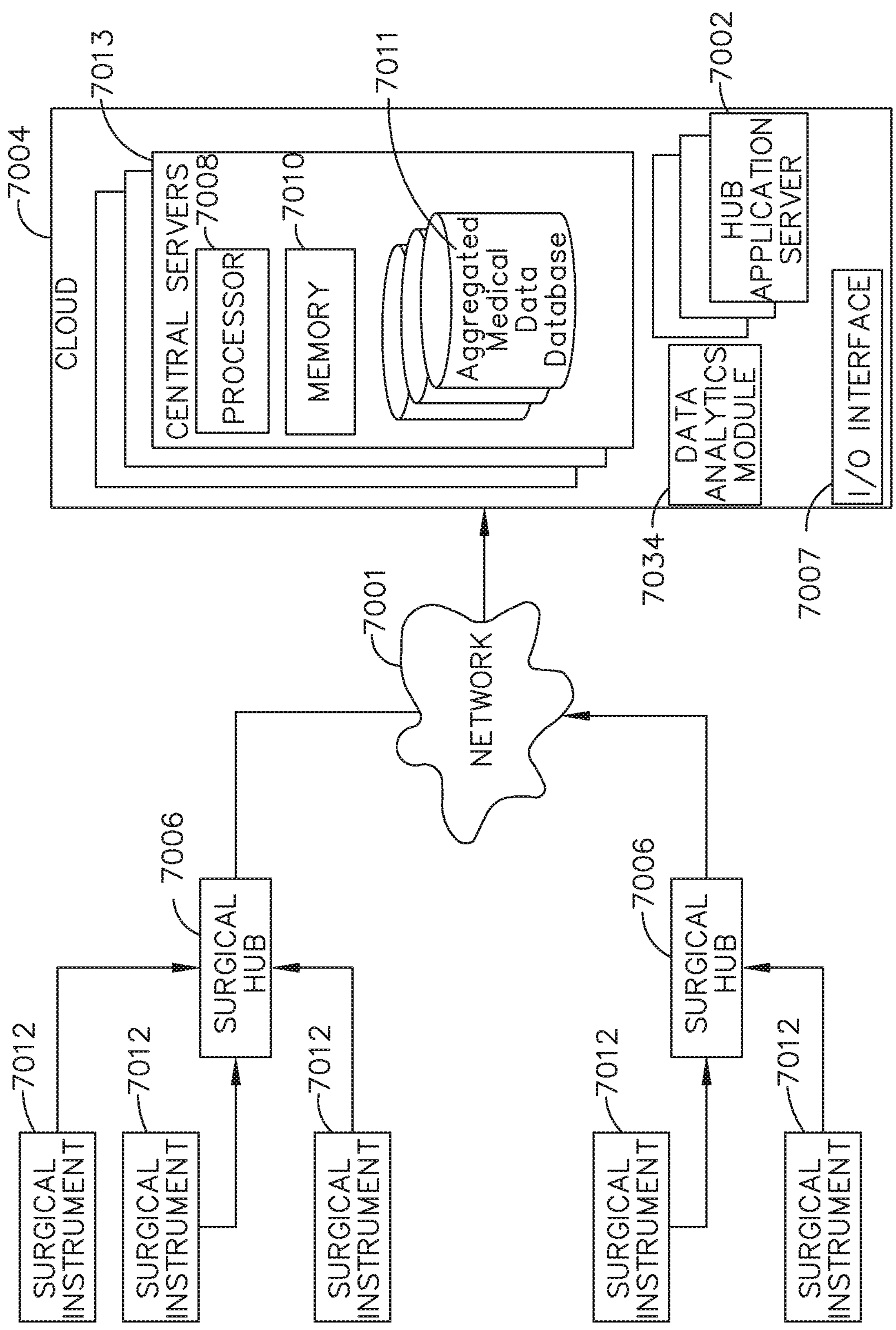
FIG. 12 is a block diagram of a cloud computing system comprising a plurality of smart surgical instruments coupled to surgical hubs that may connect to the cloud component of the cloud computing system, in accordance with at least one aspect of the present disclosure.

FIG. 12 is a block diagram of the computer-implemented interactive surgical system, in accordance with at least one aspect of the present disclosure. In one aspect, the computer-implemented interactive surgical system is configured to monitor and analyze data related to the operation of various surgical systems that include surgical hubs, surgical instruments, robotic devices and operating theaters or healthcare facilities. The computer-implemented interactive surgical system comprises a cloud-based analytics system. Although the cloud-based analytics system is described as a surgical system, it is not necessarily limited as such and could be a cloud-based medical system generally. As illustrated in FIG.

12, the cloud-based analytics system comprises a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 is communicatively coupled to one or more surgical instruments 7012. The hubs 7006 are also communicatively coupled to the cloud 7004 of the computer-implemented interactive surgical system via the network 7001. The cloud 7004 is a remote centralized source of hardware and software for storing, manipulating, and communicating data generated based on the operation of various surgical systems. As shown in FIG. 12, access to the cloud 7004 is achieved via the network 7001, which may be the Internet or some other suitable computer network. Surgical hubs 7006 that are coupled to the cloud 7004 can be considered the client side of the cloud computing system (i.e., cloud-based analytics system). Surgical instruments 7012 are paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 12, the cloud 7004 comprises central servers 7013 (which may be same or similar to remote server 113 in FIG. 1 and/or remote server 213 in FIG. 9), hub application servers 7002, data analytics modules 7034, and an input/output ("I/O") interface 7007. The central servers 7013 of the cloud 7004 collectively administer the cloud computing system, which includes monitoring requests by client surgical hubs 7006 and managing the processing capacity of the cloud 7004 for executing the requests. Each of the central servers 7013 comprises one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7011 of the cloud 7004. In particular, the cloud 7004 may advantageously perform data analysis and operations on the aggregated data to yield insights and/or perform functions that individual hubs 7006 could not achieve on their own. To this end, as shown in FIG. 12, the cloud 7004 and the surgical hubs 7006 are communicatively coupled to transmit and receive information. The I/O interface 7007 is connected to the plurality of surgical hubs 7006 via the network 7001. In this way, the I/O interface 7007 can be configured to transfer information between the surgical hubs 7006 and the aggregated medical data databases 7011. Accordingly, the I/O interface 7007 may facilitate read/write operations of the cloud-based analytics system. Such read/write operations may be executed in response to requests from hubs 7006. These requests could be transmitted to the hubs 7006 through the hub applications. The I/O interface 7007 may include one or more high speed data ports, which may include universal serial bus (USB) ports, IEEE 1394 ports, as well as W-Fi and Bluetooth I/O interfaces for connecting the cloud 7004 to hubs 7006. The hub application servers 7002 of the cloud 7004 are configured to host and supply shared capabilities to software applications (e.g. hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 13.

The particular cloud computing system configuration described in the present disclosure is specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch controlled user interfaces such that clinicians may control aspects of interaction between the surgical instruments 7012 and the cloud 7004. Other suitable user interfaces for control such as auditory controlled user interfaces can also be used.

Figure 13:
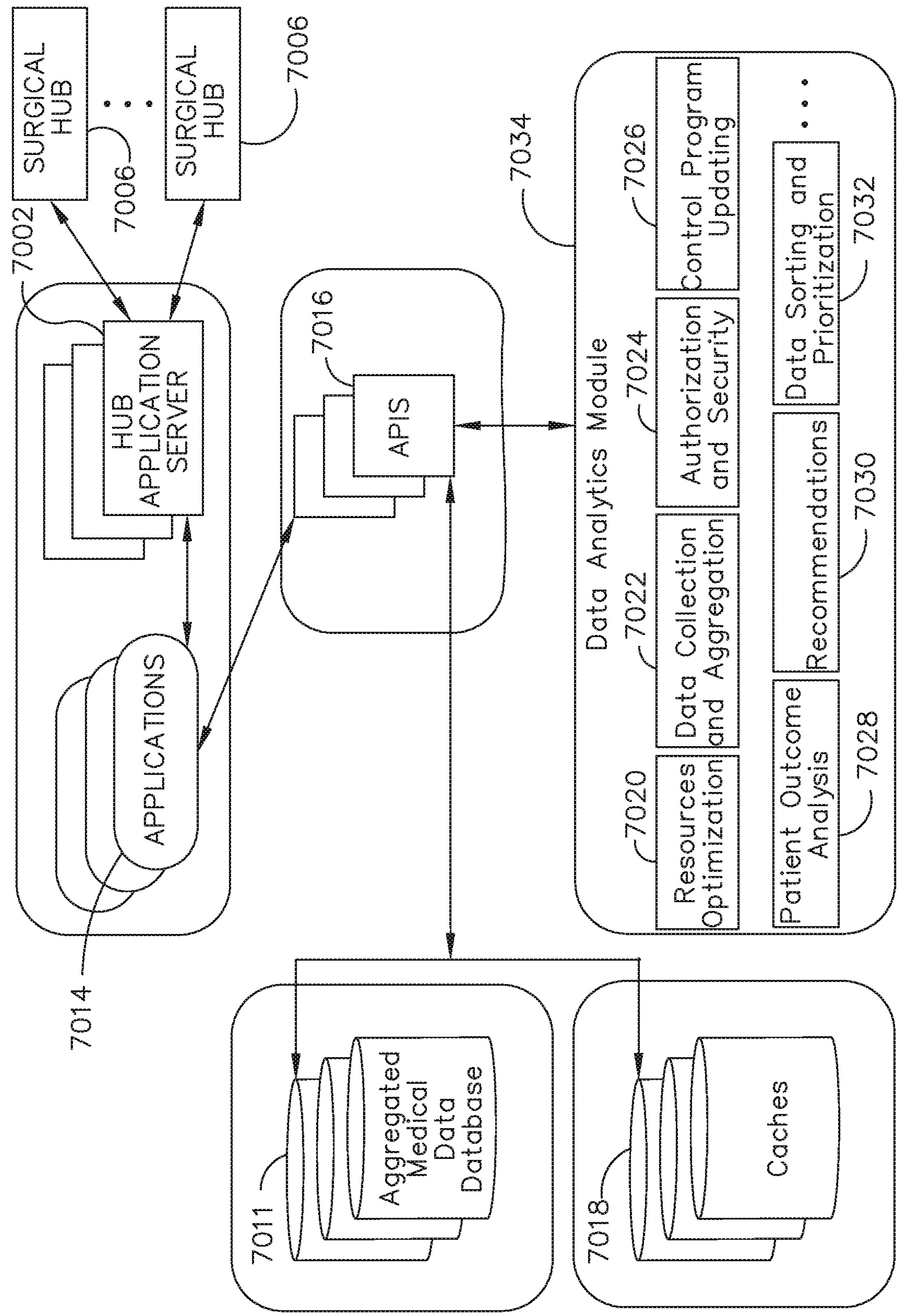
FIG. 13 is a functional module architecture of a cloud computing system, in accordance with at least one aspect of the present disclosure.

FIG. 13 is a block diagram which illustrates the functional architecture of the computer-implemented interactive surgical system, in accordance with at least one aspect of the present disclosure. The cloud-based analytics system includes a plurality of data analytics modules 7034 that may be executed by the processors 7008 of the cloud 7004 for providing data analytic solutions to problems specifically arising in the medical field. As shown in FIG. 13, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 define the set of protocols and routines corresponding to the hub applications 7014. Additionally, the APIs 7016 manage the storing and retrieval of data into and from the aggregated medical data databases 7011 for the operations of the applications 7014. The caches 7018 also store data (e.g., temporarily) and are coupled to the APIs 7016 for more efficient retrieval of data used by the applications 7014. The data analytics modules 7034 in FIG. 13 include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules are used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical hub 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently.

The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that are transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004.

Furthermore, for security purposes, the cloud could maintain a database of hubs 7006, instruments 7012, and other devices that may comprise a “black list” of prohibited devices. In particular, a surgical hub 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described above to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g. a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional details regarding the cloud analysis system can be found in U.S. Provisional Patent Application No. 62/659,900, titled METHOD OF HUB COMMUNICATION, filed Apr. 19, 2018, which is hereby incorporated by reference herein in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 14:
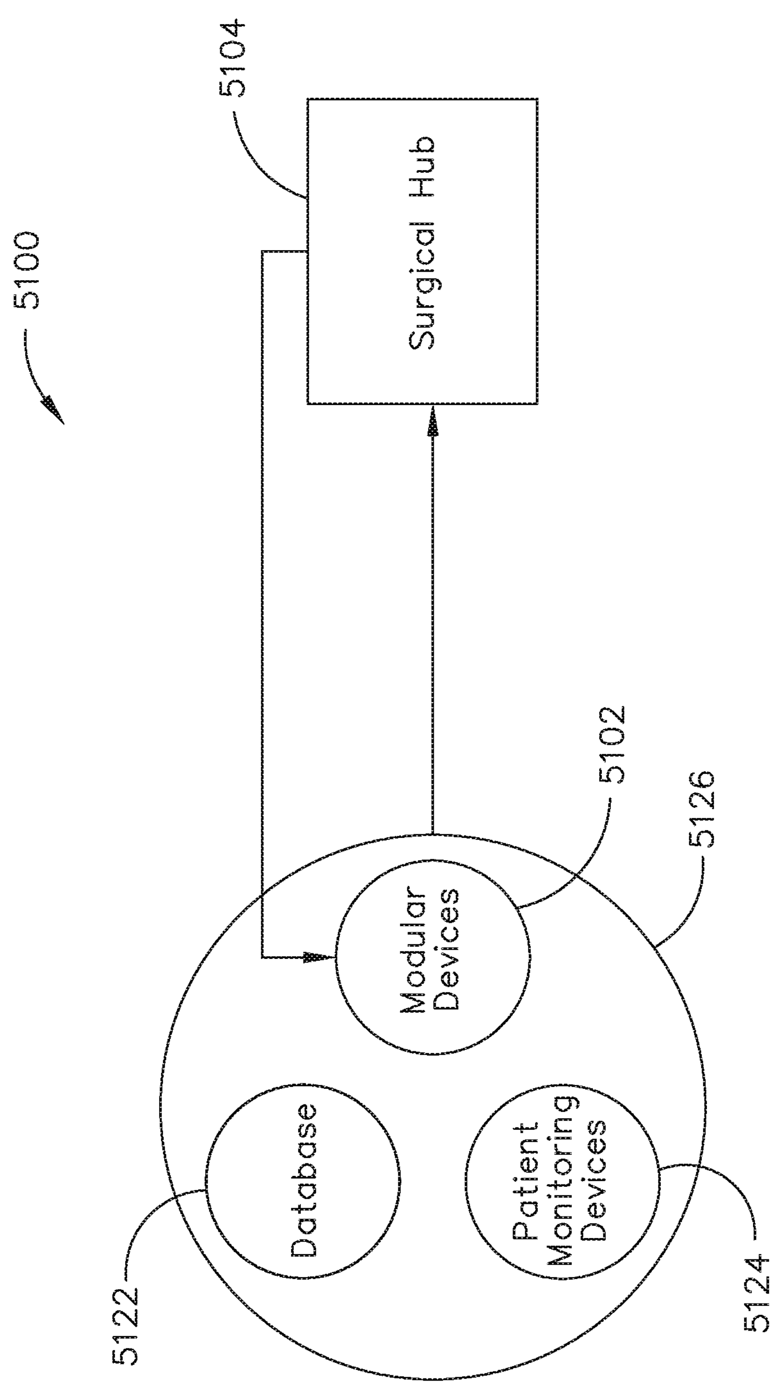
FIG. 14 illustrates a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 14 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor).

A surgical hub 5104, which may be similar to the hub 106 in many respects, can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure scanned by a suitable scanner for example, and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Figure 15:
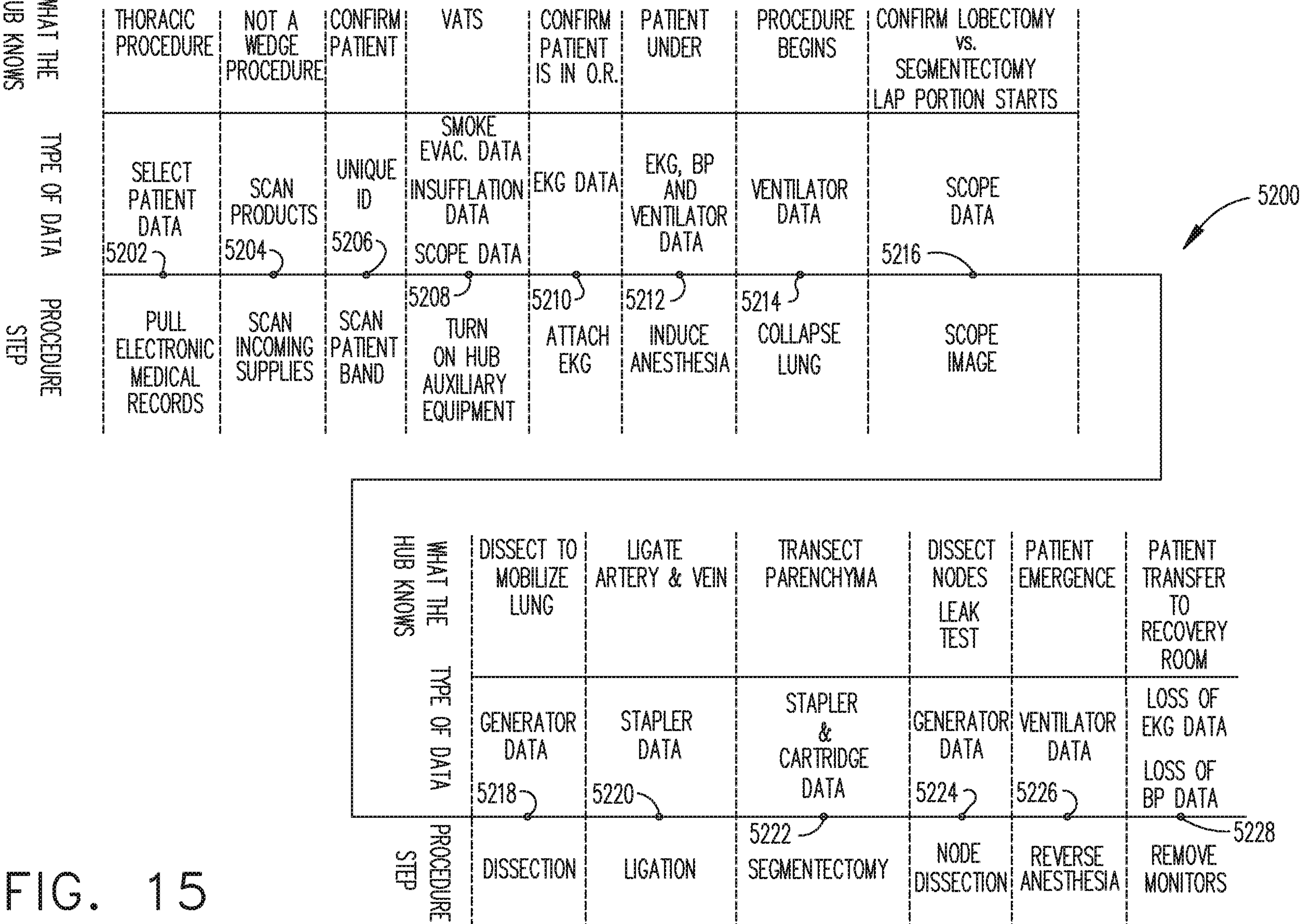
FIG. 15 is a timeline depicting situational awareness of a surgical hub, in accordance with at least one aspect of the present disclosure.

Referring now to FIG. 15, a timeline 5200 depicting situational awareness of a hub, such as the surgical hub 106 or 206 (FIGS. 1-11), for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step S202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step S204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step S206, the medical personnel scan the patient band via a scanner that is communicably connected to the surgical hub 106, 206. The surgical hub 106, 206 can then confirm the patient's identity based on the scanned data.

Fourth step S208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step S210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step S212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step S212, the pre-operative portion of the lung segmentectomy procedure is completed and the operative portion begins.

Seventh step S214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step S216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step S204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step S218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step S220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step S222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step S224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step S224, the incisions are closed up and the post-operative portion of the procedure begins.

Thirteenth step S226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step S228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

Situational awareness is further described in U.S. Provisional Patent Application Ser. No. 62/659,900, titled METHOD OF HUB COMMUNICATION, filed Apr. 19, 2018, which is herein incorporated by reference in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 104.

Situational awareness can play an important role in how a surgical hub (e.g. 106, 206, 5104) responds or reacts to various sensed parameters. For brevity, the following discussion is focused on the surgical hub 5104. It is, however, understood, that the following discussion is also applicable to other surgical hubs described herein such as, for example, the surgical hubs 106, 206.

In one aspect, the adjustment of a surgical hub 5104 response to a sensed parameter or event can be based on a second pre-existing sensed step, situation, or parameter. In one aspect, the surgical hub 5104 can have a first response to a trigger in a first situation and a second response to the same trigger under a second situation.

Figure 16:
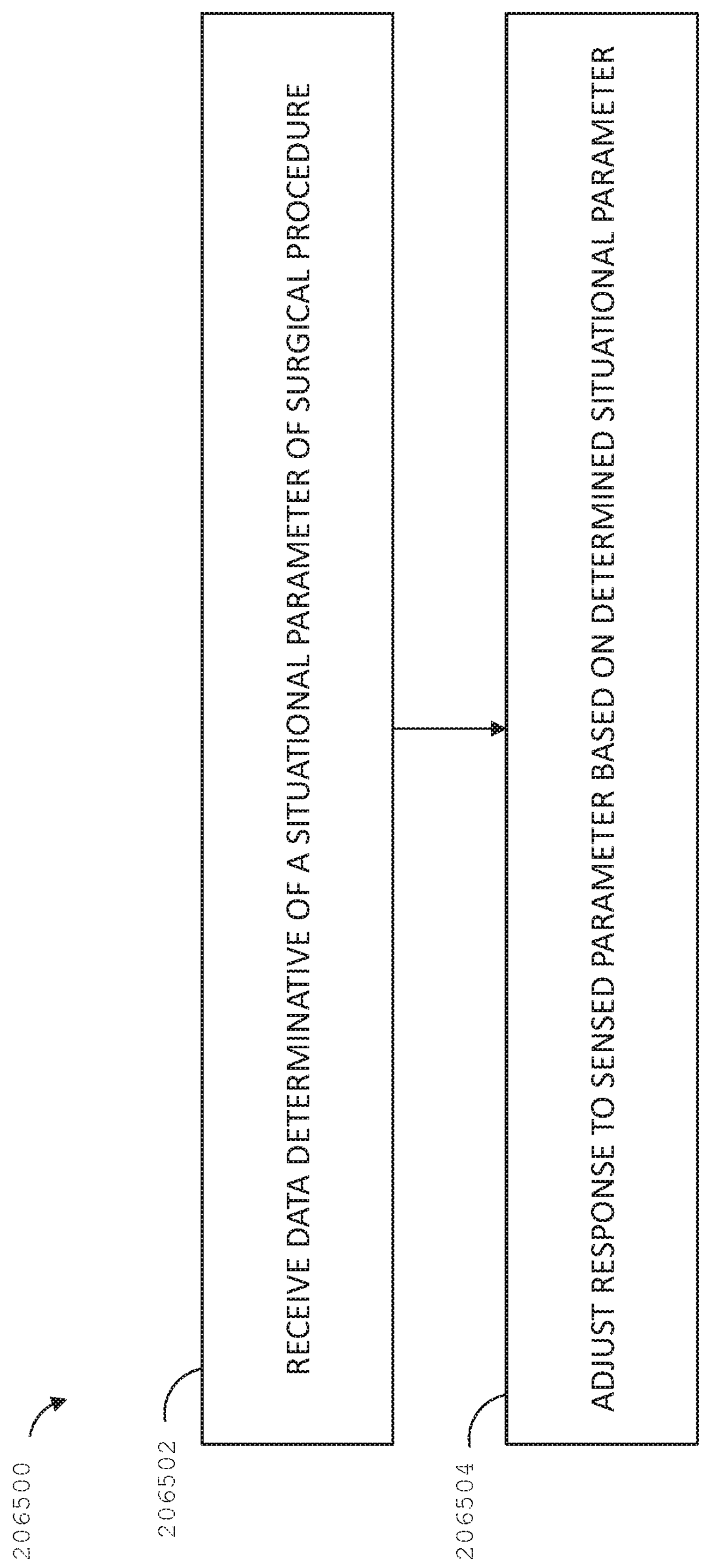
FIG. 16 is a logic flow diagram of a process depicting a control program or a logic configuration for adjusting surgical hub responses, in accordance with at least one aspect of the present disclosure.

FIG. 16 is a logic flow diagram of a process 206500 depicting a control program or a logic configuration for adjusting surgical hub responses. The process 206500 can be performed by any suitable control circuit such as, for example, a control circuit of a surgical hub (e.g. surgical hub 106, 206). The process 206500 includes receiving 206502 data from at least one data source communicably coupled to the surgical hub 5104. The at least one data source can be, for example, a patient monitoring device, a surgical staff detection device, a module device detection device and/or hospital database is processed by the surgical hub 106, 206 to determine a progress status of a surgical procedure. The received data can be determinative of a situational parameter of a surgical procedure that is being performed by the surgical hub. In various examples, the situational parameter represents a progress status of the surgical procedure, as illustrated in FIG. 17.

Figure 17:
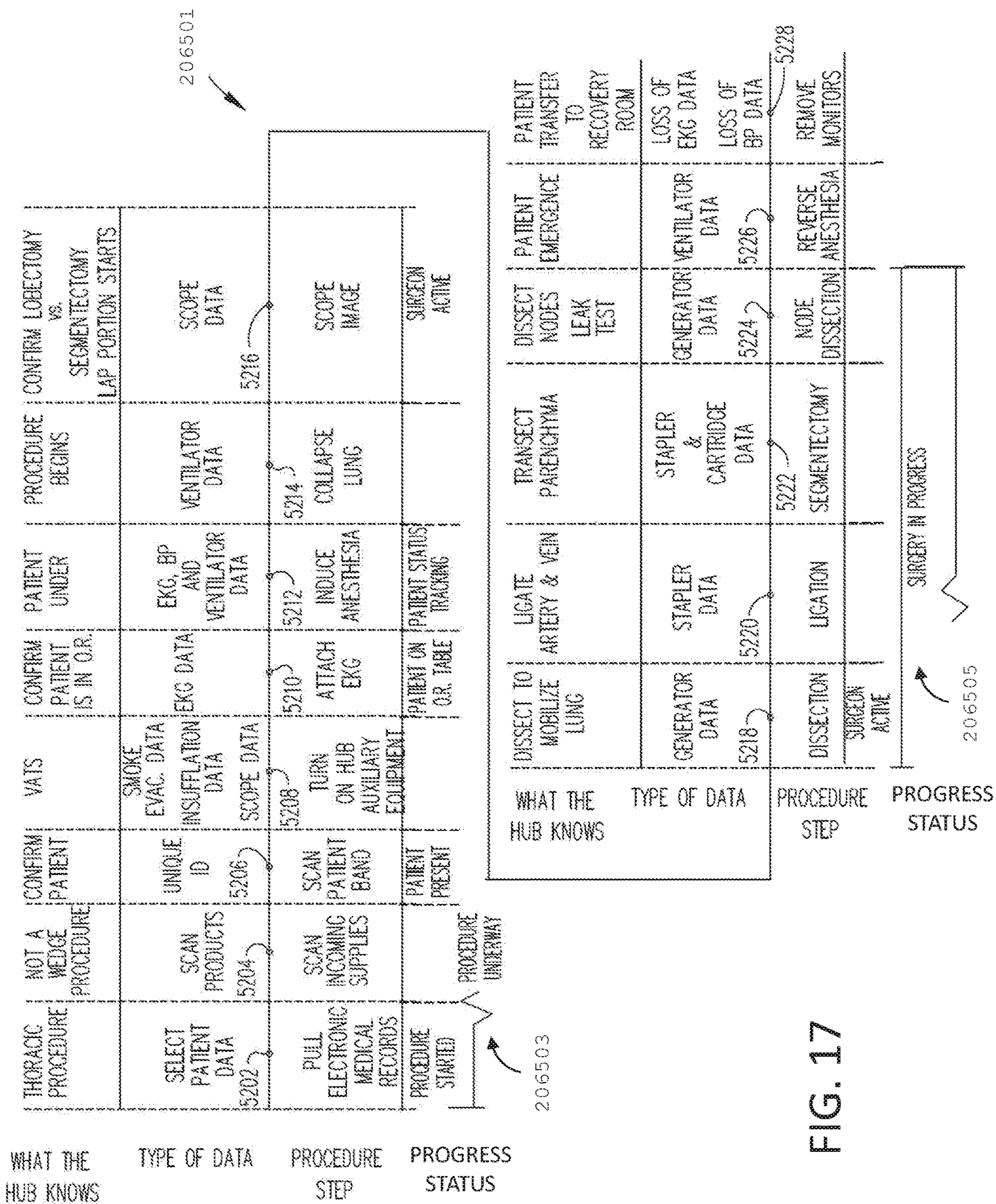
FIG. 17 is a timeline of an illustrative surgical procedure and the corresponding information inferred by a surgical hub during the procedure, in accordance with at least one aspect of the present disclosure.

FIG. 17 is a timeline 206501 of an illustrative surgical procedure and the corresponding information inferred by a surgical hub 5104 during the procedure, in accordance with at least one aspect of the present disclosure. The timeline 206501 is similar in many respects to the timeline 5200 of FIG. 15. In addition, the timeline 206500 further depicts a progress status of the surgical procedure. The progress status may comprise a preoperative status 206503 that reflects that the surgical procedure is underway. In the preoperative status, various preoperative steps are performed to prepare the operating room for surgery. The progress status may also comprise an intraoperative status 206505 that reflects that the surgery has begun.

In various examples, activation of a surgical hub in an operating room signifies that a surgical procedure has started and, is underway, which causes the surgical hub to detect a preoperative status 206503. Additional data sources could also be relied upon, alone or in combination, in detecting the preoperative status 206503. For example, receiving 5206 a scan of a patient band via a scanner that is communicably connected to the surgical hub 5104 can indicate a preoperative status 206503. Additionally, or alternatively, receiving 5210 data from a patient monitoring device such as, for example, an EKG can indicate a preoperative status 206503.

As described above, the surgical hub 5104 can infer that the patient is under anesthesia based on data from the modular devices and/or patient monitoring devices, including EKG data, blood pressure data, ventilator data, or combinations thereof, for example. Upon completion of the sixth step S212, the pre-operative portion of the lung segmentectomy procedure is completed. Accordingly, receiving such data can indicate a transition from the preoperative status 206503 to the intraoperative status 206505.

In one aspect, the surgical hub controls can be based on the awareness of whether or not a procedure is in process (i.e., whether a surgical procedure is currently being performed in connection with the particular surgical hub). Accordingly, the surgical hub controls can be based on the situation in which it senses itself.

Figure 21:
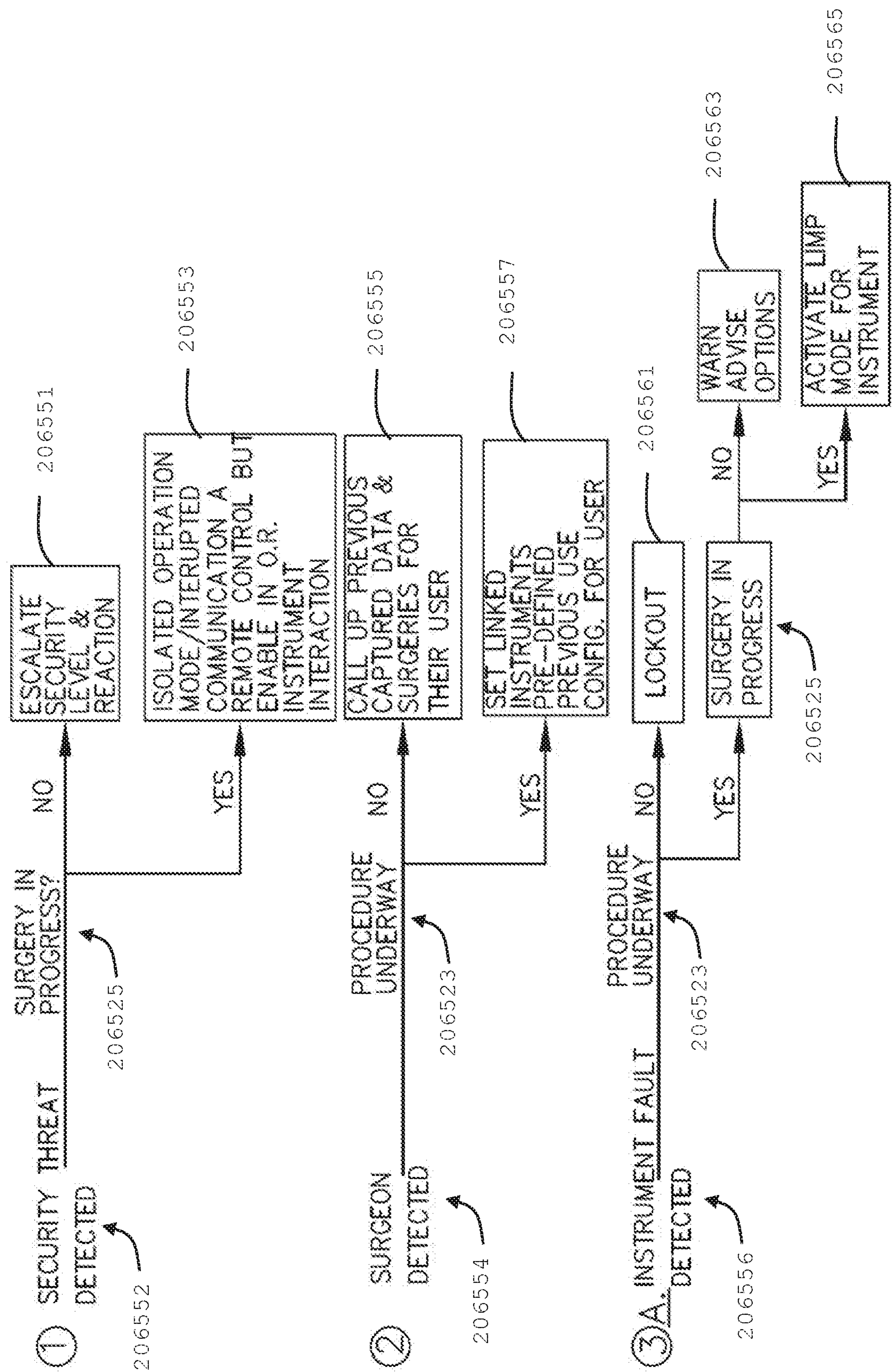
FIG. 21 is a logic flow diagram of a process depicting a control program or a logic configuration for responding to sensed parameters, in accordance with at least one aspect of the present disclosure.

The process 206500 further includes adjusting 206504 a response to a sensed parameter based on the determined situational parameter or progress status of the surgical procedure. In at least one example, as illustrated in FIG. 21, the sensed parameter can be detecting security threat. In other examples, the sensed parameter can be detecting a surgeon. In other examples, the sensed parameter can be detecting an instrument fault such as, for example, a modular device.

Figure 18:
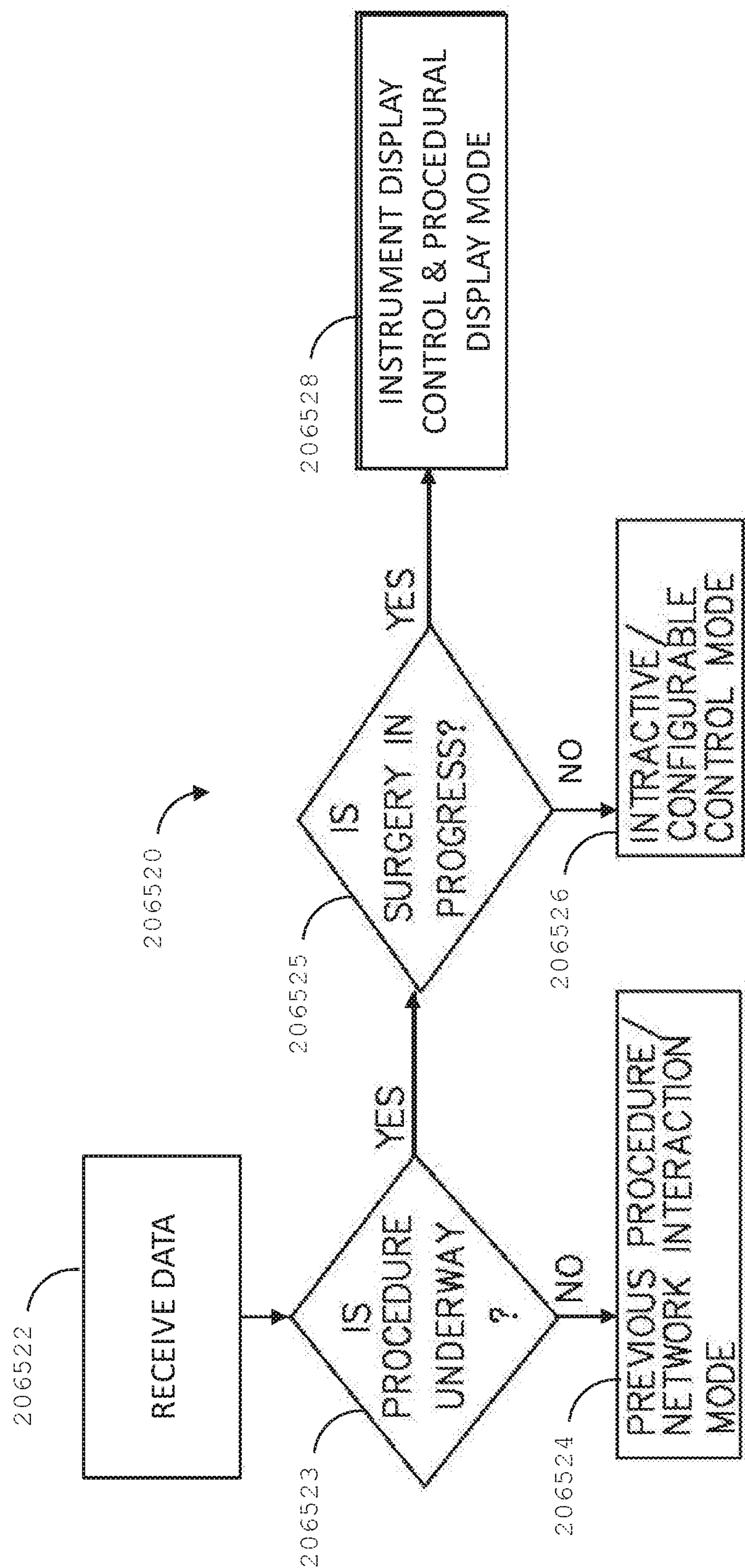
FIG. 18 is a logic flow diagram of a process depicting a control program or a logic configuration for selecting operational modes of a surgical hub, in accordance with at least one aspect of the present disclosure.
Figure 19:
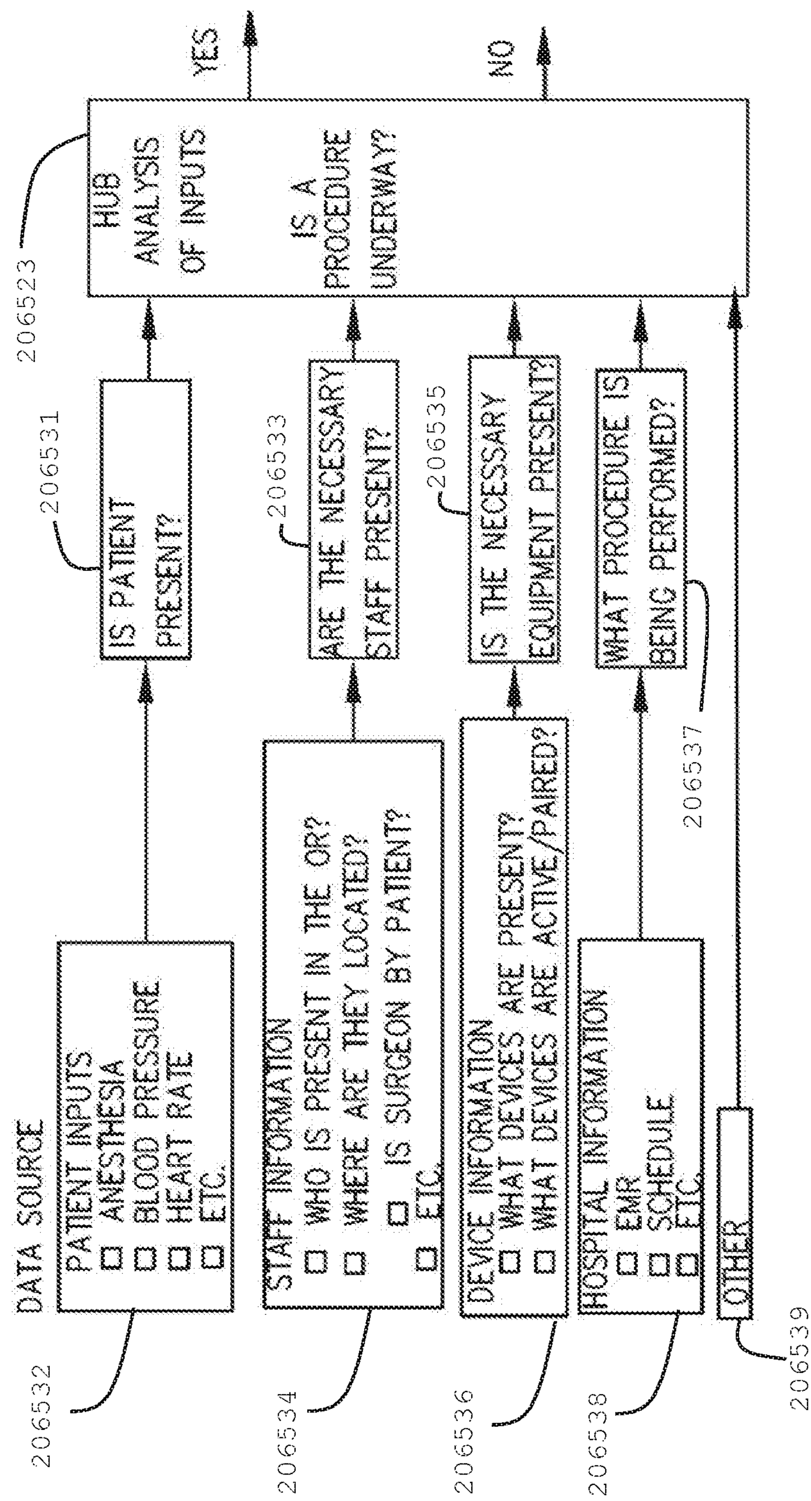
FIG. 19 is a logic flow diagram of a process depicting a control program or a logic configuration for determining whether a surgical procedure is underway, in accordance with at least one aspect of the present disclosure.

FIG. 18 illustrates is a logic flow diagram of a process 206520 depicting a control program or a logic configuration for selecting operational modes of a surgical hub 5104, in a surgical procedure, depending on a determined progress status of the surgical procedure. The process 2065520 can be performed by any suitable control circuit such as, for example, a control circuit of a surgical hub 5104. Data can be received 206522 from at least one data source, and may include patient data 206532 from a patient monitoring device, surgical staff data 206534 from a surgical staff detection device, modular device data 206536 from one or more modular devices and/or hospital data 206538 from a hospital database, as illustrated in FIG. 19. The received 206522 data is processed by the surgical hub 5104 to determine a progress status of the surgical procedure.

As illustrated in FIG. 18, the received 206522 data can be utilized by the surgical hub 5104 to determine 206523 whether the surgical procedure is underway. If not, the surgical hub 5104 activates or selects a previous procedure/network interaction mode 206524. If, however, the surgical hub 5104 determines 206523 that the surgical procedure is underway, it further determines 206525 whether surgery is in progress. If not, the surgical hub 5104 activates or selects an interactive/configurable control mode 206526. If, however, the surgical hub 5104 determines 206525 that the surgery is in progress, the surgical hub 5104 activates or selects an instrument display control & procedural display mode 206528

The mode 206524 is more restrictive than the mode 206526, and the mode 206526 is more restrictive than the mode 206528. This arrangement is designed to take into consideration a user error in the form of inadvertent commands, for example. Before the surgical procedure starts, the mode 206524 only permits access to previous procedure data, and a limited interaction with a cloud-based system 104, 204, for example. During the preoperative steps, but before surgery is begun, the mode 206526 provides a less restrictive interface that permits a user to access and/or configure various parameters and/or controls without being able to use or activate such controls. In the least restrictive mode 206528, which is only available during surgery, the user is allowed to use or activate controls of certain modular devices depending on the surgical step being performed, as illustrated in FIG. 23.

A surgical hub can make inferences about events that are occurring during the course of a surgical procedure and then respond accordingly. FIG. 19 addresses determining 206523 whether a surgical procedure is underway, in accordance with the process 206520, for example. A surgical hub can sense (or determine or infer) whether or not it is in a procedure based on attached devices and data feeds to, e.g., selectively show real-time data or the previous surgery's data.

As described above, data from various data sources can be analyzed, for example by a surgical hub 5104, to determine 206523 whether a surgical procedure is underway. Patient data 206532 from one or more patient monitoring devices can be used to determine 206531 whether a patient is present in the operating room. Additionally, or alternatively, surgical staff data 206534 from a surgical staff detection device can be used to determine 206533 whether the necessary supporting staff for the surgical procedure is present in the operating room. Additionally, or alternatively, modular device data 206536 from one or more modular devices can be used to determine 206535 whether the equipment necessary for performing the surgical procedure is present in the operating room. Additionally, or alternatively, hospital data 206538 from one or more hospital databases can be used to determine 206537 the type of procedure being performed, for example.

The determinations at 206531, 206533, 206535, 206537 can be used separately, or in any suitable combination, to determine 206523 whether a surgical procedure is underway. In various examples, each of the determinations at 206531, 206533, 206535, 206537 can be assigned a predetermined value when achieved. The summation of all the values can then be compared to a predetermined threshold to determine 206523 whether the surgical procedure is underway. In certain examples, a surgical hub 5104 must achieve each of the determinations at 206531, 206533, 206535, 206537 before determining 206523 that a surgical procedure is underway.

Referring still to FIG. 19, the patient data 206532 may include patient blood pressure data from a blood pressure monitoring device, heart rate data from a heart rate monitoring device, anesthesia data, and/or ventilator data from a ventilator and/or data from a patient identification tag. Other data sources from other devices that interact with the patient within the operating room are also contemplated by the present disclosure. For example, as described above in greater detail, a surgical hub 5104 can receive a unique identifier from, for example, a scanner for scanning the patient's wristband encoding the unique identifier associated with the patient when the patient enters the operating theater.

Furthermore, surgical staff data 206534 from a surgical staff detection device can be analyzed to determine the identity of the individuals in the operating room and/or where they are located with respect to the patient. For example, surgical staff data 206534 can be analyzed to assess whether a surgeon is standing in close proximity to the patient. For example, a surgical hub can receive a unique identifier from, for example, a scanner for scanning surgical staff wristbands encoding the unique identifier associated with each member of the surgical staff patient when they enters the operating theater. Other techniques for identifying a patient and/or a surgical staff are disclosed in U.S. Provisional Application No. 62/659,900, titled METHOD OF HUB COMMUNICATION, filed on Apr. 19, 2018, which is hereby incorporated by reference herein in its entirety.

Further to the above, the modular device data 206536 may include identification data for determining what devices are present in the operating room and/or what devices are active and/or paired with a surgical hub, for example. In one exemplification, a surgical hub can be configured to compare the list of items for a procedure (scanned by the scanner, for example) and/or a list of devices paired with the surgical hub to a recommended or anticipated manifest of items and/or devices for the given surgical procedure to determine 206535 whether the necessary equipment for the surgical are present in the operating room.

Further to the above, the hospital data 206538 may include EMR data that can be pulled from an EMR database containing patient records. Based on select patient data in the EMR, a surgical hub can determine the type of procedure to be performed, for example, which is helpful in assessing whether the surgical procedure is underway. In various examples, it is contemplated that other 206539 data can be received and analyzed by a surgical hub to determine 206523 whether a surgical procedure is underway, in accordance with the process 206520, for example.

Figure 20:
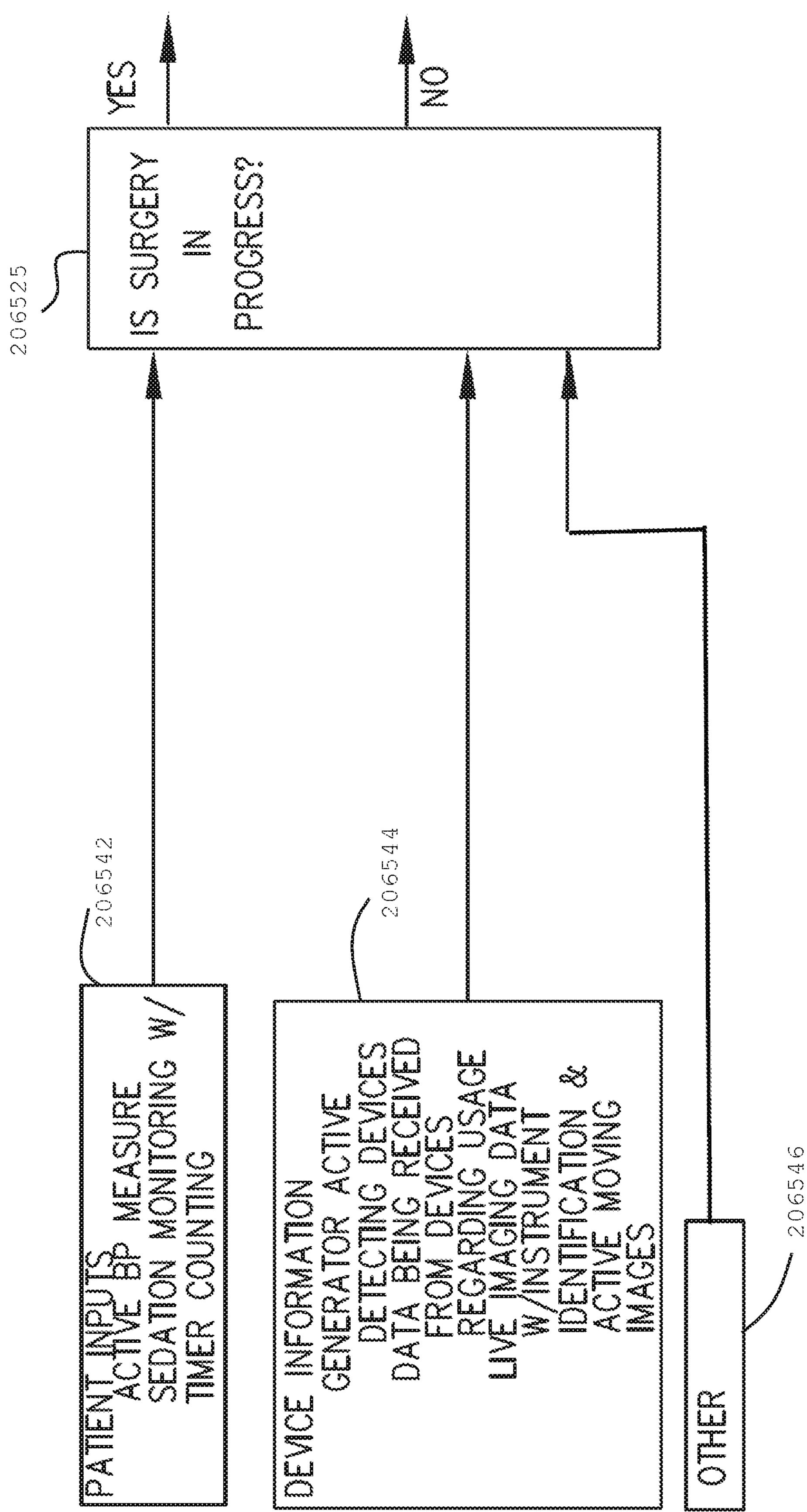
FIG. 20 is a logic flow diagram of a process depicting a control program or a logic configuration for determining whether surgery is in progress, in accordance with at least one aspect of the present disclosure.

FIG. 20 addresses determining 206525 whether surgery is in progress, in accordance with the process 206520, for example. Additional patient data 206542 such as, for example, active blood pressure data and/or sedation data can be analyzed by a surgical hub 5104 to determine 206525 whether surgery is in progress and/or assess the current surgical step being performed, as discussed below in connection with FIG. 23 Additionally, or alternatively, various device data 206544 such as, for example, generator data, device activation data, and/or live imaging data (with instrument identification and/or active moving images) can be analyzed by a surgical hub 5104 to determine 206525 whether surgery is in progress. In various examples, it is contemplated that other 206546 data can be received and analyzed by a surgical hub to determine 206525 whether surgery is in progress, in accordance with the process 206520, for example.

As described above, the process 206500 includes adjusting 206504 a response to a sensed parameter based on a determined situational parameter or progress status of a surgical procedure. In at least one example, as illustrated in FIG. 21, the sensed parameter can be detecting 206552 a security threat. In other examples, the sensed parameter can be detecting 206554 a surgeon. In other examples, the sensed parameter can be detecting 20559 an instrument fault such as, for example, a modular device.

Further to the above, responding to a detected 206552 security threat depends on whether surgery is progress, which can be determined 206525, as described above in connection with FIG. 20. If it is determined 206525 that surgery is in progress, an isolated operation mode 206553 can be activated. If surgery is not in progress, the current security level can escalated 206551 to a higher security level, and an appropriate reaction or response can be taken to address the detected 206552 security threat.

In various examples, the isolated operation mode 206553 comprises interrupting communications with external systems such as, for example, the cloud-based system 104, 204. In certain examples, the communications interruption excludes local communications within an operating room such as, for example, instrument-to-instrument communications, instrument-to-surgical hub 106, 206 communications, and/or remote controller-to-instrument communications.

Referring still to FIG. 21, responding to a detected 206554 surgeon depends on whether the surgical procedure is underway, which can be determined 206523, as described above in connection with FIG. 20. If it is determined 206523 that a surgical procedure is underway, linked instruments can be set 206557 to pre-defined parameters based on previous use configurations for the detected 206554 surgeon, for example. If, however, a surgical procedure is not underway, previous captured data and/or previous surgeries data can be called up 206555, for example.

Referring still to FIG. 21, responding to a detected 206556 instrument fault depends on whether the surgical procedure is underway, and further depends on whether surgery is in progress which can be determined 206523, 206525, as described above in connection with FIG. 20. An instrument can be, for example, a modular device. If it is determined 206523 that a surgical procedure is underway, and it is further determined 206525 that surgery is in progress, a limp mode can be activated 206565 for the instrument. If, however, a surgical procedure is not underway, a lockout of the surgical instrument can be engaged 206561 to prevent the surgical instrument from being used. Furthermore, if it is determined 206523 that a surgical procedure is underway, but surgery is not in progress, an alert or warning can be issued 206563 by the surgical hub 5104 to the surgical staff, for example, advising options.

Figure 22:
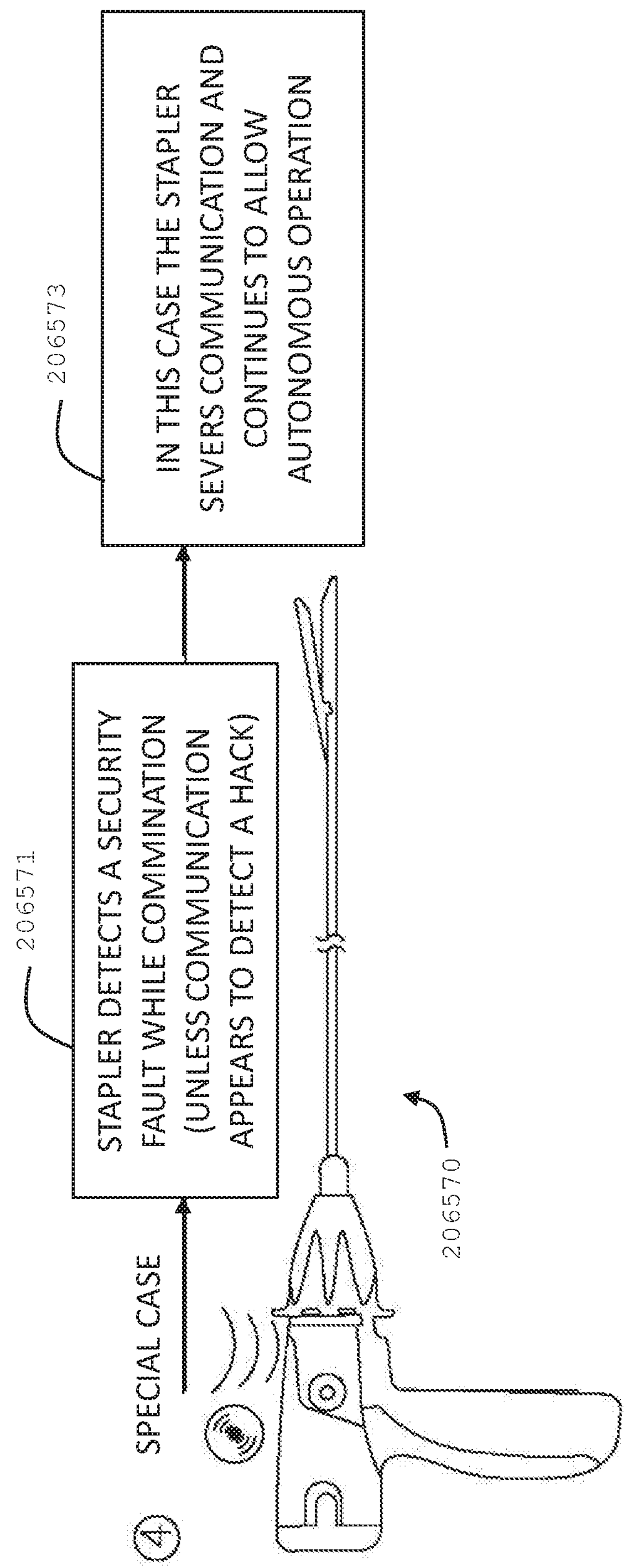
FIG. 22 is a logic flow diagram of a process depicting a control program or a logic configuration for adjusting operational parameters of a surgical stapler in the event of a detected security fault, in accordance with at least one aspect of the present disclosure.

Referring to FIG. 22, an example is provided for adjusting operational parameters of a surgical stapler 206570 in the event of a detected 206572 security fault in accordance with one or more of the above-described processes. In the example of FIG. 22, the stapler 206570 detected 206572 the security fault during communication with a surgical hub 5104 and/or with a cloud-based system 104, 204, for example. In response, the stapler 206570 severs 206573 communications with the surgical hub 5104 and/or with the cloud-based system 104, 204, and continues to allow autonomous operation unless a hack is detected.

FIG. 23 is a diagram depicting how a surgical hub 5104 can determine which step of a surgery is being performed according to various data feeds, in accordance with at least one aspect of the present disclosure. FIG. 23 also depicts various examples of responding to sensed parameters based on a determined situational parameter, in accordance with the process 206500 (FIG. 16). In the examples of FIG. 23, the determined situational parameter is the present step of an ongoing surgery.

In various instances, a surgical hub 5104 determines the present step of an ongoing surgery based on data received 206502 (FIG. 16) from various data sources described in connection with FIG. 16. In the example of FIG. 23, the surgical hub 5104 identifies the surgical steps of the surgery as Access 206580, Dissection 206582, Transection 206584, Anastomosis 206586, and Closing 206588, which is based on the received 206502 data. Furthermore, the surgical hub 5104 identifies the modular devices to be used in the surgery as a Trocar 206581, a modular energy device 206583, a linear surgical stapler 206585, and a circular surgical stapler 206585, also based on the received 206502 data.

In various examples, the surgical hub 5104 may store a database of various surgeries, the identity and order of the surgical steps pertaining to each of the surgeries, and/or the identity and/or usage or activation frequency of the modular surgical devices to be used in each of the surgical steps. In such examples, a user input selecting or identifying the surgery to be performed may be all that is needed for the surgical hub 5104 to identify the surgical steps and modular surgical devices associated with the surgery to be performed.

In other examples, the surgical hub 5104 deduces the type of surgery to be performed, and/or its corresponding surgical steps, by detecting modular surgical devices that are in close proximity to the patient and/or are within the operating room. Additionally, or alternatively, the surgical hub 5104 may determine the type of surgery to be performed, and/or its corresponding surgical steps, from a received 206502 patient EMR, for example.

FIG. 23 depicts example information that is made available to and/or is deduced by the surgical hub 5104 in connection with an example surgery 206591 that is being coordinated by the surgical hub 5104, which is based on the received 206502 data. In access 206580, the trocar 206581 and the modular energy device 206583 are used. Usage of the modular energy device 206583 is depicted in activation instances 206590, which can be repeated with or without interruptions, as depicted in FIG. 23. Each activation instance 206590 may comprise a predefined time period of energy application by the modular energy device 206583, for example. Similar activation instances 206592, 206594, 206596 are depicted for the trocar 206581, the linear surgical stapler 206585, and the circular surgical stapler 206585, respectively.

FIG. 23 also depicts erroneous, inadvertent, or unexpected activation instances 206590', 206596', which constitute examples of sensed parameters, in accordance with the process 206500 (FIG. 16). The example activation instances 206590', 206596' are activation instances of the modular energy device 206583 and the circular surgical stapler 206585, respectively, which are outside the expected, or normal, sequence of the surgery 206591 and, as such, are ignored. Alternatively, or additionally, an activation instance can be ignored if it is determined that the activated modular device is too far away from the surgical site. For example, an activation instance can be ignored if it is determined that the activated modular device is located on a sterile table, for example. Any suitable proximity sensors can be employed to determine the position of the activated modular device. Alternatively, or additionally, an activation instance can be ignored if it is determined that the activated modular device is not in contact with tissue. Any suitable continuity sensors can be employed to determine whether the activated modular device is in contact with tissue.

In various examples, the surgical hub 5104 could ignore hand piece activation based on depression of the buttons on the handle of a modular energy device if the surgical hub 5104 is aware the generator, surgical hub 5104, and/or the modular energy device are not in an active surgery. This can reduce inadvertent activation of devices. Furthermore, this could operate on a finer control level as well: If the surgical hub 5104 determines that the modular energy device is not inside the patient or in contact with a patient's tissue by sensing continuity or the linking of the return path of the return pad, the activation of the modular energy device could be ignored. This could even be used relative to patient proximity in aspects where the system is capable of instrument tracking.

In one aspect, the surgical hub controls can be programmed such that fault detection during a surgery triggers a different response than fault detection does before or after a surgery. Accordingly, the severity of the surgical hub's response to faults can be based on its awareness of its use status.

FIG. 24 is a logic flow diagram of a process 206600 depicting a control program or a logic configuration for determining 206602 whether a modular device is in optimal condition and/or performing 206604 a severity assessment in the event it is determined that the modular device is in a suboptimal condition or is not functioning properly. A surgical hub 5104 may receive 206601 data from various sources indicative of device usage history, device status, recent performance, device authentication/identification data, device compatibility, and/or other data. The surgical hub 5104 may analyze such data to determine 206602 whether a modular device is in optimal condition. If so, the surgical hub 5104 permits the modular device to operate in a fully enabled device mode 206603. If not, the surgical hub 5104 performs 206604 a severity assessment. Based on the severity assessment, the surgical hub 5104 may take steps to provide a warning 206605, cause a reduction in available device functionality 206606, force a device change 206607, and/or take any other suitable action 206608.

In one aspect, a detected fault severity response can be based on whether the surgical hub 5104 believes the device is unsafe or could be put into a limp mode because it is currently in-use. For example, if a counterfeit cartridge reload is used in a procedure, the user is warned 206605, but the product is allowed to be used with surgeon override if the modular device is already in-use. As opposed to a reload being installed at the beginning of a procedure, for example in the pre-operative stage, at which point the severity it senses might be a higher level and it may lock-out the use of that combination of products. As another example, the number of uses flag can be treated in one manner before and after the procedure, as opposed to it being triggered during a procedure. The surgical hub's inclination to lockout a device that has been reused too many times before a procedure can be overridden to allow the device to continue if the trigger is activated while in a procedure. The inclination to lockout the device can then be restored once the procedure is complete.

In one aspect, security responses in certain situations could be substantially more restrictive based on the situational awareness of the surgical hub 5104. Accordingly, surgical hub's security response can be based on its perceived need for secure use. For example, the protective reaction to a system attack might be elevated if the system is aware that it is in-use. As another example, the protective response to an attack might be escalated if surgical hubs are already aware they are under attack in other locations. As yet another example, remote access for controlling aspects of the modules within the surgical hub 5104 could be limited when the surgical hub is in use in a procedure. In one implementation, the external control aspects of the modular devices could be disabled when local control is established. In another implementation, when remote access is requested and a procedure is in process or there is a sensed use by a local user, the surgical hub might request confirmation locally for permission before granting permission for remote control of the system or function.

In one aspect, the configuration and responses of the surgical hub 5104 could be altered based on the user the surgical hub senses is in-use. Accordingly, the surgical hubs can be programmed to automatically re-configure based on sensed users. For example, the default configuration of an attached device and the controls of the device could be adjusted based on the user the surgical hub senses is using the device. If a specific surgeon doing a specific procedure always tends to use a device or its control in a repeatable manner, the surgical hub could automatically configure the device for the user as its learns his or her behavior. As another example, the surgical hub 5104 can learn the behaviors of the users it works with. This could even be with a network of hubs, which could each communicate preferences, setups, and alterations in device setup for specific users. Accordingly, when a specific user is sensed, either by login or another technique, the surgical hub 5104 could then start configuring the systems based on previous uses by the user in question.

In various aspects, a modular device 5102 such as, for example, a surgical instrument may interact with other modular devices 5102 and/or surgical hubs 5104. The interaction may occur before, during, and/or after a surgical procedure commences. For example, the modular device 5102 may receive a firmware update from a surgical hub 5104 before the surgical procedure. In another example, the modular device 5102 may receive commands from a remote controller during a surgical procedure. In yet another example, the modular device 5102 may transmit usage data to a surgical hub 5104 regarding a surgical procedure after completion of the surgical procedure. Unauthorized interactions between a modular device 5102 and other modular devices 5102 and/or surgical hubs 5104 can interfere with the proper operation of such devices and systems.

Ensuring a secure interaction between a modular device 5102 and other modular devices 5102 and/or surgical hubs 5104 can be achieved by generating an appropriate response to an unauthorized interaction. In various aspects, the response of a modular device 5102 to a potential security violation or unauthorized interaction can be adjusted based on situational awareness. In some situations, the response of a modular device 5102 to a potential security violation or unauthorized interaction can be based on situational awareness that the modular device 5102 itself is attacked, instead of a surgical hub 5104, for example.

In one aspect, a wirelessly pairable modular device 5102 can be programmed for detection and escalation of security responses in response to numerous or increasing severity threats. For example, the first response to a first violation results in a minor reaction and a second response to a second serial violation results in an escalated response. In another aspect, the escalated response could be termination of communication and/or autonomous usage only of the instrument.

In one aspect, a surgical instrument can be programmed to implement an escalation protocol to react according to the number or invasiveness of a security violation. Accordingly, a surgical instrument can be programmed to escalate security response in response to increasing threats. For example, a wireless device which pairs to another device or surgical hub and senses a first unauthorized or unauthentic interaction causes the device to execute a minor response (e.g., warn the user or raise the threat warning). When the device senses multiple additional issues or the severity of the additional issue is higher, the device's second response can be escalated much greater than the first response (e.g., end communication and only operate autonomously or only accept fully authenticated and encrypted requests). As another example, a device can execute a security response when communication interaction appears probing after already flagging an unauthentic handshake.

FIG. 25 is a logic flow diagram of a process 206610 depicting a control program or a logic configuration for generating suitable responses to unauthorized interactions with a modular device 5102, in accordance with at least one aspect of the present disclosure. The process 206610 includes detecting 206612 a first security violation or unauthorized interaction, causing 206614 the modular device 5102 to generate a first response to the first security violation or unauthorized interaction, storing 206616 a record of the first security violation or unauthorized interaction; detecting 206618 a second security violation or unauthorized interaction, and causing 206620 the modular device 5102 to generate a second response to the second security violation or unauthorized interaction, wherein the second response is escalated from the first response.

Referring to FIG. 26, in various examples, a modular device 5102 comprises a communication module 206622, a control circuit 206624, and a user interface 206626. The control circuit 206624 is coupled to the communication module 206622 and the user interface 206626, and is configured to execute the process of 206610.

In various examples, any suitable wireless communication can be employed by the communication module 206622 including, for example, Bluetooth wireless technology standard for exchanging data over short distances (using short-wavelength UHF radio waves in the ISM band from 2.4 to 2.485 GHz) from fixed and mobile devices and building personal area networks (PANs). The communication module 206622 may employ anyone of a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. In at least one example, the communication module 206622 may employ an Air Titan-Bluetooth.

In at least one example, a pairing attempt with the communication module 205522 by an unauthorized modular device or surgical hub is detected 206612. In response, the control circuit 206624 may cause 206614 the user interface 206624 to issue a warning or an alert, which can a visual and/or an audible alert. Furthermore, the modular device 5102 may store 206616 a record of the first pairing attempt in a memory unit of the control circuit 206624, for example.

If, however, a second pairing attempt by an unauthorized modular device or surgical hub is detected 206618, the control circuit 206624 may cause 206620 a second response, escalated from the first response, to be generated. For example, the control circuit 206624 may cause the communication module 206622 to terminate all external communications and/or may cause an autonomous operation mode to be activated.

In at least one example, the modular device 5102 is a surgical stapler, and the first security violation or unauthorized interaction involves loading a spent, or previously used, staple cartridge onto the surgical stapler. Detecting 206612 the spent staple cartridge can be achieved by one or more sensors and/or by interrogating a chip of the staple cartridge to assess whether its identification number is associated with a new or unspent staple cartridge. Once a first spent staple cartridge is detected 206612, the control circuit 206624 causes 206614 the user interface 206626 to issue to issue a warning or an alert, which can a visual and/or an audible alert. The alert may include instructions to remove the spent staple cartridge.

Further to the above, the modular device 5102 may store 206616 a record of the spent staple cartridge in a memory unit of the control circuit 206624, for example. If, however, the control circuit 206624 detects 206618 that the same spent staple cartridge, or another spent staple cartridge, has been loaded onto the surgical stapler, a more escalated response can be generated by the control circuit 206624. For example, the control circuit 206624 may cause the surgical stapler to enter a permanent lockout, preventing the surgical stapler from further usage. The control circuit 206624 may also report the incident to a surgical hub, for example. Other suitable escalated responses are contemplated by the present disclosure.

FIG. 27 is a logic flow diagram of a process 206630 depicting a control program or a logic configuration for generating suitable responses to unauthorized interactions with a modular device 5102, in accordance with at least one aspect of the present disclosure. A first unauthorized activation of the modular device 5102 is detected 206632 by the control circuit 206624, for example. In at least one example, an activation of the modular device 5102 while the device is on a surgical tray, or while the device is separated from the patient beyond a predetermined distance, is considered an unauthorized activation. The control circuit 206624 causes the modular device 5102 to generate 206634 a first response to a first unauthorized activation, which can be a minor response (e.g., warn the user or raise the threat warning). In one example, the control circuit 206624 may cause the user interface 206626 to issue a warning or an alert, which can a visual and/or an audible alert. Furthermore, the modular device 5102 may store 206636 a record of the first unauthorized activation in a memory unit of the control circuit 206624, for example. Furthermore, a second unauthorized activation of the modular device 5102 is detected 206638, the control circuit 206624 cause the modular device 5102 to generate a second response to the second unauthorized activation of the modular device 5102, wherein the second response is escalated from the first response.

In various aspects, a surgical hub can be configured to provide surgical hub 5104 feedback to a user. The feedback could be adjusted based on a connotation resulting from a different connotation. In one aspect, a surgical hub 5104 can be programmed to provide interactive feedback to the user that enables adjustment of a device or display based on presence of an actionable aspect of the task at hand for the user. In one aspect, the interactive feedback could include visualization improvements identified by the surgical hub/visualization module that could provide better or more complete imaging of the surgical site. In one aspect, the interactive feedback could include an alternate imaging overlay demonstrating how a device could be better articulated when a device is placed in an inopportune location.

In one aspect, the surgical hub or displays could be affected based on the sensing of an action context for the user. Accordingly, display adjustments could be based on the surgical hub's awareness of actionable context.

Various aspects of the subject matter described herein are set out in the following numbered examples:

Example 1

A surgical system for use in a surgical procedure, wherein the surgical system comprises a modular device, at least one data source, and a surgical hub configured to communicably couple to the at least one data source and the modular device. The surgical hub comprises a control circuit configured to receive data from the at least one data source, wherein the data is determinative of a progress status the surgical procedure. The control circuit is further configured to adjust a response to a sensed parameter based on the progress status.

Example 2

The surgical system of Example 1, wherein the at least one data source comprises a patient monitoring device.

Example 3

The surgical system of Example 1 or 2, wherein the at least one data source comprises a surgical staff detection device.

Example 4

The surgical system of any one of Examples 1-3, wherein the progress status comprises a preoperative status while the surgical procedure is in preoperative steps.

Example 5

The surgical system of any one of Examples 1-4, wherein the progress status comprises an intraoperative status while the surgical procedure is in intraoperative steps.

Example 6

The surgical system of any one of Examples 1-5, wherein the sensed parameter comprises a fault detection parameter.

Example 7

The surgical system of any one of Examples 1-6, wherein the sensed parameter comprises a surgeon detection parameter of the modular device.

Example 8

The surgical system of any one of Examples 1-7, wherein the sensed parameter comprises a security-threat detection parameter.

Example 9

A surgical hub for use in a surgical procedure, wherein the surgical hub is configured to communicably couple to at least one data source. The surgical hub comprises a control circuit configured to receive data from the at least one data source, wherein the data is determinative of a progress status the surgical procedure. The control circuit is further configured to adjust a response to a sensed parameter based on the progress status.

Example 10

The surgical hub of Example 9, wherein the at least one data source comprises a patient monitoring device.

Example 11

The surgical hub of Example 9 or 10, wherein the at least one data source comprises a surgical staff detection device.

Example 12

The surgical hub of any one of Examples 9-11, wherein the progress status comprises a preoperative status while the surgical procedure is in preoperative steps.

Example 13

The surgical hub of any one of Examples 9-12, wherein the progress status comprises an intraoperative status while the surgical procedure is in intraoperative steps.

Example 14

The surgical hub of any one of Examples 9-13, wherein the sensed parameter comprises a modular device fault-detection parameter.

Example 15

The surgical hub of any one of Examples 9-14, wherein the sensed parameter comprises a surgeon detection parameter.

Example 16

The surgical hub of any one of Examples 9-15, wherein the sensed parameter comprises a security-threat detection parameter.

Example 17

A surgical hub for use in a surgical procedure, wherein the surgical hub is configured to communicably couple to at least one data source. The surgical hub comprises a control circuit configured to receive data from the at least one data source, wherein the data is determinative of a situational parameter of the surgical procedure. The control circuit is further configured to adjust a response to a sensed parameter based on the situational parameter.

Example 18

The surgical hub of Example 17, wherein the sensed parameter comprises a modular device fault-detection parameter.

Example 19

The surgical hub of Examples 17 or 18, wherein the sensed parameter comprises a surgeon detection parameter.

Example 20

The surgical hub of any one of Examples 17-19, wherein the sensed parameter comprises a security-threat detection parameter.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term “control circuit” may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein “control circuit” includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical system for use in a surgical procedure, wherein the surgical system comprises:

a modular surgical device comprising at least one sensor;

at least one data source; and a surgical hub configured to communicably couple to the at least one data source and the modular surgical device, wherein the surgical hub comprises a control circuit configured to:

receive a sensed parameter from the at least one sensor of the modular surgical device;

receive data from the at least one data source, wherein the data is determinative of a progress status of the surgical procedure;

perform an adjusted response, by the control circuit, based on the sensed parameter and the data determinative of the progress status of the surgical procedure, wherein the adjusted response configures an operational parameter of the modular surgical device based on the sensed parameter and the data determinative of the progress status of the surgical procedure; and cause the surgical hub to enter a predetermined interactive control mode based on the data determinative of the progress status of the surgical procedure.

2. The surgical system of claim 1, wherein the at least one data source comprises a patient monitoring device.

3. The surgical system of claim 1, wherein the at least one data source comprises a surgical staff detection device.

4. The surgical system of claim 1, wherein the progress status comprises a preoperative status while the surgical procedure is in preoperative steps.

5. The surgical system of claim 1, wherein the progress status comprises an intraoperative status while the surgical procedure is in intraoperative steps.

6. The surgical system of claim 1, wherein the sensed parameter comprises a fault detection parameter.

7. The surgical system of claim 1, wherein the sensed parameter comprises a surgeon detection parameter of the modular surgical device.

8. The surgical system of claim 1, wherein the sensed parameter comprises a security-threat detection parameter.

9. A surgical hub for use in a surgical procedure, wherein the surgical hub is configured to communicably couple to at least one data source, a sensor system, and a surgical instrument, and wherein the surgical hub comprises:

a control circuit configured to:

receive a sensed parameter from the sensor system;

receive data from the at least one data source, wherein the data is determinative of a progress status of the surgical procedure;

perform an adjusted response, by the control circuit, based on the sensed parameter and the data determinative of the progress status of the surgical procedure, wherein the adjusted response configures an operational parameter of the modular surgical device based on the sensed parameter and the data determinative of the progress status of the surgical procedure; and cause the surgical hub to enter a predetermined interactive control mode based on the data determinative of the progress status of the surgical procedure.

10. The surgical hub of claim 9, wherein the at least one data source comprises a patient monitoring device.

11. The surgical hub of claim 9, wherein the at least one data source comprises a surgical staff detection device.

12. The surgical hub of claim 9, wherein the progress status comprises a preoperative status while the surgical procedure is in preoperative steps.

13. The surgical hub of claim 9, wherein the progress status comprises an intraoperative status while the surgical procedure is in intraoperative steps.

14. The surgical hub of claim 9, wherein the sensed parameter comprises a modular device fault-detection parameter.

15. The surgical hub of claim 9, wherein the sensed parameter comprises a surgeon detection parameter.

16. The surgical hub of claim 9, wherein the sensed parameter comprises a security-threat detection parameter.

17. A surgical hub for use in a surgical procedure, wherein the surgical hub is configured to communicably couple to at least one data source, and a modular surgical device, and wherein the surgical hub comprises:

a control circuit configured to:

receive a sensed parameter from an at least one sensor of the modular surgical device;

receive data from the at least one data source, wherein the data is determinative of a situational parameter of the surgical procedure;

perform an adjusted response, by the control circuit, based on the sensed parameter and the data determinative of the situational parameter of the surgical procedure, wherein the adjusted response configures an operational parameter of the modular surgical device based on the sensed parameter and the data determinative of the progress status of the surgical procedure; and cause the surgical hub to enter a predetermined interactive control mode based on the data determinative of the situational parameter of the surgical procedure.

18. The surgical hub of claim 17, wherein the sensed parameter comprises a modular device fault-detection parameter.

19. The surgical hub of claim 17, wherein the sensed parameter comprises a surgeon detection parameter.

20. The surgical hub of claim 17, wherein the sensed parameter comprises a security-threat detection parameter.

* * * * *